(12) United States Patent
Bihi et al.

(10) Patent No.: US 11,471,522 B2
(45) Date of Patent: Oct. 18, 2022

(54) METHODS AND COMPOSITIONS FOR STIMULATING IMMUNE RESPONSE

(71) Applicants: BIONTECH RNA PHARMACEUTICALS GMBH, Mainz (DE); TRON—TRANSLATIONALE ONKOLOGIE AN DER UNIVERSITÄTSMEDIZIN DER JOHANNES GUTENBERG—UNIVERSITAT MAINZ GEMEIN-NUTZIGE GMBH, Mainz (DE)

(72) Inventors: Mahjoub Bihi, Mainz (DE); Ugur Sahin, Mainz (DE); Mustafa Diken, Mainz (DE); Thorsten Klamp, Mainz (DE)

(73) Assignees: BIONTECH SE, Mainz (DE); TRON—TRANSLATIONALE ONKOLOGIE AN DER UNIVERSITÄTSMEDIZIN DER JOHANNES GUTENBERG-UNIVERSITÄT MAINZ GEMEINNÜTZIGE GMBH, Mainz (DE)

( * ) Notice: Subject to any disclaimer, the term of this patent is extended or adjusted under 35 U.S.C. 154(b) by 115 days.

(21) Appl. No.: 16/496,858

(22) PCT Filed: Mar. 21, 2018

(86) PCT No.: PCT/EP2018/057206
§ 371 (c)(1),
(2) Date: Dec. 30, 2019

(87) PCT Pub. No.: WO2018/172426
PCT Pub. Date: Sep. 27, 2018

(65) Prior Publication Data
US 2020/0197508 A1   Jun. 25, 2020

(30) Foreign Application Priority Data

Mar. 24, 2017   (WO) ................. PCT/EP2017/057094

(51) Int. Cl.
*A61K 39/00* (2006.01)
*A61K 39/145* (2006.01)
(Continued)

(52) U.S. Cl.
CPC ............ *A61K 39/145* (2013.01); *C12N 15/11* (2013.01); *A61K 38/00* (2013.01);
(Continued)

(58) Field of Classification Search
None
See application file for complete search history.

(56) References Cited

U.S. PATENT DOCUMENTS 9,518,260 B2 * 12/2016 French ............... A61P 25/04
2013/0052217 A1 * 2/2013 Klamp ............... C07K 14/4748
424/192.1

FOREIGN PATENT DOCUMENTS

WO   WO 2005/097993 A2   10/2005
WO   WO-2008138658 A2 *  11/2008   ............. A61P 31/04
(Continued)

OTHER PUBLICATIONS

Diebold et al., *Science*, American Association for The Advancement of Science, 303 (5663): 1529-1531 (Mar. 5, 2004).
(Continued)

*Primary Examiner* — M Franco G Salvoza
(74) *Attorney, Agent, or Firm* — Neal, Gerber & Eisenberg LLP; Kevin A. O'Connor

(57) ABSTRACT

The present invention relates to methods and compositions for stimulating an immune response. In particular, the present invention relates to immunostimulatory RNA molecules
(Continued)

comprising sequences derived from an Influenza A virus nucleoprotein-encoding RNA molecule that act as adjuvants and/or immunostimulatory agents to enhance host immune responses.

30 Claims, 21 Drawing Sheets

Specification includes a Sequence Listing.

(51) Int. Cl.
*C12N 15/11* (2006.01)
*A61K 38/00* (2006.01)

(52) U.S. Cl.
CPC .............. *A61K 2039/55561* (2013.01); *A61K 2039/572* (2013.01); *A61K 2039/575* (2013.01); *C12N 2760/16134* (2013.01)

(56) References Cited

FOREIGN PATENT DOCUMENTS

| WO | WO 2010/105819 A1 | 9/2010 |
| WO | WO 2016/179034 A2 | 11/2016 |
| WO | WO 2018/172426 A1 | 9/2018 |

OTHER PUBLICATIONS

Kranz et al., *Immunology*, 137, No. Suppl. 1: 761-762 (Sep. 1, 2012).
European Patent Office, International Search Report in International Application No. PCT/EP2018/057206 (dated May 29, 2018).
European Patent Office, Written Opinion in International Application No. PCT/EP2018/057206 (dated May 29, 2018).
European Patent Office, International Preliminary Report on Patentability in International Application No. PCT/EP2018/057206 (dated Sep. 24, 2019).

* cited by examiner

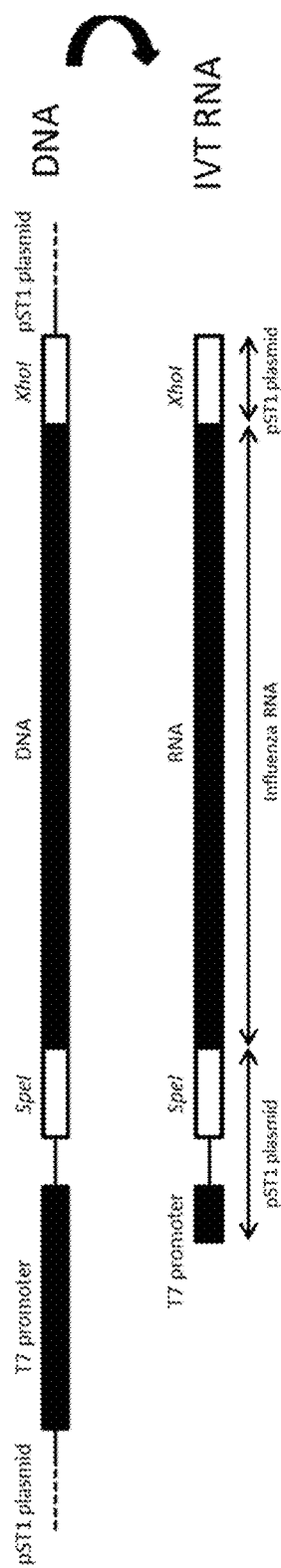

METHODS AND COMPOSITIONS FOR STIMULATING IMMUNE RESPONSE

CROSS-REFERENCE TO RELATED APPLICATIONS

This application is a National Stage Entry of International Application Number PCT/EP2018/057206, which was filed on Mar. 21, 2018 and claimed priority to International Application Number PCT/EP2017/057094, which was filed on Mar. 24, 2017. The contents of each of the aforementioned applications are incorporated herein by reference in their entireties.

TECHNICAL FIELD OF THE INVENTION

The present invention relates to methods and compositions for stimulating an immune response. In particular, the present invention relates to immunostimulatory RNA molecules comprising sequences derived from an Influenza A virus nucleoprotein-encoding RNA molecule that act as adjuvants and/or immunostimulatory agents to enhance host immune responses.

BACKGROUND OF THE INVENTION

The immune system plays an important role in defense against microorganisms, for example viruses, fungi and bacteria, as well as in recognizing and repelling malignant cells (tumor cells). The evolution of the immune system resulted in a highly effective network based on two types of defense: the innate and the adaptive immunity. In contrast to the evolutionary ancient innate immune system that relies on invariant receptors recognizing common molecular patterns associated with pathogens, the adaptive immunity is based on highly specific antigen receptors on B cells (B lymphocytes) and T cells (T lymphocytes) and clonal selection. While B cells raise humoral immune responses by secretion of antibodies, T cells mediate cellular immune responses leading to destruction of recognized cells.

Antigen-specific immunotherapy aims to enhance or induce specific immune responses in patients to control infectious or malignant diseases. The identification of a growing number of pathogen- and tumor-associated antigens led to a broad collection of suitable targets for immunotherapy. Vaccination and immunization is the introduction of a non-virulent antigen into a subject, in which the antigen elicits the subject's immune system to mount an immunological response. Often, vaccine antigens are killed or attenuated forms of the microbes which cause the disease. Different antigen formats can be used for vaccination including whole diseased cells, proteins, peptides or immunizing vectors such as RNA, DNA or viral vectors that can be applied either directly in vivo or in vitro by pulsing of DCs following transfer into the patient. However, antigens are often not sufficiently immunogenic by themselves and do not produce an adequate immune response.

The immunogenicity of an antigen can be increased by administering it in combination with one or more adjuvants. Adjuvants increase the response against the antigen either by directly acting on the immunological system or by modifying the pharmacokinetic characteristics of the antigen, resulting in an increased interaction time between the antigen and the immune system. Additionally, the addition of an adjuvant can permit the use of a smaller dose of antigen to stimulate a similar immune response, thereby reducing the production cost of a vaccine.

A number of compounds exhibiting adjuvant activity have been described. These adjuvants vary in effectiveness and sometimes are not strong enough to induce an immune response of a desired strength, and some have had limited use in humans due to their toxic effects.

Therefore, there is a need for effective adjuvant systems for improving the efficacy and safety of existing and future vaccines.

DESCRIPTION OF INVENTION

Summary of the Invention

The present invention is based, at least in part, on the identification of immunostimulatory RNA molecules comprising sequences derived from an Influenza A virus nucleoprotein-encoding RNA molecule that act as adjuvants or immunostimulatory agents to enhance host immune responses. These immunostimulatory RNA molecules can be used as immunostimulants in vivo.

As described herein, immunostimulatory RNA molecules comprising sequences derived from an Influenza A virus nucleoprotein-encoding RNA molecule have been shown to induce high levels of IFN-α expression in vitro as well as in vivo and strong specific B and T cell responses in vivo. Accordingly, these immunostimulatory RNA molecules are potent adjuvants for vaccination and useful in methods and compositions for stimulating an immune response in a subject. One embodiment of the invention comprises administering an immunostimulatory RNA molecule, as described herein, to the subject, in conjunction with one or more antigens, e.g., antigens contained in vaccines, to enhance or promote an antigen specific immune response.

Accordingly, in one aspect, the invention provides a method for stimulating an immune response in a subject comprising providing to the subject at least one antigen and providing an immunostimulatory RNA molecule, the immunostimulatory RNA molecule comprising a sequence derived from an Influenza A virus nucleoprotein-encoding RNA molecule.

In one embodiment, the sequence derived from an Influenza A virus nucleoprotein-encoding RNA molecule comprises at least one fragment of an Influenza A virus nucleoprotein-encoding RNA molecule, or a variant thereof.

In different embodiments, the sequence derived from an Influenza A virus nucleoprotein-encoding RNA molecule or at least one fragment of an Influenza A virus nucleoprotein-encoding RNA molecule, or a variant thereof is selected from the group consisting of SEQ ID NO: 1, SEQ ID NO: 2, SEQ ID NO: 5, SEQ ID NO: 6, SEQ ID NO: 7, SEQ ID NO: 8, SEQ ID NO: 9, SEQ ID NO: 10, and SEQ ID NO: 11.

In a further aspect, the invention provides a method for stimulating an immune response in a subject comprising providing to the subject at least one antigen and providing an immunostimulatory RNA molecule, the immunostimulatory RNA molecule comprising the sequence of SEQ ID NO: 1, or a variant thereof. In one embodiment, the immunostimulatory RNA molecule comprises the sequence of SEQ ID NO: 2, or a variant thereof.

In one embodiment, the immunostimulatory RNA molecule further comprises the sequence of SEQ ID NO: 3, or a variant thereof. In one embodiment, the immunostimulatory RNA molecule further comprises the sequence of SEQ ID NO: 4, or a variant thereof.

In one embodiment, the immunostimulatory RNA molecule comprises the sequence of SEQ ID NO: 5, or a variant thereof.

In one embodiment, the immunostimulatory RNA molecule comprises the sequence of SEQ ID NO: 6, or a variant thereof. In one embodiment, the immunostimulatory RNA molecule comprises the sequence of SEQ ID NO: 7, or a variant thereof.

In one embodiment, the immunostimulatory RNA molecule comprises the sequence of SEQ ID NO: 8, or a variant thereof. In one embodiment, the immunostimulatory RNA molecule comprises the sequence of SEQ ID NO: 9, or a variant thereof.

In one embodiment, the immunostimulatory RNA molecule comprises the sequence of SEQ ID NO: 10, or a variant thereof. In one embodiment, the immunostimulatory RNA molecule comprises the sequence of SEQ ID NO: 11, or a variant thereof.

In one embodiment of all aspects of the invention, the immunostimulatory RNA molecule is capable of inducing an antigen specific immune response in the subject.

In one embodiment of all aspects of the invention, the immune response comprises a B cell response.

In one embodiment of all aspects of the invention, the immune response comprises the production of IgG antibodies associated with a Th1-like response.

In one embodiment of all aspects of the invention, the immunostimulatory RNA molecule is a toll-like receptor (TLR) agonist. In one embodiment, the TLR is TLR7.

In one embodiment of all aspects of the invention, the immunostimulatory RNA molecule is capable of inducing secretion of interferon alpha. In one embodiment, secretion of interferon alpha involves plasmacytoid dendritic cells.

In one embodiment of all aspects of the invention, the immunostimulatory RNA molecule does not substantially induce secretion of one or more of tumor necrosis factor alpha, interferon gamma and interleukin 10.

In one embodiment of all aspects of the invention, the at least one antigen is selected from the group consisting of cancer, virus, bacterial, fungal, or parasite antigens.

In one embodiment of all aspects of the invention, the subject is a mammal. In one embodiment of all aspects of the invention, the subject is a human.

In a further aspect, the invention provides a pharmaceutical composition comprising an immunostimulatory RNA molecule, at least one antigen, and a pharmaceutically acceptable carrier, the immunostimulatory RNA molecule comprising a sequence derived from an Influenza A virus nucleoprotein-encoding RNA molecule.

In one embodiment, the sequence derived from an Influenza A virus nucleoprotein-encoding RNA molecule comprises at least one fragment of an Influenza A virus nucleoprotein-encoding RNA molecule, or a variant thereof.

In different embodiments, the sequence derived from an Influenza A virus nucleoprotein-encoding RNA molecule or at least one fragment of an Influenza A virus nucleoprotein-encoding RNA molecule, or a variant thereof is selected from the group consisting of SEQ ID NO: 1, SEQ ID NO: 2, SEQ ID NO: 5, SEQ ID NO: 6, SEQ ID NO: 7, SEQ ID NO: 8, SEQ ID NO: 9, SEQ ID NO: 10, and SEQ ID NO: 11.

In a further aspect, the invention provides a pharmaceutical composition comprising an immunostimulatory RNA molecule, at least one antigen, and a pharmaceutically acceptable carrier, the immunostimulatory RNA molecule comprising the sequence of SEQ ID NO: 1, or a variant thereof. In one embodiment, the immunostimulatory RNA molecule comprises the sequence of SEQ ID NO: 2, or a variant thereof.

In one embodiment, the immunostimulatory RNA molecule further comprises the sequence of SEQ ID NO: 3, or a variant thereof. In one embodiment, the immunostimulatory RNA molecule further comprises the sequence of SEQ ID NO: 4, or a variant thereof.

In one embodiment, the immunostimulatory RNA molecule comprises the sequence of SEQ ID NO: 5, or a variant thereof.

In one embodiment, the immunostimulatory RNA molecule comprises the sequence of SEQ ID NO: 6, or a variant thereof. In one embodiment, the immunostimulatory RNA molecule comprises the sequence of SEQ ID NO: 7, or a variant thereof.

In one embodiment, the immunostimulatory RNA molecule comprises the sequence of SEQ ID NO: 8, or a variant thereof. In one embodiment, the immunostimulatory RNA molecule comprises the sequence of SEQ ID NO: 9, or a variant thereof.

In one embodiment, the immunostimulatory RNA molecule comprises the sequence of SEQ ID NO: 10, or a variant thereof. In one embodiment, the immunostimulatory RNA molecule comprises the sequence of SEQ ID NO: 11, or a variant thereof.

In one embodiment of the pharmaceutical composition of all aspects of the invention, the immunostimulatory RNA molecule is a toll-like receptor (TLR) agonist. In one embodiment, the TLR is TLR7.

In one embodiment of the pharmaceutical composition of all aspects of the invention, the at least one antigen is selected from the group consisting of cancer, virus, bacterial, fungal, or parasite antigens.

A pharmaceutical composition described herein may be in the form of a vaccine which may be a therapeutic or prophylactic vaccine.

In a further aspect, the invention provides an isolated RNA molecule comprising a sequence derived from an Influenza A virus nucleoprotein-encoding RNA molecule, wherein the isolated RNA molecule has immunostimulatory activity.

In one embodiment, the sequence derived from an Influenza A virus nucleoprotein-encoding RNA molecule comprises at least one fragment of an Influenza A virus nucleoprotein-encoding RNA molecule, or a variant thereof.

In different embodiments, the sequence derived from an Influenza A virus nucleoprotein-encoding RNA molecule or at least one fragment of an Influenza A virus nucleoprotein-encoding RNA molecule, or a variant thereof is selected from the group consisting of SEQ ID NO: 1, SEQ ID NO: 2, SEQ ID NO: 5, SEQ ID NO: 6, SEQ ID NO: 7, SEQ ID NO: 8, SEQ ID NO: 9, SEQ ID NO: 10, and SEQ ID NO: 11.

In a further aspect, the invention provides an isolated RNA molecule comprising the sequence of SEQ ID NO: 1, or a variant thereof, wherein the isolated RNA molecule has immunostimulatory activity. In one embodiment, the isolated RNA molecule comprises the sequence of SEQ ID NO: 2, or a variant thereof.

In one embodiment, the isolated RNA molecule further comprises the sequence of SEQ ID NO: 3, or a variant thereof. In one embodiment, the isolated RNA molecule further comprises the sequence of SEQ ID NO: 4, or a variant thereof.

In one embodiment, the isolated RNA molecule comprises the sequence of SEQ ID NO: 5, or a variant thereof.

In one embodiment, the isolated RNA molecule comprises the sequence of SEQ ID NO: 6, or a variant thereof. In one embodiment, the isolated RNA molecule comprises the sequence of SEQ ID NO: 7, or a variant thereof.

In one embodiment, the isolated RNA molecule comprises the sequence of SEQ ID NO: 8, or a variant thereof. In one embodiment, the isolated RNA molecule comprises the sequence of SEQ ID NO: 9, or a variant thereof.

In one embodiment, the isolated RNA molecule comprises the sequence of SEQ ID NO: 10, or a variant thereof. In one embodiment, the isolated RNA molecule comprises the sequence of SEQ ID NO: 11, or a variant thereof.

In one embodiment of the isolated RNA molecule of all aspects of the invention, the isolated RNA molecule is a toll-like receptor (TLR) agonist. In one embodiment, the TLR is TLR7.

In one embodiment of the invention, an immunostimulatory RNA molecule or isolated RNA molecule described herein is not translatable, i.e., it is not a template for producing peptide or protein.

Another aspect relates to a method for stimulating an immune response in a subject, comprising administering to the subject a pharmaceutical composition provided according to the invention.

In further aspects, the invention provides the agents and compositions described herein for use in the methods of treatment described herein, in particular for stimulating an immune response.

Other features and advantages of the instant invention will be apparent from the following detailed description and claims.

BRIEF DESCRIPTION OF THE DRAWINGS

FIG. 13: Antigen-specific antibodies elicited by immunization with formulated isRNAs and HBcAg-#A79 VLPs kill target positive cells by CDC

DETAILED DESCRIPTION OF THE INVENTION

Figure 1:
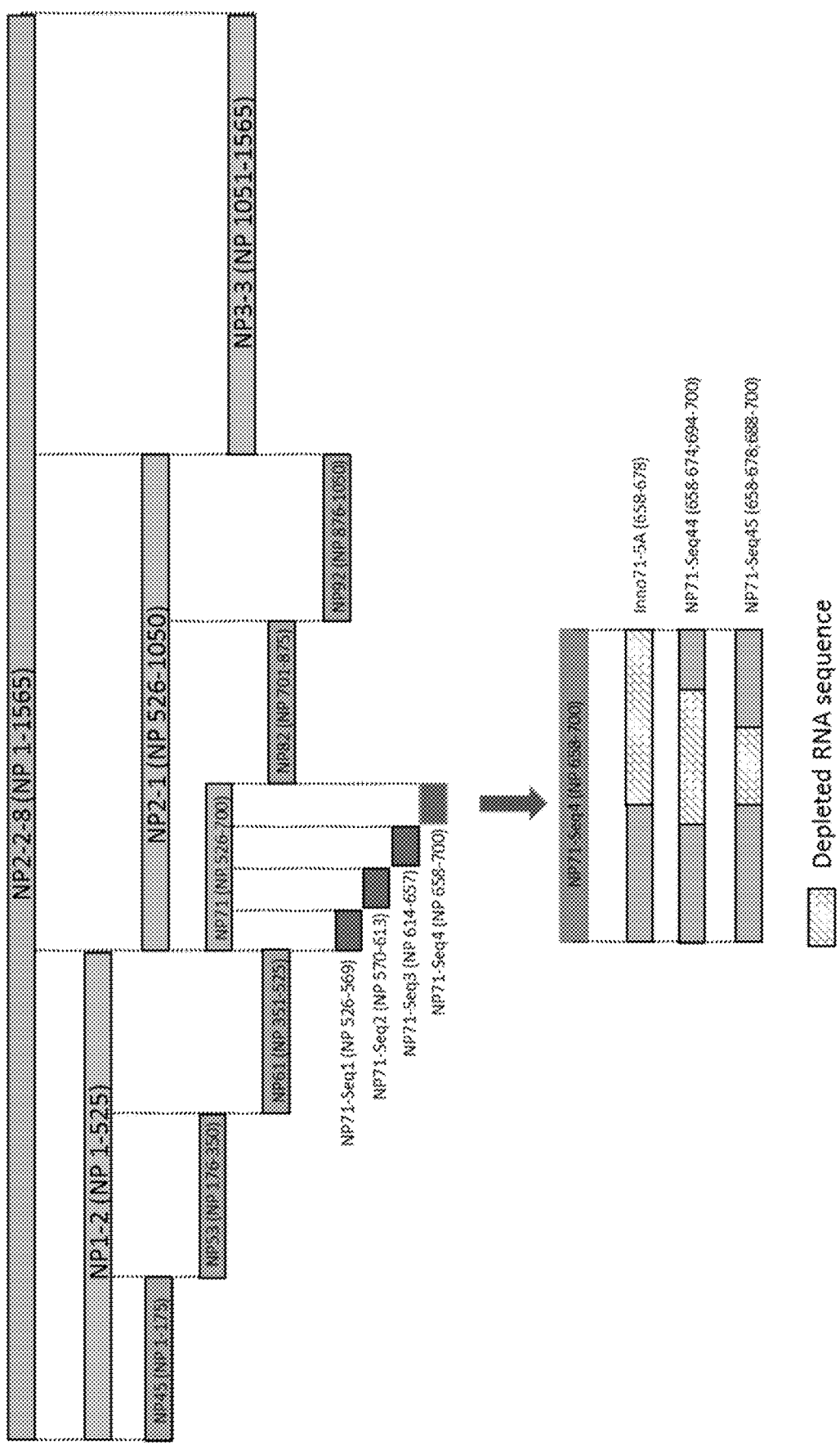
FIG. 1: Schematic overview of the applied sequential fragmentation strategy using Influenza NP encoding RNA (2-2-8, NP 1-1565) as starting sequence

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., (1995) Helvetica Chimica Acta, CH-4010 Basel, Switzerland.

The practice of the present invention will employ, unless otherwise indicated, conventional methods of biochemistry, cell biology, immunology, and recombinant DNA techniques which are explained in the literature in the field (cf., e.g., Molecular Cloning: A Laboratory Manual, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The present invention envisions the treatment or prevention of diseases or disorders by stimulating an immune response to an antigen associated with the disease or disorder. The immune response to the antigen is enhanced by administering a vaccine antigen or a nucleic acid coding for the vaccine antigen in conjunction with one or more immunostimulatory RNA molecules described herein which act as adjuvant.

The term "adjuvant" relates to compounds, which when administered in combination with an antigen to an individual, prolong or enhance or accelerate an immune response. It is assumed that adjuvants exert their biological activity by one or more mechanisms, including an increase of the surface of the antigen, a prolongation of the retention of the antigen in the body, a retardation of the antigen release, targeting of the antigen to macrophages, increase of the uptake of the antigen, enhancement of antigen processing, stimulation of cytokine release, stimulation and activation of immune cells such as B cells, macrophages, dendritic cells, T cells and unspecific activation of immune cells.

The present invention describes immunostimulatory RNA molecules comprising sequences derived from an Influenza A virus nucleoprotein-encoding RNA molecule that act as adjuvants and/or immunostimulatory agents to enhance host immune responses.

The term "Influenza A virus nucleoprotein-encoding RNA molecule" relates to an RNA molecule encoding the nucleoprotein (NP) or nucleocapsid protein of Influenza A virus.

Influenza A viruses have genomes comprising eight segments of RNA encoding 10 identified polypeptides. Nine of these polypeptides are incorporated into virions. Three viral polypeptides are inserted into the lipid envelope: the haemagglutinin (HA) and neuraminidase glycoproteins, involved in cell entry and exit, respectively, and M2, a low abundance ion channel involved in uncoating and HA maturation. Underlying the membrane is the matrix or M1 protein, the major structural component of the virion which is thought to act as an adaptor between the lipid envelope and the internal RNP particles and is probably the driving force behind virus budding. Inside the shell of M1 lie the RNPs: these comprise the genomic RNA segments in association with a trimeric RNA polymerase (PB1, PB2 and PA subunits) and stoichiometric quantities of NP. Also found in the virion are small quantities of the NEP/NS2 polypeptide.

In one embodiment, the term "Influenza A virus nucleoprotein-encoding RNA molecule" relates to a nucleic acid sequence according to SEQ ID NO: 12 of the sequence listing or a variant thereof.

In one embodiment, the immunostimulatory RNA molecules described herein comprise the sequence of SEQ ID NO: 1, or a variant thereof. In one embodiment, the immunostimulatory RNA molecules comprises the sequence of SEQ ID NO: 2, or a variant thereof.

In one embodiment, the immunostimulatory RNA molecules further comprises the sequence of SEQ ID NO: 3, or a variant thereof. In one embodiment, the immunostimulatory RNA molecules further comprises the sequence of SEQ ID NO: 4, or a variant thereof.

In one embodiment, the immunostimulatory RNA molecules described herein comprises the sequence of SEQ ID NO: 5, or a variant thereof.

In one embodiment, the immunostimulatory RNA molecules described herein comprises the sequence of SEQ ID NO: 6, or a variant thereof. In one embodiment, the immunostimulatory RNA molecule comprises the sequence of SEQ ID NO: 7, or a variant thereof.

In one embodiment, the immunostimulatory RNA molecules described herein comprises the sequence of SEQ ID NO: 8, or a variant thereof. In one embodiment, the immunostimulatory RNA molecule comprises the sequence of SEQ ID NO: 9, or a variant thereof.

In one embodiment, the immunostimulatory RNA molecules described herein comprises the sequence of SEQ ID NO: 10, or a variant thereof. In one embodiment, the immunostimulatory RNA molecule comprises the sequence of SEQ ID NO: 11, or a variant thereof.

The immunostimulatory RNA molecules described herein induce immune responses against antigens when administered in conjunction with these antigens. In one embodiment, the immune response comprises a B cell response. In one embodiment, the immune response comprises production of IgG antibodies.

In one embodiment, the immunostimulatory RNA molecules described herein are capable of inducing secretion of interferon alpha. In one embodiment, secretion of interferon alpha involves plasmacytoid dendritic cells.

In one embodiment, the immunostimulatory RNA molecules described herein do not substantially induce secretion of one or more of tumor necrosis factor alpha, interferon gamma and interleukin 10.

In one embodiment, the immunostimulatory RNA molecules described herein are recombinant molecules. In one embodiment, the immunostimulatory RNA molecules described herein are obtained by in vitro transcription.

In various embodiments, the immunostimulatory RNA molecules described herein have a length of between 20 to 400 nucleotides, 20 to 200 nucleotides, 20 to 100 nucleotides, in particular 30 to 200 nucleotides or 30 to 100 nucleotides.

According to the invention it is preferred to administer the immunostimulatory RNA molecules described herein formulated in carriers or delivery vehicles such as in a nanoparticulate formulation, in particular a lipoplex formulation. Accordingly, the immunostimulatory RNA molecules described herein may be present formulated in carriers or delivery vehicles such as in nanoparticulates or a nanoparticulate formulation, in particular a lipoplex formulation, as described herein.

In one embodiment, delivery vehicles may be used which deliver the immunostimulatory RNA molecules to antigen presenting cells such as dendrite cells (DCs) in the spleen after systemic administration. For example, nanoparticulate RNA formulations with defined particle size wherein the net charge of the particles is close to zero or negative, such as electro-neutral or negatively charged lipoplexes from RNA and liposomes, e.g. lipoplexes comprising DOTMA and DOPE or DOTMA and Cholesterol, lead to substantial delivery of RNA to spleen DCs after systemic administration. Particularly preferred according to the invention is a nanoparticulate RNA formulation wherein the charge ratio of positive charges to negative charges in the nanoparticles is 1.4:1 or less and/or the zeta potential of the nanoparticles is 0 or less. In one embodiment, the charge ratio of positive charges to negative charges in the nanoparticles is between 1.4:1 and 1:8, preferably between 1.2:1 and 1:4, e.g. between 1:1 and 1:3 such as between 1:1.2 and 1:2, 1:1.2 and 1:1.8, 1:1.3 and 1:1.7, in particular between 1:1.4 and 1:1.6, such as about 1:1.5. In one embodiment, the zeta potential of the nanoparticles is −5 or less, −10 or less, −15 or less, −20 or less or −25 or less. In various embodiments, the zeta potential of the nanoparticles is −35 or higher, −30 or higher or −25 or higher. In one embodiment, the nanoparticles have a zeta potential from 0 mV to −50 mV, preferably 0 mV to −40 mV or −10 mV to −30 mV. In one embodiment, the positive charges are contributed by at least one cationic lipid present in the nanoparticles and the negative charges are contributed by the RNA. In one embodiment, the nanoparticles comprises at least one helper lipid. The helper lipid may be a neutral or an anionic lipid.

In one embodiment, the nanoparticles are lipoplexes comprising DOTMA and DOPE in a molar ratio of 10:0 to 1:9, preferably 8:2 to 3:7, and more preferably of 7:3 to 5:5 and wherein the charge ratio of positive charges in DOTMA to negative charges in the RNA is 1.8:2 to 0.8:2, more preferably 1.6:2 to 1:2, even more preferably 1.4:2 to 1.1:2 and even more preferably about 1.2:2.

In one embodiment, the nanoparticles are lipoplexes comprising DOTMA and Cholesterol in a molar ratio of 10:0 to 1:9, preferably 8:2 to 3:7, and more preferably of 7:3 to 5:5 and wherein the charge ratio of positive charges in DOTMA to negative charges in the RNA is 1.8:2 to 0.8:2, more preferably 1.6:2 to 1:2, even more preferably 1.4:2 to 1.1:2 and even more preferably about 1.2:2.

In one embodiment, the nanoparticles are lipoplexes comprising DOTAP and DOPE in a molar ratio of 10:0 to 1:9, preferably 8:2 to 3:7, and more preferably of 7:3 to 5:5 and wherein the charge ratio of positive charges in DOTMA to negative charges in the RNA is 1.8:2 to 0.8:2, more preferably 1.6:2 to 1:2, even more preferably 1.4:2 to 1.1:2 and even more preferably about 1.2:2.

In one embodiment, the nanoparticles are lipoplexes comprising DOTMA and DOPE in a molar ratio of 2:1 to 1:2, preferably 2:1 to 1:1, and wherein the charge ratio of positive charges in DOTMA to negative charges in the RNA is 1.4:1 or less.

In one embodiment, the nanoparticles are lipoplexes comprising DOTMA and cholesterol in a molar ratio of 2:1 to 1:2, preferably 2:1 to 1:1, and wherein the charge ratio of positive charges in DOTMA to negative charges in the RNA is 1.4:1 or less.

In one embodiment, the nanoparticles are lipoplexes comprising DOTAP and DOPE in a molar ratio of 2:1 to 1:2, preferably 2:1 to 1:1, and wherein the charge ratio of positive charges in DOTAP to negative charges in the RNA is 1.4:1 or less.

According to the invention, the term "F12" designates liposomes comprising DOTMA and DOPE in a molar ratio of 2:1 and lipoplexes with RNA which are formed using such liposomes.

According to the invention, the term "F5" designates liposomes comprising DOTMA and cholesterol in a molar ratio of 1:1 and lipoplexes with RNA which are formed using such liposomes.

As used herein, the term "nanoparticle" refers to any particle having a diameter making the particle suitable for systemic, in particular parenteral, administration, of, in particular, nucleic acids, typically a diameter of less than 1000 nanometers (nm). In some embodiments, a nanoparticle has a diameter of less than 600 nm. In some embodiments, a nanoparticle has a diameter of less than 400 nm. In some embodiments, a nanoparticle has an average diameter in the range of from about 50 nm to about 1000 nm, preferably from about 50 nm to about 400 nm, preferably about 100 nm to about 300 nm such as about 150 nm to about 200 nm. In some embodiments, a nanoparticle has a diameter in the range of about 200 to about 700 nm, about 200 to about 600 nm, preferably about 250 to about 550 nm, in particular about 300 to about 500 nm or about 200 to about 400 nm.

As used herein, the term "nanoparticulate formulation" or similar terms refer to any substance that contains at least one nanoparticle. In some embodiments, a nanoparticulate formulation is a uniform collection of nanoparticles. In some embodiments, nanoparticulate formulations are dispersions or emulsions. In general, a dispersion or emulsion is formed when at least two immiscible materials are combined.

The term, "lipoplex" or "nucleic acid lipoplex", in particular "RNA lipoplex", refers to a complex of lipids and nucleic acids, in particular RNA. Lipoplexes are formed spontaneously when cationic liposomes, which often also include a neutral "helper" lipid, are mixed with nucleic acids.

If the present invention refers to a charge such as a positive charge, negative charge or neutral charge or a cationic compound, negative compound or neutral compound this generally means that the charge mentioned is present at a selected pH, such as a physiological pH. For example, the term "cationic lipid" means a lipid having a net positive charge at a selected pH, such as a physiological pH. The term "neutral lipid" means a lipid having no net positive or negative charge and can be present in the form of a non-charge or a neutral amphoteric ion at a selected pH, such as a physiological pH. By "physiological pH" herein is meant a pH of about 7.5.

The nanoparticulate carriers such as lipid carriers contemplated for use in the present invention include any substances or vehicles with which nucleic acid such as RNA can be associated, e.g. by forming complexes with the nucleic acid or forming vesicles in which the nucleic acid is enclosed or encapsulated. This may result in increased stability of the nucleic acid compared to naked nucleic acid. In particular, stability of the nucleic acid in blood may be increased.

Cationic lipids, cationic polymers and other substances with positive charges may form complexes with negatively charged nucleic acids. These cationic molecules can be used to complex nucleic acids, thereby forming e.g. so-called lipoplexes or polyplexes, respectively, and these complexes have been shown to deliver nucleic acids into cells.

Nanoparticulate nucleic acid preparations for use in the present invention can be obtained by various protocols and from various nucleic acid complexing compounds. Lipids, polymers, oligomers, or amphipiles are typical complexing agents. In one embodiment, the complexing compound comprises at least one agent selected from the group consisting protamine, polyethyleneimine, a poly-L-lysine, a poly-L-arginine or a histone.

According to the invention, protamine is useful as cationic carrier agent. The term "protamine" refers to any of various strongly basic proteins of relatively low molecular weight that are rich in arginine and are found associated especially with DNA in place of somatic histones in the sperm cells of various animals (as fish). In particular, the term "protamine" refers to proteins found in fish sperm that are strongly basic, are soluble in water, are not coagulated by heat, and yield chiefly arginine upon hydrolysis. In purified form, they are used in a long-acting formulation of insulin and to neutralize the anticoagulant effects of heparin. According to the invention, the term "protamine" as used herein is meant to comprise any protamine amino acid sequence obtained or derived from native or biological sources including fragments thereof and multimeric forms of said amino acid sequence or fragment thereof. Furthermore, the term encompasses (synthesized) polypeptides which are artificial and specifically designed for specific purposes and cannot be isolated from native or biological sources. The protamine used according to the present invention can be sulfated protamine or hydrochloride protamine. In a preferred embodiment, the protamine source used for the production of the nanoparticles described herein is protamine 5000 which contains protamine at more than 10 mg/ml (5000 heparin-neutralizing units per ml) in an isotonic salt solution.

Liposomes are microscopic lipidic vesicles often having one or more bilayers of a vesicle-forming lipid, such as a phospholipid, and are capable of encapsulating a drug. Different types of liposomes may be employed in the context of the present invention, including, without being limited thereto, multilamellar vesicles (MLV), small unilamellar vesicles (SUV), large unilamellar vesicles (LUV), sterically stabilized liposomes (SSL), multivesicular vesicles (MV), and large multivesicular vesicles (LMV) as well as other bilayered forms known in the art. The size and lamellarity of the liposome will depend on the manner of preparation and the selection of the type of vesicles to be used will depend on the preferred mode of administration. There are several other forms of supramolecular organization in which lipids may be present in an aqueous medium, comprising lamellar phases, hexagonal and inverse hexagonal phases, cubic phases, micelles, reverse micelles composed of monolayers. These phases may also be obtained in the combination with DNA or RNA, and the interaction with RNA and DNA may substantially affect the phase state. The described phases may be present in the nanoparticulate nucleic acid formulations of the present invention.

For formation of nucleic acid lipoplexes from nucleic acid and liposomes, any suitable method of forming liposomes can be used so long as it provides the envisaged nucleic acid lipoplexes. Liposomes may be formed using standard methods such as the reverse evaporation method (REV), the ethanol injection method, the dehydration-rehydration method (DRV), sonication or other suitable methods.

After liposome formation, the liposomes can be sized to obtain a population of liposomes having a substantially homogeneous size range.

Bilayer-forming lipids have typically two hydrocarbon chains, particularly acyl chains, and a head group, either polar or nonpolar. Bilayer-forming lipids are either composed of naturally-occurring lipids or of synthetic origin, including the phospholipids, such as phosphatidylcholine, phosphatidylethanolamine, phosphatide acid, phosphatidylinositol, and sphingomyelin, where the two hydrocarbon chains are typically between about 14-22 carbon atoms in length, and have varying degrees of unsaturation. Other suitable lipids for use in the composition of the present invention include glycolipids and sterols such as cholesterol and its various analogs which can also be used in the liposomes.

Cationic lipids typically have a lipophilic moiety, such as a sterol, an acyl or diacyl chain, and have an overall net positive charge. The head group of the lipid typically carries the positive charge. The cationic lipid preferably has a positive charge of 1 to 10 valences, more preferably a positive charge of 1 to 3 valences, and more preferably a positive charge of 1 valence. Examples of cationic lipids include, but are not limited to 1,2-di-O-octadecenyl-3-trimethylammonium propane (DOTMA); dimethyldioctadecyl ammonium (DDAB); 1,2-dioleoyl-3-trimethylammonium-propane (DOTAP); 1,2-dioleoyl-3-dimethylammonium-propane (DODAP); 1,2-diacyloxy-3-dimethylammonium propanes; 1,2-dialkyloxy-3-dimethylammonium propanes; dioctadecyldimethyl ammonium chloride (DODAC), 1,2-dimyristoyloxypropyl-1,3-dimethylhydroxyethyl ammonium (DMRIE), and 2,3-dioleoyloxy-N-[2(spermine carboxamide)ethyl]-N,N-dimethyl-1-propanamium trifluoroacetate (DOSPA). Preferred are DOTMA, DOTAP, DODAC, and DOSPA. Most preferred is DOTMA.

In addition, the nanoparticles described herein preferably further include a neutral lipid in view of structural stability and the like. The neutral lipid can be appropriately selected in view of the delivery efficiency of the nucleic acid-lipid complex. Examples of neutral lipids include, but are not limited to, 1,2-di-(9Z-octadecenoyl)-sn-glycero-3-phosphoethanolamine (DOPE), 1,2-dioleoyl-sn-glycero-3-phosphocholine (DOPC), diacylphosphatidyl choline, diacylphosphatidyl ethanol amine, ceramide, sphingoemyelin, cephalin, sterol, and cerebroside. Preferred is DOPE and/or DOPC. Most preferred is DOPE. In the case where a cationic liposome includes both a cationic lipid and a neutral lipid, the molar ratio of the cationic lipid to the neutral lipid can be appropriately determined in view of stability of the liposome and the like.

According to one embodiment, the nanoparticles described herein may comprise phospholipids. The phospholipids may be a glycerophospholipid. Examples of glycerophospholipid include, without being limited thereto, three types of lipids: (i) zwitterionic phospholipids, which include, for example, phosphatidylcholine (PC), egg yolk phosphatidylcholine, soybean-derived PC in natural, partially hydrogenated or fully hydrogenated form, dimyristoyl phosphatidylcholine (DMPC) sphingomyelin (SM); (ii) negatively charged phospholipids: which include, for example, phosphatidylserine (PS), phosphatidylinositol (PI), phosphatidic acid (PA), phosphatidylglycerol (PG) dipalmipoyl PG, dimyristoyl phosphatidylglycerol (DMPG); synthetic derivatives in which the conjugate renders a zwitterionic phospholipid negatively charged such is the case of methoxy-polyethylene, glycol-distearoyl phosphatidylethanolamine (mPEG-DSPE); and (iii) cationic phospholipids, which include, for example, phosphatidylcholine or sphingomyelin of which the phosphomonoester was O-methylated to form the cationic lipids.

Association of nucleic acid to the lipid carrier can occur, for example, by the nucleic acid filling interstitial spaces of the carrier, such that the carrier physically entraps the nucleic acid, or by covalent, ionic, or hydrogen bonding, or by means of adsorption by non-specific bonds.

The term "immune response" relates to a reaction of the immune system, preferably to an antigen, and preferably refers to a cellular immune response, a humoral immune response, or both. An immune response may be protective/preventive/prophylactic and/or therapeutic. According to the invention, the term "immune response to" or "immune response against" with respect to a target such as an antigen, cell or tissue, relates to an immune response directed against the target.

"Stimulating an immune response" may mean that there was no immune response against a particular target such as target antigen before stimulating an immune response, but it may also mean that there was a certain level of immune response against a particular target before stimulating an immune response and after stimulating an immune response said immune response is enhanced. Thus, "stimulating an immune response" includes "inducing an immune response" and "enhancing an immune response". Preferably, after stimulating an immune response in a subject, said subject is protected from developing a disease such as a cancer disease or the disease condition is ameliorated by stimulating an immune response. For example, an immune response against a tumor antigen may be stimulated in a patient having a cancer disease or in a subject being at risk of developing a cancer disease. Stimulating an immune response in this case may mean that the disease condition of the subject is ameliorated, that the subject does not develop metastases, or that the subject being at risk of developing a cancer disease does not develop a cancer disease.

The terms "cellular immune response", "cellular response", "cell-mediated immunity" or similar terms are meant to include a cellular response directed to cells characterized by expression of an antigen and/or presentation of an antigen with class I or class II MHC. The cellular response relates to cells called T cells or T lymphocytes which act as either "helpers" or "killers". The helper T cells (also termed $CD4^+$ T cells) play a central role by regulating the immune response and the killer cells (also termed cytotoxic T cells, cytolytic T cells, $CD8^+$ T cells or CTLs) kill cells such as diseased cells.

The term "humoral immune response" refers to a process in living organisms wherein antibodies are produced in response to agents and organisms, which they ultimately neutralize and/or eliminate. The specificity of the antibody response is mediated by T and/or B cells through membrane-associated receptors that bind antigen of a single specificity. Following binding of an appropriate antigen and receipt of various other activating signals, B lymphocytes divide, which produces memory B cells as well as antibody secreting plasma cell clones, each producing antibodies that recognize the identical antigenic epitope as was recognized by its antigen receptor. Memory B lymphocytes remain dormant until they are subsequently activated by their specific antigen. These lymphocytes provide the cellular basis of memory and the resulting escalation in antibody response when re-exposed to a specific antigen.

The term "antibody" as used herein, refers to an immunoglobulin molecule, which is able to specifically bind to an epitope on an antigen. In particular, the term "antibody" refers to a glycoprotein comprising at least two heavy (H) chains and two light (L) chains inter-connected by disulfide bonds. The term "antibody" includes monoclonal antibodies, recombinant antibodies, human antibodies, humanized antibodies, chimeric antibodies and combinations of any of the foregoing. Each heavy chain is comprised of a heavy chain variable region (VH) and a heavy chain constant region (CH). Each light chain is comprised of a light chain variable region (VL) and a light chain constant region (CL). The variable regions and constant regions are also referred to herein as variable domains and constant domains, respectively. The VH and VL regions can be further subdivided into regions of hypervariability, termed complementarity determining regions (CDRs), interspersed with regions that are more conserved, termed framework regions (FRs). Each VH and VL is composed of three CDRs and four FRs, arranged from amino-terminus to carboxy-terminus in the following order: FR1, CDR1, FR2, CDR2, FR3, CDR3, FR4. The CDRs of a VH are termed HCDR1, HCDR2 and HCDR3, the CDRs of a VL are termed LCDR1, LCDR2 and LCDR3. The variable regions of the heavy and light chains contain a binding domain that interacts with an antigen. The constant regions of an antibody comprise the heavy chain constant region (CH) and the light chain constant region (CL), wherein CH can be further subdivided into constant domain CH1, a hinge region, and constant domains CH2 and CH3 (arranged from amino-terminus to carboxy-terminus in the following order: CH1, CH2, CH3). The constant regions of the antibodies may mediate the binding of the immunoglobulin to host tissues or factors, including various cells of the immune system (e.g., effector cells) and the first component (C1q) of the classical complement system. Antibodies can be intact immunoglobulins derived from natural sources or from recombinant sources and can be immunoactive portions of intact immunoglobulins. Antibodies are typically tetramers of immunoglobulin molecules. Antibodies may exist in a variety of forms including, for example, polyclonal antibodies, monoclonal antibodies, Fv, Fab and F(ab)2, as well as single chain antibodies and humanized antibodies.

Antibodies described herein include IgA such as IgA1 or IgA2, IgG1, IgG2, IgG3, IgG4, IgE, IgM, and IgD antibodies. In various embodiments, the antibody is an IgG1 antibody, more particularly an IgG1, kappa or IgG1, lambda isotype (i.e. IgG1, κ, λ), an IgG2a antibody (e.g. IgG2a, κ, λ), an IgG2b antibody (e.g. IgG2b, κ, λ), an IgG3 antibody (e.g. IgG3, κ, λ) or an IgG4 antibody (e.g. IgG4, κ, λ).

The term "immunoglobulin" relates to proteins of the immunoglobulin superfamily, preferably to antigen receptors such as antibodies or the B cell receptor (BCR). The immunoglobulins are characterized by a structural domain, i.e., the immunoglobulin domain, having a characteristic immunoglobulin (Ig) fold. The term encompasses membrane bound immunoglobulins as well as soluble immunoglobulins. Membrane bound immunoglobulins are also termed surface immunoglobulins or membrane immunoglobulins, which are generally part of the BCR. Soluble immunoglobulins are generally termed antibodies. Immunoglobulins generally comprise several chains, typically two identical heavy chains and two identical light chains which are linked via disulfide bonds. These chains are primarily composed of immunoglobulin domains, such as the $V_L$ (variable light chain) domain, $C_L$ (constant light chain) domain, $V_H$ (variable heavy chain) domain, and the $C_H$ (constant heavy chain) domains $C_H1$, $C_H2$, $C_H3$, and $C_H4$. There are five types of mammalian immunoglobulin heavy chains, i.e., α, δ, ε, γ, and μ which account for the different classes of antibodies, i.e., IgA, IgD, IgE, IgG, and IgM. As opposed to the heavy chains of soluble immunoglobulins, the heavy chains of membrane or surface immunoglobulins comprise a transmembrane domain and a short cytoplasmic domain at their carboxy-terminus. In mammals there are two types of light chains, i.e., lambda and kappa. The immunoglobulin chains comprise a variable region and a constant region. The constant region is essentially conserved within the different isotypes of the immunoglobulins, wherein the variable part is highly divers and accounts for antigen recognition.

According to the invention, the term "antigen" or "immunogen" covers any substance, preferably a peptide or protein, that is a target of an immune response and/or that will elicit an immune response. In particular, an "antigen" relates to any substance that reacts specifically with antibodies or T-lymphocytes (T-cells). According to the present invention, the term "antigen" comprises any molecule which comprises at least one epitope such as a B cell or T cell epitope suitable for vaccination. Preferably, an antigen in the context of the present invention is a molecule which, optionally after processing, induces an immune reaction, which is preferably specific for the antigen or cells expressing the antigen. According to the present invention, any suitable antigen may be used, which is a candidate for an immune reaction. An antigen is preferably a product which corresponds to or is derived from a naturally occurring antigen. Such naturally occurring antigens may include or may be derived from allergens, viruses, bacteria, fungi, parasites and other infectious agents and pathogens or an antigen may also be a tumor antigen. In preferred embodiments, the antigen is or is derived from a surface polypeptide, i.e. a polypeptide naturally displayed on the surface of a cell, a pathogen, a bacterium, a virus, a fungus, a parasite, an allergen, or a tumor. The antigen may elicit an immune response against a cell, a pathogen, a bacterium, a virus, a fungus, a parasite, an allergen, or a tumor.

According to the present invention, an antigen may be selected from the group comprising a self-antigen and non-self-antigen such as a bacterial antigen, a virus antigen, a fungus antigen, an allergen or a parasite antigen.

In a preferred embodiment, an antigen is associated with a disease or disorder, i.e., the antigen is a disease-associated antigen. The term "disease-associated antigen" refers to all antigens that are of pathological significance. In one particularly preferred embodiment, a disease-associated antigen is present in diseased cells, tissues and/or organs while it is not present or present in a reduced amount in healthy cells, tissues and/or organs and, thus, can be used for targeting diseased cells, tissues and/or organs. In one embodiment, a disease-associated antigen is present on the surface of a diseased cell. In one embodiment, a disease-associated antigen is a molecule which contains at least one epitope that will stimulate a host's immune system to make a humoral and/or cellular immune response against the disease. The disease-associated antigen may therefore be used for therapeutic purposes. Disease-associated antigens are preferably associated with infection by microbes, typically microbial antigens, or associated with cancer, typically tumors.

In some embodiments the antigen is or is derived from a bacterial antigen. In some embodiments, the antigen elicits an immune response against a bacterium which infects animals, including birds, fish and mammals, including domesticated animals. Preferably, the bacterium against which the immune response is elicited is a pathogenic bacterium.

In some embodiments the antigen is or is derived from a virus antigen. A virus antigen may for example be a peptide from a virus surface protein, e.g. a capsid polypeptide or a spike polypeptide. In some embodiments, the antigen elicits an immune response against a virus which infects animals, including birds, fish and mammals, including domesticated animals. Preferably, the virus against which the immune response is elicited is a pathogenic virus.

In some embodiments the antigen is or is derived from a peptide or protein from a fungus. In some embodiments, the antigen elicits an immune response against a fungus which infects animals, including birds, fish and mammals, including domesticated animals. Preferably, the fungus against which the immune response is elicited is a pathogenic fungus.

In some embodiments the antigen is or is derived from a peptide or protein from a unicellular eukaryotic parasite. In some embodiments, the antigen elicits an immune response against a unicellular eukaryotic parasite, preferably a pathogenic unicellular eukaryotic parasite. Pathogenic unicellular eukaryotic parasites may be e.g. from the genus *Plasmodium*, e.g. *P. falciparum*, *P. vivax*, *P. malariae* or *P. ovale*, from the genus *Leishmania*, or from the genus *Trypanosoma*, e.g. *T. cruzi* or *T. brucei*.

In some embodiments the antigen is or is derived from an allergenic peptide or an allergenic protein. An allergenic peptide or allergenic protein is suitable for allergen immunotherapy, also known as hypo-sensitization.

In a preferred embodiment, an antigen is a tumor antigen or tumor-associated antigen, i.e., a constituent of cancer cells which may be derived from the cytoplasm, the cell surface and the cell nucleus, in particular those antigens which are produced, preferably in large quantity, as surface antigens on cancer cells.

In the context of the present invention, the term "tumor antigen" or "tumor-associated antigen" relates to proteins that are under normal conditions specifically expressed in a limited number of tissues and/or organs or in specific developmental stages, for example, the tumor antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2. The tumor antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. In the context of the present invention, the tumor antigen is preferably associated with the cell surface of a cancer cell and is preferably not or only rarely expressed in normal tissues. Preferably, the tumor antigen or the aberrant expression of the tumor antigen identifies cancer cells. In the context of the present invention, the tumor antigen that is expressed by a cancer cell in a subject, e.g., a patient suffering from a cancer disease, is preferably a self-protein in said subject. In preferred embodiments, the tumor antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system.

Preferably, the amino acid sequence of the tumor antigen is identical between the tumor antigen which is expressed in normal tissues and the tumor antigen which is expressed in cancer tissues.

Examples for tumor antigens that may be useful in the present invention are p53, ART-4, BAGE, beta-catenin/m, Bcr-abL CAMEL, CAP-1, CASP-8, CDC27/m, CDK4/m, CEA, the cell surface proteins of the claudin family, such as CLAUDIN-6, CLAUDIN-18.2 and CLAUD1N-12, c-MYC, CT, Cyp-B, DAM, ELF2M, ETV6-AML1, G250, GAGE, GnT-V, Gap100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12, MAGE-B, MAGE-C, MART-1/Melan-A, MC1R, Myosin/m, MUC1, MUM-1, -2, -3, NA88-A, NF1, NY-ESO-1, NY-BR-1, p190 minor BCR-abL, Pm1/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE and WT. Particularly preferred tumor antigens include CLAUDIN-18.2 (CLDN18.2) and CLAUDIN-6 (CLDN6).

An antigen which is provided according to the invention to a subject either by administering the antigen or a nucleic acid coding for the antigen, i.e. a vaccine antigen, should result in a B cell response and/or T cell response. The antibodies and/or T cells should be directed against a target antigen, in particular a target antigen expressed by or in diseased cells, tissues and/or organs, i.e. a disease-associated antigen. Thus, a vaccine antigen may correspond to or comprise the disease-associated antigen, or it may be a variant thereof. In one embodiment, such variant is immunologically equivalent to the disease-associated antigen. In the context of the present invention, the term "variant of an antigen" means an agent which results in a B cell response and/or T cell response targeting the antigen, i.e. a disease-associated antigen, in particular when expressed in diseased cells, tissues and/or organs, or cells expressing the antigen and optionally presenting the antigen in the context of MHC molecules. Thus, the vaccine antigen may be identical to the disease-associated antigen, may comprise the disease-associated antigen or a portion thereof or may comprise an antigen which is homologous to the disease-associated antigen or a portion thereof. If the vaccine antigen comprises a portion of the disease-associated antigen or a portion of an antigen which is homologous to the disease-associated antigen said portion may comprise an epitope of the disease-associated antigen to which the B cell response and/or T cell response is to be targeted. Thus, according to the invention, an antigen may comprise an immunogenic fragment of a disease-associated antigen such as a peptide fragment of a disease-associated antigen. An "immunogenic fragment of an antigen" according to the invention preferably relates to a portion or fragment of an antigen which is capable of stimulating a B cell response and/or T cell response. The vaccine antigen or the nucleic acid encoding a vaccine antigen to be administered according to the invention may be a recombinant antigen or recombinant nucleic acid.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect. In the context of the present invention, the term "immunologically equivalent" is preferably used with respect to the immunological effects or properties of antigens or antigen variants used for immunization. For example, an amino acid sequence is immunologically equivalent to a reference amino acid sequence if said amino acid sequence when exposed to the immune system of a subject induces an immune reaction having a specificity of reacting with the reference amino acid sequence.

The term "epitope" refers to an antigenic determinant in a molecule such as an antigen, i.e., to a part in or fragment of the molecule that is recognized, i.e. bound, by the immune system, for example, that is recognized by an antibody or T cell receptor. For example, epitopes are the discrete, three-dimensional sites on an antigen, which are recognized by the immune system. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. Preferably an epitope is capable of eliciting an immune response against the antigen or a cell expressing the antigen. Preferably, the term relates to an immunogenic portion of an antigen comprising the epitope. An epitope of a protein such as a tumor antigen preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 9, 10, 11, 12, 13, 14, 15, 16, 17, 18, 19, 20, 21, 22, 23, 24, or 25 amino acids in length. It is preferred that the epitope in the context of the present invention is a B cell epitope or T cell epitope.

As used herein, the term "T cell epitope" refers to a peptide which binds to a MHC molecule in a configuration recognized by a T cell receptor. Typically, T cell epitopes are presented on the surface of an antigen presenting cell. A "T cell epitope" according to the invention preferably relates to a portion or fragment of an antigen which is capable of stimulating an immune response, preferably a cellular response against the antigen or cells characterized by expression of the antigen and preferably by presentation of the antigen. Preferably, a T cell epitope is capable of stimulating a cellular response against a cell characterized by presentation of an antigen. Preferably, T cell epitopes are MHC class I and/or class II presented peptides. Preferably, T cell epitopes comprise an amino acid sequence substantially corresponding to the amino acid sequence of a fragment of an antigen. Preferably, said fragment of an antigen is an MHC class I and/or class II presented peptide. A peptide which is suitable for binding to an MHC molecule, in particular a class I MHC molecule, preferably is 7-20 amino acids in length, more preferably 7-12 amino acids in length, more preferably 8-11 amino acids in length, in particular 9 or 10 amino acids in length. In one embodiment, a T cell epitope when presented in the context of MHC such as MHC of antigen presenting cells is recognized by a T cell receptor. The T cell epitope if recognized by a T cell receptor may be able to induce in the presence of appropriate co-stimulatory signals, clonal expansion of the T cell carrying the T cell receptor specifically recognizing the T cell epitope. Preferably, T cell epitopes, in particular if presented in the context of MHC molecules, are capable of stimulating an immune response, preferably a cellular response against the antigen from which they are derived or cells characterized by expression of the antigen and preferably characterized by presentation of the antigen.

According to the invention, a T cell epitope may be present in a vaccine antigen as a part of a larger entity such as a vaccine sequence and/or a polypeptide comprising more than one T cell epitope. The presented peptide or T cell epitope is produced following suitable processing. Also, T cell epitopes may be modified at one or more residues that are not essential for TCR recognition or for binding to MHC. Such modified T cell epitopes may be considered immunologically equivalent.

Vaccination according to the invention using antigens as described herein preferably results in an immune response against disease-associated antigens or epitopes thereof. Preferably such disease-associated antigens or epitopes thereof comprise one or more disease specific amino acid modifications, e.g. they comprise or are disease-associated neo-antigens or neo-epitopes. Preferably, a disease specific amino acid modification is due to one or more disease specific somatic mutations. In one particularly preferred embodiment, a disease specific amino acid modification is a cancer specific amino acid modification and a disease specific somatic mutation is a cancer specific somatic mutation. Thus, in one embodiment, a vaccine antigen preferably features disease specific amino acid modifications/disease specific somatic mutations of a patient and preferably upon administration provides one or more mutation based neo-epitopes. Thus, the vaccine antigen may comprise a peptide or polypeptide comprising one or more mutation based neo-epitopes. In one embodiment, disease specific amino acid modifications are identified by identifying disease specific somatic mutations, e.g. by sequencing genomic DNA and/or RNA of diseased tissue or one or more diseased cells.

As used herein the term "neo-epitope" refers to an epitope that is not present in a reference such as a normal non-diseased (e.g. non-cancerous) or germline cell but is found in diseased cells (e.g. cancer cells). This includes, in particular, situations wherein in a normal non-diseased or germline cell a corresponding epitope is found, however, due to one or more mutations in a diseased cell the sequence of the epitope is changed so as to result in the neo-epitope.

According to the invention, the term "vaccine" relates to a pharmaceutical preparation (pharmaceutical composition) or product that upon administration induces an immune response, which recognizes and attacks a pathogen or a diseased cell such as a cancer cell. A vaccine may be used for the prevention or treatment of a disease. In particular, the term "vaccine" refers to a composition that includes an antigen, as defined herein.

In one embodiment, a vaccine provided according to the invention comprises a vaccine antigen, herein also referred to simply as "antigen", as described herein for stimulating a therapeutically or prophylactically useful immune response or a nucleic acid, preferably RNA, encoding peptide or protein antigen.

The antigens described herein when administered to a subject preferably provide one or more epitopes suitable for stimulating a disease-specific immune response. In one embodiment, the disease-specific immune response is an antigen-specific immune response which preferably is directed against a disease-associated antigen. Presentation of these epitopes, e.g. by diseased cells or pathogenic agents, serves as a label for targeting by the immune response.

In one embodiment of the invention, an antigen described herein is a or is provided in the form of a virus like particle (VLP). Virus like particles resemble viruses, but are non-infectious because they contain no viral genetic material. The expression of viral structural proteins, such as envelope or capsid, can result in the self-assembly of virus like particles. Virus like particles have been produced from components of a wide variety of virus families including Parvoviridae (e.g. adeno-associated virus), Retroviridae (e.g. HIV), Flaviviridae (e.g. Hepatitis C virus) and bacteriophages (e.g. Qβ, AP205). Virus like particles can be produced in multiple cell culture systems including bacteria, mammalian cell lines, insect cell lines, yeast and plant cells. Virus like particles are useful as vaccines. Virus like particles contain repetitive, high density displays of viral surface proteins that present conformational viral epitopes that can elicit strong T cell and B cell immune responses. Since virus like particles cannot replicate, they provide a safer alternative to attenuated viruses.

Virus like particles, such as virus-like particles from hepatitis B virus core antigen (HBcAg), are also useful as non-infectious carriers of foreign immunological epitopes. The hepatitis B virus core antigen (HBcAg) assembles spontaneously to particulate icosahedral nucleocapsids. The virus like particles such as recombinant HBcAg particles can be used to display epitopes of virus proteins, bacterial and protozoan protein epitopes as well as epitopes of tumor antigens. The highly repetitive, dense display and spacing of the inserted epitopes seems optimal for B-cell receptor cross-linking.

The immunotherapeutic approaches according to the invention include immunization with peptide or protein antigen (native or modified), nucleic acid encoding peptide or protein antigen, recombinant cells encoding peptide or protein antigen, recombinant viruses encoding peptide or protein antigen and antigen presenting cells pulsed with peptide or protein antigen (native or modified) or transfected with nucleic acids encoding peptide or protein antigen.

In one embodiment, the aim is to provide an immune response against cancer cells expressing a tumor antigen and to treat a cancer disease involving cells expressing a tumor antigen. Said cancer cells expressing a tumor antigen may express the tumor antigen on the surface of said cancer cells and/or may present the tumor antigen on the cell surface in the context of MHC molecules. Cancer cells expressing a tumor antigen on the cell surface can be targeted by antibodies directed to the tumor antigen, in particular the extracellular portion of the tumor antigen. Cancer cells presenting a tumor antigen on the cell surface in the context of MHC molecules can be targeted by T cells directed to a T cell epitope of the tumor antigen.

"Cell surface" is used in accordance with its normal meaning in the art, and thus includes the outside of the cell which is accessible to binding by proteins and other molecules. An antigen is expressed on the surface of cells if it is located at the surface of said cells and is accessible to binding by e.g. antigen-specific antibodies added to the cells. In one embodiment, an antigen expressed on the surface of cells is an integral membrane protein having an extracellular portion.

The term "extracellular portion" or "exodomain" in the context of the present invention refers to a part of a molecule such as a protein that is facing the extracellular space of a cell and preferably is accessible from the outside of said cell, e.g., by binding molecules such as antibodies located outside the cell. Preferably, the term refers to one or more extracellular loops or domains or a fragment thereof.

The terms "portion" or "part" are used interchangeably herein and refer to a continuous or discontinuous element of a structure such as an amino acid sequence. The term "fragment" refers to a continuous element of a structure such as an amino acid sequence. A portion, part or fragment of a structure preferably comprises one or more functional properties, e.g. antigenic, immunologic and/or binding properties, of said structure. A portion or part of a protein sequence preferably comprises at least 6, in particular at least 8, at least 12, at least 15, at least 20, at least 30, at least 50, or at least 100 consecutive and/or non-consecutive amino acids of the protein sequence. A fragment of a protein sequence preferably comprises at least 6, in particular at least 8, at least 12, at least 15, at least 20, at least 30, at least 50, or at least 100 consecutive amino acids of the protein sequence.

The term "immunogenicity" relates to the relative effectivity of an antigen to induce an immune reaction.

The term "immunostimulatory" is used herein to refer to increasing overall immune response.

The term "target" shall mean an agent such as a cell, in particular a cancer cell, which is a target for an immune response. Targets include cells that present an antigen or an antigen epitope, i.e. a peptide fragment derived from an antigen. In one embodiment, the target cell is a cell expressing a target antigen which is preferably present on the cell surface.

"Antigen processing" refers to the degradation of an antigen into procession products, which are fragments of said antigen (e.g., the degradation of a protein into peptides) and the association of one or more of these fragments (e.g., via binding) with MHC molecules for presentation by cells, preferably antigen presenting cells to specific T cells.

An antigen-presenting cell (APC) is a cell that displays antigen in the context of major histocompatibility complex (MHC) on its surface. T cells may recognize this complex using their T cell receptor (TCR). Antigen-presenting cells process antigens and present them to T cells. An antigen presenting cell includes, but is not limited to, monocytes/macrophages, B cells and dendritic cells (DCs). According to the invention, the term "antigen-presenting cell" includes professional antigen-presenting cells and non-professional antigen-presenting cells.

Professional antigen-presenting cells are very efficient at internalizing antigen, either by phagocytosis or by receptor-mediated endocytosis, and then displaying a fragment of the antigen, bound to a class II MHC molecule, on their membrane. The T cell recognizes and interacts with the antigen-class II MHC molecule complex on the membrane of the antigen-presenting cell. An additional co-stimulatory signal is then produced by the antigen-presenting cell, leading to activation of the T cell. The expression of co-stimulatory molecules is a defining feature of professional antigen-presenting cells.

The main types of professional antigen-presenting cells are dendritic cells, which have the broadest range of antigen presentation, and are probably the most important antigen-presenting cells, macrophages, B-cells, and certain activated epithelial cells.

Non-professional antigen-presenting cells do not constitutively express the MHC class II proteins required for interaction with naive T cells; these are expressed only upon stimulation of the non-professional antigen-presenting cells by certain cytokines such as IFNγ.

Dendritic cells (DCs) are leukocyte populations that present antigens captured in peripheral tissues to T cells via both MHC class II and I antigen presentation pathways. It is well known that dendritic cells are potent inducers of immune responses and the activation of these cells is a critical step for the induction of immunity.

Dendritic cells are conveniently categorized as "immature" and "mature" cells, which can be used as a simple way to discriminate between two well characterized phenotypes. However, this nomenclature should not be construed to exclude all possible intermediate stages of differentiation.

Immature dendritic cells are characterized as antigen presenting cells with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e. g. CD54 and CD11) and costimulatory molecules (e. g., CD40, CD80, CD86 and 4-1 BB).

Dendritic cell maturation is referred to as the status of dendritic cell activation at which such antigen-presenting dendritic cells lead to T cell priming, while presentation by immature dendritic cells results in tolerance. Dendritic cell maturation is chiefly caused by biomolecules with microbial features detected by innate receptors (bacterial DNA, viral RNA, endotoxin, etc.), pro-inflammatory cytokines (TNF, IL-1, IFNs), ligation of CD40 on the dendritic cell surface by CD40L, and substances released from cells undergoing stressful cell death. The dendritic cells can be derived by culturing bone marrow cells in vitro with cytokines, such as granulocyte-macrophage colony-stimulating factor (GM-CSF) and tumor necrosis factor alpha.

The term "plasmacytoid dendritic cells" or "pDCs" relates to innate immune cells that circulate in the blood and are found in peripheral lymphoid organs. They develop from bone marrow hematopoietic stem cells and constitute <0.4% of peripheral blood mononuclear cells (PBMC). In humans plasmacytoid dendritic cells exhibit plasma cell morphology and express CD4, HLA-DR, CD123, blood-derived dendritic cell antigen-2 (BDCA-2), Toll-like receptor (TLR) 7 and TLR9 within endosomal compartments, but do not express high levels of CD11c or CD14, which distinguishes them from conventional dendritic cells or monocytes, respectively. As components of the innate immune system, plasmacytoid dendritic cells express intracellular Toll-like receptors 7 and 9 which detect ssRNA and unmethylated CpG DNA sequences, respectively. Upon stimulation and subsequent activation, these cells produce large amounts (up to 1,000 times more than other cell types) of type I interferon (mainly IFN-α (alpha) and IFN-β (beta)).

By "cell characterized by presentation of an antigen" or "cell presenting an antigen" or similar expressions is meant a cell such as a diseased cell, e.g. a cancer cell, or an antigen presenting cell presenting an antigen or a fragment derived from said antigen, e.g. by processing of the antigen, in the context of MHC molecules, in particular MHC Class I molecules. Similarly, the terms "disease characterized by presentation of an antigen" denotes a disease involving cells characterized by presentation of an antigen, in particular with class I MHC.

The term "immunoreactive cell" or "effector cell" in the context of the present invention relates to a cell which exerts effector functions during an immune reaction. An "immunoreactive cell" preferably is capable of binding an antigen or a cell characterized by expression and/or presentation of an antigen or an epitope and mediating an immune response. For example, such cells secrete cytokines and/or chemokines, kill microbes, secrete antibodies, recognize infected or cancerous cells, and optionally eliminate such cells. For example, immunoreactive cells comprise T cells (cytotoxic T cells, helper T cells, tumor infiltrating T cells), B cells, natural killer cells, neutrophils, macrophages, and dendritic cells.

Preferably, an "immunoreactive cell" recognizes an antigen or an epitope with some degree of specificity, in particular if presented in the context of MHC molecules such as on the surface of antigen presenting cells or diseased cells such as tumor cells. Preferably, said recognition enables the cell that recognizes an antigen or an epitope to be responsive or reactive. If the cell is a helper T cell (CD4$^+$ T cell) bearing receptors that recognize an antigen or an epitope in the context of MHC class II molecules such responsiveness or reactivity may involve the release of cytokines and/or the activation of CD8+ lymphocytes (CTLs) and/or B-cells. If the cell is a CTL such responsiveness or reactivity may involve the elimination of cells presented in the context of MHC class I molecules, i.e., cells characterized by presentation of an antigen with class I MHC, for example, via apoptosis or perforin-mediated cell lysis. According to the invention, CTL responsiveness may include sustained calcium flux, cell division, production of cytokines such as IFN-γ and TNF-α, up-regulation of activation markers such as CD44 and CD69, and specific cytolytic killing of antigen expressing target cells. CTL responsiveness may also be determined using an artificial reporter that accurately indicates CTL responsiveness. Such CTL that recognizes an antigen or an epitope and are responsive or reactive are also termed "antigen-responsive CTL" herein. If the cell is a B cell such responsiveness may involve the release of immunoglobulins.

The term "T cell" or "T lymphocyte" relates to thymus-derived cells that participate in a variety of cell-mediated immune reactions and includes T helper cells (CD4+ T cells) and cytotoxic T cells (CTLs, CD8+ T cells) which comprise cytolytic T cells.

T cells belong to a group of white blood cells known as lymphocytes, and play a central role in cell-mediated immunity. They can be distinguished from other lymphocyte types, such as B cells and natural killer cells by the presence of a special receptor on their cell surface called T cell receptor (TCR). The thymus is the principal organ responsible for the maturation of T cells. Several different subsets of T cells have been discovered, each with a distinct function.

T helper cells assist other white blood cells in immunologic processes, including maturation of B cells into plasma cells and activation of cytotoxic T cells and macrophages, among other functions. These cells are also known as CD4+ T cells because they express the CD4 protein on their surface. Helper T cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T cells destroy virally infected cells and tumor cells, and are also implicated in transplant rejection. These cells are also known as CD8+ T cells since they express the CD8 glycoprotein at their surface. These cells recognize their targets by binding to antigen associated with MHC class I, which is present on the surface of nearly every cell of the body.

A majority of T cells have a T cell receptor (TCR) existing as a complex of several proteins. The actual T cell receptor is composed of two separate peptide chains, which are produced from the independent T cell receptor alpha and beta (TCRα and TCRβ) genes and are called α- and β-TCR chains. γδ T cells (gamma delta T cells) represent a small subset of T cells that possess a distinct T cell receptor (TCR) on their surface. However, in γδ T cells, the TCR is made up of one γ-chain and one δ-chain. This group of T cells is much less common (2% of total T cells) than the αβ T cells.

The structure of the T cell receptor is very similar to immunoglobulin Fab fragments, which are regions defined as the combined light and heavy chain of an antibody arm. Each chain of the TCR is a member of the immunoglobulin superfamily and possesses one N-terminal immunoglobulin (Ig)-variable (V) domain, one Ig-constant (C) domain, a transmembrane/cell membrane-spanning region, and a short cytoplasmic tail at the C-terminal end. The variable domain of both the TCR α-chain and β-chain have three hypervariable or complementarity determining regions (CDRs), whereas the variable region of the β-chain has an additional area of hypervariability (HV4) that does not normally contact antigen and therefore is not considered a CDR. CDR3 is the main CDR responsible for recognizing processed antigen, although CDR1 of the α-chain has also been shown to interact with the N-terminal part of the antigenic peptide, whereas CDR1 of the n-chain interacts with the C-terminal part of the peptide. CDR2 is thought to recognize the MHC. CDR4 of the β-chain is not thought to participate in antigen recognition, but has been shown to interact with superantigens. The constant domain of the TCR domain consists of short connecting sequences in which a cysteine residue forms disulfide bonds, which forms a link between the two chains.

The term "B cell" or "B lymphocyte" relates to a type of white blood cell of the lymphocyte subtype which function in humoral immunity by secreting antibodies. Additionally, B cells present antigen and are classified as professional antigen-presenting cells (APCs) and secrete cytokines. B cells express B cell receptors (BCRs) on their cell membrane. BCRs allow the B cell to bind a specific antigen, against which it will initiate an antibody response. The B-cell receptor is composed of two parts, a membrane-bound immunoglobulin molecule of one isotype (IgD, IgM, IgA, IgG, or IgE) which with the exception of the presence of an integral membrane domain are identical to their secreted forms and a signal transduction moiety: a heterodimer called Ig-α/Ig-β (CD79), bound together by disulfide bridges. Each member of the dimer spans the plasma membrane and has a cytoplasmic tail bearing an immunoreceptor tyrosine-based activation motif (ITAM).

B cell activation occurs in the secondary lymphoid organs, such as the spleen and lymph nodes. After B cells mature in the bone marrow, they migrate through the blood to secondary lymphoid organs, which receive a constant supply of antigen through circulating lymph. B cell activation begins when the B cell binds to an antigen via its BCR. Different B cell subsets undergo T cell-dependent activation or T cell-independent activation.

The term "peripheral blood mononuclear cell" or "PBMC" relates to a peripheral blood cell having a round nucleus. These cells consist of lymphocytes (T cells, B cells, NK cells) and monocytes, whereas erythrocytes and platelets have no nuclei, and granulocytes (neutrophils, basophils, and eosinophils) have multi-lobed nuclei. These cells can be extracted from whole blood using ficoll and gradient centrifugation, which will separate the blood into a top layer of plasma, followed by a layer of PBMCs and a bottom fraction of polymorphonuclear cells (such as neutrophils and eosinophils) and erythrocytes.

The term "major histocompatibility complex" and the abbreviation "MHC" include MHC class I and MHC class II molecules and relate to a complex of genes which occurs in all vertebrates. MHC proteins or molecules are important for signaling between lymphocytes and antigen presenting cells or diseased cells in immune reactions, wherein the MHC proteins or molecules bind peptides and present them for recognition by T cell receptors. The proteins encoded by the MHC are expressed on the surface of cells, and display both self antigens (peptide fragments from the cell itself) and nonself antigens (e.g., fragments of invading microorganisms) to a T cell.

The MHC region is divided into three subgroups, class I, class II, and class III. MHC class I proteins contain an α-chain and β2-microglobulin (not part of the MHC encoded by chromosome 15). They present antigen fragments to cytotoxic T cells. On most immune system cells, specifically on antigen-presenting cells, MHC class II proteins contain α- and β-chains and they present antigen fragments to T-helper cells. MHC class III region encodes for other immune components, such as complement components and some that encode cytokines.

In humans, genes in the MHC region that encode antigen-presenting proteins on the cell surface are referred to as human leukocyte antigen (HLA) genes. However the abbreviation MHC is often used to refer to HLA gene products. HLA genes include the nine so-called classical MHC genes: HLA-A, HLA-B, HLA-C, HLA-DPA1, HLA-DPB1, HLA-DQA1, HLA-DQB1, HLA-DRA, and HLA-DRB1.

In one preferred embodiment of all aspects of the invention an MHC molecule is an HLA molecule.

The term "immune effector functions" or "effector functions" in the context of the present invention includes any functions mediated by components of the immune system that result, for example, in the killing of cells. Preferably, the immune effector functions in the context of the present invention are T cell mediated effector functions. Such functions comprise in the case of a helper T cell ($CD4^+$ T cell) the recognition of an antigen or an antigen peptide derived from an antigen in the context of MHC class II molecules by T cell receptors, the release of cytokines and/or the activation of $CD8^+$ lymphocytes (CTLs) and/or B-cells, and in the case of CTL the recognition of an antigen or an antigen peptide derived from an antigen in the context of MHC class I molecules by T cell receptors, the elimination of cells presented in the context of MHC class I molecules, i.e., cells characterized by presentation of an antigen with class I MHC, for example, via apoptosis or perforin-mediated cell lysis, production of cytokines such as IFN-γ and TNF-α, and specific cytolytic killing of antigen expressing target cells.

"Antibody-dependent cell-mediated cytotoxicity" or "ADCC" describes the cell-killing ability of effector cells as described herein, in particular lymphocytes, which preferably requires the target cell being marked by an antibody. ADCC preferably occurs when antibodies bind to antigens on tumor cells and the antibody Fc domains engage Fc receptors (FcR) on the surface of immune effector cells. Several families of Fc receptors have been identified, and specific cell populations characteristically express defined Fc receptors. ADCC can be viewed as a mechanism to directly induce a variable degree of immediate tumor destruction that leads to antigen presentation and the induction of tumor-directed T-cell responses. Preferably, in vivo induction of ADCC will lead to tumor-directed T-cell responses and host-derived antibody responses.

"Complement-dependent cytotoxicity" or "CDC" is another cell-killing method that can be directed by antibodies. IgM is the most effective isotype for complement activation. IgG1 and IgG3 are also both very effective at directing CDC via the classical complement-activation pathway. Preferably, in this cascade, the formation of antigen-antibody complexes results in the uncloaking of multiple C1q binding sites in close proximity on the CH2 domains of participating antibody molecules such as IgG molecules (C1q is one of three subcomponents of complement C1). Preferably these uncloaked C1q binding sites convert the previously low-affinity C1q-IgG interaction to one of high avidity, which triggers a cascade of events involving a series of other complement proteins and leads to the proteolytic release of the effector-cell chemotactic/activating agents C3a and C5a. Preferably, the complement cascade ends in the formation of a membrane attack complex, which creates pores in the cell membrane that facilitate free passage of water and solutes into and out of the cell.

The term "toll-like receptor" or "TLR" relates to a class of proteins that play a key role in the innate immune system. They are single, membrane-spanning, non-catalytic receptors usually expressed in sentinel cells such as macrophages and dendritic cells, that recognize structurally conserved molecules derived from microbes. Once these microbes have breached physical barriers such as the skin or intestinal tract mucosa, they are recognized by TLRs, which activate immune cell responses.

In one embodiment of the invention, a nucleic acid such as RNA that codes for an antigen is administered to a subject. An antigenic translation product of the nucleic acid may be formed in cells of the subject and the product may be displayed to the immune system for stimulation of an immune response.

Alternatively, the present invention envisions embodiments wherein a nucleic acid expressing an antigen recited herein is introduced into cells such as antigen-presenting cells ex vivo, e.g. antigen-presenting cells taken from a patient, and the cells, optionally clonally propagated ex vivo, are transplanted back into the same patient. Transfected cells may be reintroduced into the patient using any means known in the art, preferably in sterile form by intravenous, intracavitary, intraperitoneal or intratumor administration.

The term "nucleic acid", as used herein, is intended to include deoxyribonucleic acid (DNA) or ribonucleic acid (RNA) such as cDNA, mRNA, recombinantly produced and chemically synthesized molecules. A nucleic acid may be single-stranded or double-stranded. According to the invention, RNA includes in vitro transcribed RNA (IVT RNA) or synthetic RNA.

According to the invention, a nucleic acid is preferably an isolated nucleic acid. Furthermore, the nucleic acids described herein may be recombinant molecules.

The term "isolated nucleic acid" means, according to the invention, that the nucleic acid (i) was amplified in vitro, for example via polymerase chain reaction (PCR), (ii) was produced recombinantly by cloning, (iii) was purified, for example, by cleavage and separation by gel electrophoresis, or (iv) was synthesized, for example, by chemical synthesis. A nucleic can be employed for introduction into, i.e. transfection of, cells, for example, in the form of RNA which can be prepared by in vitro transcription from a DNA template. The RNA can moreover be modified before application by stabilizing sequences, capping, and polyadenylation.

In the context of the present invention, the term "DNA" relates to a molecule which comprises deoxyribonucleotide residues and preferably is entirely or substantially composed of deoxyribonucleotide residues. "Deoxyribonucleotide" relates to a nucleotide which lacks a hydroxyl group at the 2'-position of a β-D-ribofuranosyl group. The term "DNA" comprises isolated DNA such as partially or completely purified DNA, essentially pure DNA, synthetic DNA, and recombinantly generated DNA and includes modified DNA which differs from naturally occurring DNA by addition, deletion, substitution and/or alteration of one or more nucleotides. Such alterations can include addition of non-nucleotide material, such as to the end(s) of a DNA or internally, for example at one or more nucleotides of the DNA. Nucleotides in DNA molecules can also comprise non-standard nucleotides, such as non-naturally occurring nucleotides or chemically synthesized nucleotides. These altered DNAs can be referred to as analogs or analogs of naturally-occurring DNA.

In the context of the present invention, the term "RNA" relates to a molecule which comprises ribonucleotide residues and preferably being entirely or substantially composed of ribonucleotide residues. "Ribonucleotide" relates to a nucleotide with a hydroxyl group at the 2'-position of a 13-D-ribofuranosyl group. The term includes double stranded RNA, single stranded RNA, isolated RNA such as partially or completely purified RNA, essentially pure RNA, synthetic RNA, recombinantly produced RNA, as well as modified RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA. According to the present invention, the term "RNA" includes and preferably relates to "mRNA" which means "messenger RNA" and relates to a transcript which may be produced using DNA as template and encodes a peptide or protein. mRNA typically comprises a 5' non translated region (5'-UTR), a protein or peptide coding region and a 3' non translated region (3'-UTR). mRNA has a limited halftime in cells and in vitro. Preferably, mRNA is produced by in vitro transcription using a DNA template. In one embodiment of the invention, the RNA is obtained by in vitro transcription or chemical synthesis. The in vitro transcription methodology is known to the skilled person. For example, there is a variety of in vitro transcription kits commercially available.

According to the invention, the stability and translation efficiency of RNA may be modified as required. For example, RNA may be stabilized and its translation increased by one or more modifications having a stabilizing effects and/or increasing translation efficiency of RNA. In order to increase expression of the RNA used according to the present invention, it may be modified within the coding region, i.e. the sequence encoding the expressed peptide or protein, preferably without altering the sequence of the expressed peptide or protein, so as to increase the GC-content to increase mRNA stability and to perform a codon optimization and, thus, enhance translation in cells.

The term "modification" in the context of the RNA used in the present invention includes any modification of an RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified ribonucleotides in order to increase its stability and/or decrease cytotoxicity. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap ($m^7G$). In the context of the present invention, the term "5 '-cap" includes a 5'-cap analog that resembles the RNA cap structure and is modified to possess the ability to stabilize RNA and/or enhance translation of RNA if attached thereto, preferably in vivo and/or in a cell.

The RNA may comprise further modifications. For example, a further modification of the RNA used in the present invention may be an extension or truncation of the naturally occurring poly(A) tail or an alteration of the 5'- or 3'-untranslated regions (UTR) such as introduction of a UTR which is not related to the coding region of said RNA, for example, the exchange of the existing 3'-UTR with or the insertion of one or more, preferably two copies of a 3'-UTR derived from a globin gene, such as alpha2-globin, alpha1-globin, beta-globin, preferably beta-globin, more preferably human beta-globin.

RNA having an unmasked poly-A sequence is translated more efficiently than RNA having a masked poly-A sequence. The term "poly(A) tail" or "poly-A sequence" relates to a sequence of adenyl (A) residues which typically is located on the 3'-end of a RNA molecule and "unmasked poly-A sequence" means that the poly-A sequence at the 3' end of an RNA molecule ends with an A of the poly-A sequence and is not followed by nucleotides other than A located at the 3" end, i.e. downstream, of the poly-A sequence. Furthermore, a long poly-A sequence of about 120 base pairs results in an optimal transcript stability and translation efficiency of RNA.

Therefore, in order to increase stability and/or expression of the RNA used according to the present invention, it may be modified so as to be present in conjunction with a poly-A sequence, preferably having a length of 10 to 500, more preferably 30 to 300, even more preferably 65 to 200 and especially 100 to 150 adenosine residues. In an especially preferred embodiment the poly-A sequence has a length of approximately 120 adenosine residues. To further increase stability and/or expression of the RNA used according to the invention, the poly-A sequence can be unmasked.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

Of course, if according to the present invention it is desired to decrease stability and/or translation efficiency of RNA, it is possible to modify RNA so as to interfere with the function of elements as described above increasing the stability and/or translation efficiency of RNA.

The nucleic acids described herein may be comprised in a vector which can be used to deliver a nucleic acid to the interior of a cell. The term "vector" as used herein includes any vectors known to the skilled person including plasmid vectors, cosmid vectors, phage vectors such as lambda phage, viral vectors such as adenoviral or baculoviral vectors, retro- or lentiviral vectors, transposons or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

Those of skill in the art of molecular biology generally know how to use promoters, enhancers, and cell type combinations for protein expression. The promoters employed may be constitutive, tissue-specific, inducible, and/or useful under the appropriate conditions to direct high level expression of the introduced nucleic acid segment. The promoter may be heterologous or endogenous. Constitutive promoter sequences which may be used according to the invention, include, but are not limited to the immediate early cytomegalovirus (CMV) promoter sequence, the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue. Tissue specific promoters are well known in the art and include, but are not limited to, the HER-2 promoter and the PSA associated promoter sequences.

Nucleic acids can be transferred into a host cell by physical, chemical or biological means.

Physical methods for introducing a nucleic acid into a host cell include calcium phosphate precipitation, lipofection, particle bombardment, microinjection, electroporation, and the like.

Biological methods for introducing a nucleic acid of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like.

Chemical means for introducing a nucleic acid into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

"Encoding" refers to the inherent property of specific sequences of nucleotides in a nucleic acid to serve as templates for synthesis of other polymers and macromolecules in biological processes having either a defined sequence of nucleotides or a defined sequence of amino acids. Thus, a nucleic acid encodes a protein if expression (translation and optionally transcription) of the nucleic acid produces the protein in a cell or other biological system.

The term "expression" is used according to the invention in its most general meaning and comprises the production of RNA and/or peptides or polypeptides, e.g. by transcription and/or translation. With respect to RNA, the term "expression" or "translation" relates in particular to the production of peptides or polypeptides. It also comprises partial expression of nucleic acids. Moreover, expression can be transient or stable.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". According to the present invention, the RNA used in the present invention preferably is in vitro transcribed RNA (IVT-RNA) and may be obtained by in vitro transcription of an appropriate DNA template. The promoter for controlling transcription can be any promoter for any RNA polymerase. Particular examples of RNA polymerases are the T7, T3, and SP6 RNA polymerases. Preferably, the in vitro transcription according to the invention is controlled by a T7 or SP6 promoter. A DNA template for in vitro transcription may be obtained by cloning of a nucleic acid, in particular cDNA, and introducing it into an appropriate vector for in vitro transcription. The cDNA may be obtained by reverse transcription of RNA.

The term "translation" according to the invention relates to the process in the ribosomes of a cell by which a strand of messenger RNA directs the assembly of a sequence of amino acids to make a peptide or polypeptide.

Expression control sequences or regulatory sequences, which according to the invention may be linked functionally with a nucleic acid, can be homologous or heterologous with respect to the nucleic acid. A coding sequence and a regulatory sequence are linked together "functionally" if they are bound together covalently, so that the transcription or translation of the coding sequence is under the control or under the influence of the regulatory sequence. If the coding sequence is to be translated into a functional protein, with functional linkage of a regulatory sequence with the coding sequence, induction of the regulatory sequence leads to a transcription of the coding sequence, without causing a reading frame shift in the coding sequence or inability of the coding sequence to be translated into the desired protein or peptide.

The term "expression control sequence" or "regulatory sequence" comprises, according to the invention, promoters, ribosome-binding sequences and other control elements, which control the transcription of a nucleic acid or the translation of the derived RNA. In certain embodiments of the invention, the regulatory sequences can be controlled. The precise structure of regulatory sequences can vary depending on the species or depending on the cell type, but generally comprises 5'-untranscribed and 5'- and 3'-untranslated sequences, which are involved in the initiation of transcription or translation, such as TATA-box, capping-sequence, CAAT-sequence and the like. In particular, 5'-untranscribed regulatory sequences comprise a promoter region that includes a promoter sequence for transcriptional control of the functionally bound gene. Regulatory sequences can also comprise enhancer sequences or upstream activator sequences.

According to the invention it is preferred that a nucleic acid such as RNA encoding a peptide or protein once taken up by or introduced, i.e. transfected or transduced, into a cell which cell may be present in vitro or in a subject results in expression of said peptide or protein. The cell may express the encoded peptide or protein intracellularly (e.g. in the cytoplasm and/or in the nucleus), may secrete the encoded peptide or protein, or may express it on the surface.

According to the invention, terms such as "nucleic acid expressing" and "nucleic acid encoding" or similar terms are used interchangeably herein and with respect to a particular peptide or polypeptide mean that the nucleic acid, if present in the appropriate environment, preferably within a cell, can be expressed to produce said peptide or polypeptide.

Terms such as "transferring", "introducing", "transfecting" or "transducing" are used interchangeably herein and relate to the introduction of nucleic acids, in particular exogenous or heterologous nucleic acids, such as RNA into a cell. According to the present invention, the cell can be present in vitro or in vivo, e.g. the cell can form part of an organ, a tissue and/or an organism. According to the invention, transfection can be transient or stable. For some applications of transfection, it is sufficient if the transfected genetic material is only transiently expressed. Since the nucleic acid introduced in the transfection process is usually not integrated into the nuclear genome, the foreign nucleic acid will be diluted through mitosis or degraded. Cell lines allowing episomal amplification of nucleic acids greatly reduce the rate of dilution. If it is desired that the transfected nucleic acid actually remains in the genome of the cell and its daughter cells, a stable transfection must occur. RNA can be transfected into cells to transiently express its coded protein.

"Fragment" with respect to a nucleic acid sequence relates to a part of the nucleic acid sequence, i.e. a sequence which represents the nucleic acid sequence shortened at the 5'- and/or 3'-end(s). A fragment of a nucleic acid sequence preferably comprises at least 6, in particular at least 8, at least 12, at least 15, at least 20, at least 30, at least 50, or at least 100 consecutive nucleotides of the nucleic acid sequence.

The present invention also includes "variants" of the nucleic acids or nucleic acid sequences such as immunostimulatory RNA molecules described herein.

According to the invention, nucleic acid variants include single or multiple nucleotide deletions, additions, mutations and/or insertions in comparison with the reference nucleic acid. Deletions include removal of one or more nucleotides from the reference nucleic acid. Addition variants comprise 5'- and/or 3'-terminal fusions of one or more nucleotides, such as 1, 2, 3, 5, 10, 20, 30, 50, or more nucleotides. Mutations can include but are not limited to substitutions, wherein at least one nucleotide in the sequence is removed and another nucleotide is inserted in its place (such as transversions and transitions), abasic sites, crosslinked sites, and chemically altered or modified bases. Insertions include the addition of at least one nucleotide into the reference nucleic acid.

Preferably the degree of identity between a given nucleic acid sequence and a nucleic acid sequence which is a variant of said given nucleic acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of identity is given preferably for a nucleic acid region which is at least about 10%, at least about 20%, at least about 30%, at least about 40%, at least about 50%, at least about 60%, at least about 70%, at least about 80%, at least about 90% or about 100% of the entire length of the reference nucleic acid sequence. For example, if the reference nucleic acid sequence consists of 200 nucleotides, the degree of identity is given preferably for at least about 20, at least about 40, at least about 60, at least about 80, at least about 100, at least about 120, at least about 140, at least about 160, at least about 180, or about 200 nucleotides, preferably continuous nucleotides. The degree of identity is given preferably for a segment of at least 80, at least 100, at least 120, at least 150, at least 180, at least 200 or at least 250 nucleotides. In preferred embodiments, the degree of identity is given for the entire length of the reference nucleic acid sequence.

"Sequence identity" between two nucleic acid sequences indicates the percentage of nucleotides that are identical between the sequences.

The term "% identity" is intended to refer, in particular, to a percentage of nucleotides which are identical in an optimal alignment between two sequences to be compared, with said percentage being purely statistical, and the differences between the two sequences may be randomly distributed over the entire length of the sequence and the sequence to be compared may comprise additions or deletions in comparison with the reference sequence, in order to obtain optimal alignment between two sequences. Comparisons of two sequences are usually carried out by comparing said sequences, after optimal alignment, with respect to a segment or "window of comparison", in order to identify local regions of corresponding sequences. The optimal alignment for a comparison may be carried out manually or with the aid of the local homology algorithm by Smith and Waterman, 1981, Ads App. Math. 2, 482, with the aid of the local homology algorithm by Neddleman and Wunsch, 1970, J. Mol. Biol. 48, 443, and with the aid of the similarity search algorithm by Pearson and Lipman, 1988, Proc. Natl Acad. Sci. USA 85, 2444 or with the aid of computer programs using said algorithms (GAP, BESTFIT, FASTA, BLAST P, BLAST N and TFASTA in Wisconsin Genetics Software Package, Genetics Computer Group, 575 Science Drive, Madison, Wis.).

Percentage identity is obtained by determining the number of identical positions in which the sequences to be compared correspond, dividing this number by the number of positions compared and multiplying this result by 100.

Variants of specific nucleic acid sequences or nucleic acid sequences having a particular degree of identity to specific nucleic acid sequences preferably have at least one functional property of said specific sequences and preferably are functionally equivalent to said specific sequences, e.g. nucleic acid sequences exhibiting properties identical or similar to those of the specific nucleic acid sequences.

One important property includes the ability to act as adjuvant or immunostimulatory agent, in particular when administered in conjunction with an antigen or nucleic acid encoding an antigen.

According to the present invention, the term "peptide" refers to substances comprising two or more, preferably 3 or more, preferably 4 or more, preferably 6 or more, preferably 8 or more, preferably 10 or more, preferably 13 or more, preferably 16 more, preferably 21 or more and up to preferably 8, 10, 20, 30, 40 or 50, in particular 100 amino acids joined covalently by peptide bonds.

The term "protein" refers to large peptides, i.e. polypeptides, preferably to peptides with more than 100 amino acid residues, but in general the terms "peptide", "polypeptide" and "protein" are synonyms and are used interchangeably herein.

The present invention also includes "variants" of the peptides, proteins, or amino acid sequences described herein.

For the purposes of the present invention, "variants" of an amino acid sequence comprise amino acid insertion variants, amino acid addition variants, amino acid deletion variants and/or amino acid substitution variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein. Amino acid deletion variants that comprise the deletion at the N-terminal and/or C-terminal end of the protein are also called N-terminal and/or C-terminal truncation variants.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. The degree of similarity or identity is given preferably for a segment of at least 80, at least 100, at least 120, at least 150, at least 180, at least 200 or at least 250 amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "% identity" is intended to refer, in particular, to a percentage of amino acid residues which are identical in an optimal alignment between two sequences to be compared, with said percentage being purely statistical, and the differences between the two sequences may be randomly distributed over the entire length of the sequence and the sequence to be compared may comprise additions or deletions in comparison with the reference sequence, in order to obtain optimal alignment between two sequences. Comparisons of two sequences are usually carried out by comparing said sequences, after optimal alignment, with respect to a segment or "window of comparison", in order to identify local regions of corresponding sequences. The optimal alignment for a comparison may be carried out manually or with the aid of the local homology algorithm by Smith and Waterman, 1981, Ads App. Math. 2, 482, with the aid of the local homology algorithm by Neddleman and Wunsch, 1970, J. Mol. Biol. 48, 443, and with the aid of the similarity search algorithm by Pearson and Lipman, 1988, Proc. Natl Acad. Sci. USA 85, 2444 or with the aid of computer programs using said algorithms (GAP, BESTFIT, FASTA, BLAST P, BLAST N and TFASTA in Wisconsin Genetics Software Package, Genetics Computer Group, 575 Science Drive, Madison, Wis.).

Percentage identity is obtained by determining the number of identical positions in which the sequences to be compared correspond, dividing this number by the number of positions compared and multiplying this result by 100.

Homologous amino acid sequences exhibit according to the invention at least 40%, in particular at least 50%, at least 60%, at least 70%, at least 80%, at least 90% and preferably at least 95%, at least 98 or at least 99% identity of the amino acid residues.

According to the invention, a variant, fragment, part or portion of an amino acid sequence, peptide or protein preferably has a functional property of the amino acid sequence, peptide or protein, respectively, from which it has been derived, i.e. it is functionally equivalent. In one embodiment, a variant, fragment, part or portion of an amino acid sequence, peptide or protein is immunologically equivalent to the amino acid sequence, peptide or protein, respectively, from which it has been derived. In one embodiment, the functional property is an immunological property.

The invention includes derivatives of the peptides or proteins described herein which are comprised by the terms "peptide" and "protein". According to the invention, "derivatives" of proteins and peptides are modified forms of proteins and peptides. Such modifications include any chemical modification and comprise single or multiple substitutions, deletions and/or additions of any molecules associated with the protein or peptide, such as carbohydrates, lipids and/or proteins or peptides. In one embodiment, "derivatives" of proteins or peptides include those modified analogs resulting from glycosylation, acetylation, phosphorylation, amidation, palmitoylation, myristoylation, isoprenylation, lipidation, alkylation, derivatization, introduction of protective/blocking groups, proteolytic cleavage or binding to an antibody or to another cellular ligand. The term "derivative" also extends to all functional chemical equivalents of said proteins and peptides. Preferably, a modified peptide has increased stability and/or increased immunogenicity.

The term "derived" means according to the invention that a particular entity, in particular a particular sequence, is present in the object from which it is derived, in particular an organism or molecule. In the case of amino acid or nucleic acid sequences, especially particular sequence regions, "derived" in particular means that the relevant amino acid sequence or nucleic acid sequence is derived from an amino acid sequence or nucleic acid sequence in which it is present.

The term "cell" or "host cell" preferably is an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transformed or transfected with an exogenous nucleic acid. The term "cell" includes according to the invention prokaryotic cells (e.g., *E. coli*) or eukaryotic cells (e.g., dendritic cells, B cells, CHO cells, COS cells, K562 cells, HEK293 cells, HELA cells, yeast cells, and insect cells). The exogenous nucleic acid may be found inside the cell (i) freely dispersed as such, (ii) incorporated in a recombinant vector, or (iii) integrated into the host cell genome or mitochondrial DNA. Mammalian cells are particularly preferred, such as cells from humans, mice, hamsters, pigs, goats, and primates. The cells may be derived from a large number of tissue types and include primary cells and cell lines.

A cell which comprises a nucleic acid, e.g. which has been transfected with a nucleic acid, preferably expresses the peptide or protein encoded by the nucleic acid.

The term "expansion" refers to a process wherein a specific entity is multiplied. In one embodiment of the present invention, the term is used in the context of an immunological response in which lymphocytes are stimulated by an antigen, proliferate, and the specific lymphocyte recognizing said antigen is amplified. Preferably, clonal expansion leads to differentiation of the lymphocytes.

"Isolated" as used herein, is intended to refer to a molecule which is substantially free of other molecules such as other cellular material.

The term "recombinant" in the context of the present invention means "made through genetic engineering". Preferably, a "recombinant object" such as a recombinant cell or nucleic acid in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

Terms such as "reducing", "inhibiting" or "decreasing" relate to the ability to cause an overall decrease, preferably of 5% or greater, 10% or greater, 20% or greater, more preferably of 50% or greater, and most preferably of 75% or greater, in the level. These terms include a complete or essentially complete inhibition, i.e. a reduction to zero or essentially to zero.

Terms such as "increasing", "enhancing", "promoting", or "stimulating" relate to the ability to cause an overall increase, preferably of 5% or greater, 10% or greater, 20% or greater, 50% or greater, 75% or greater, 100% or greater, 200% or greater, or 500% or greater, in the level. These terms may relate to an increase, enhancement, promotion, or stimulation from zero or a non-measurable or non-detectable level to a level of more than zero or a level which is measurable or detectable. Alternatively, these terms may also mean that there was a certain level before an increase, enhancement, promotion, or stimulation and after the increase, enhancement, promotion, or stimulation the level is higher.

The agents and compositions described herein can be used to treat a subject with a disease, e.g., a disease characterized by the presence of an antigen or diseased cells expressing an antigen. Particularly preferred diseases are cancer diseases. Agents and compositions described herein may also be used for immunization or vaccination to prevent a disease described herein.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality. According to the invention, the term "disease" includes infectious diseases and cancer diseases. Any reference herein to cancer or particular forms of cancer also includes cancer metastasis thereof.

A disease to be treated according to the invention is preferably a disease involving an antigen or being associated with an antigen.

The term "disease associated with an antigen" or "disease involving an antigen" refers to any disease which implicates an antigen, e.g. a disease which is characterized by the presence of an antigen or cells expressing an antigen. The disease involving an antigen can be an infectious disease, or a cancer disease or simply cancer. As mentioned above, the antigen may be a disease-associated antigen, such as a tumor-associated antigen, a viral antigen, or a bacterial antigen.

The term "infectious disease" refers to any disease which can be transmitted from individual to individual or from organism to organism, and is caused by a microbial agent. Infectious diseases are known in the art and include, for example, a viral disease, a bacterial disease, or a parasitic disease, which diseases are caused by a virus, a bacterium, and a parasite, respectively. In this regard, the infectious disease can be, for example, hepatitis, sexually transmitted diseases (e.g. chlamydia or gonorrhea), tuberculosis, HIV/ acquired immune deficiency syndrome (AIDS), diphtheria, hepatitis B, hepatitis C, cholera, severe acute respiratory syndrome (SARS), the bird flu, and influenza.

The terms "cancer disease" or "cancer" refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer, lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the invention also comprises cancer metastases. Preferably, a "cancer disease" is characterized by cells expressing a tumor antigen and a cancer cell expresses a tumor antigen.

In one embodiment, a cancer disease is a malignant disease which is characterized by the properties of anaplasia, invasiveness, and metastasis. A malignant tumor may be contrasted with a non-cancerous benign tumor in that a malignancy is not self-limited in its growth, is capable of invading into adjacent tissues, and may be capable of spreading to distant tissues (metastasizing), while a benign tumor has none of those properties.

According to the invention, the term "tumor" or "tumor disease" refers to an abnormal growth of cells (called neoplastic cells, tumorigenous cells or tumor cells) preferably forming a swelling or lesion. By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system. In one embodiment, the term "metastasis" according to the invention relates to lymph node metastasis.

A relapse or recurrence occurs when a person is affected again by a condition that affected them in the past. For example, if a patient has suffered from a tumor disease, has received a successful treatment of said disease and again develops said disease said newly developed disease may be considered as relapse or recurrence. However, according to the invention, a relapse or recurrence of a tumor disease may but does not necessarily occur at the site of the original tumor disease. Thus, for example, if a patient has suffered from ovarian tumor and has received a successful treatment a relapse or recurrence may be the occurrence of an ovarian tumor or the occurrence of a tumor at a site different to ovary. A relapse or recurrence of a tumor also includes situations wherein a tumor occurs at a site different to the site of the original tumor as well as at the site of the original tumor. Preferably, the original tumor for which the patient has received a treatment is a primary tumor and the tumor at a site different to the site of the original tumor is a secondary or metastatic tumor.

The term "treatment" or "therapeutic treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual, in particular an individual being at risk for the disease. The terms "prophylactic treatment" or "preventive treatment" are used herein interchangeably.

By "being at risk" is meant a subject, i.e. a patient, that is identified as having a higher than normal chance of developing a disease, in particular cancer, compared to the general population. In addition, a subject who has had, or who currently has, a disease, in particular cancer is a subject who has an increased risk for developing a disease, as such a subject may continue to develop a disease. Subjects who currently have, or who have had, a cancer also have an increased risk for cancer metastases.

The term "immunotherapy" relates to the treatment of a disease or condition by inducing, or enhancing an immune response. The term "immunotherapy" includes antigen immunization or antigen vaccination, or tumor immunization or tumor vaccination.

The terms "immunization" or "vaccination" describe the process of providing an antigen to an individual with the purpose of inducing an immune response, for example, for therapeutic or prophylactic reasons.

The term "in vivo" relates to the situation in a subject.

The term "individual" or "subject" relates to vertebrates, particularly mammals. For example, mammals in the context of the present invention are humans, non-human primates, domesticated mammals such as dogs, cats, sheep, cattle, goats, pigs, horses etc., laboratory animals such as mice, rats, rabbits, guinea pigs, etc. as well as animals in captivity such as animals of zoos. The term "subject" also relates to non-mammalian vertebrates such as birds (particularly domesticated birds such as chicken, ducks, geese, turkeys) and to fish (particularly farmed fish, e.g. salmon or catfish). The term "animal" as used herein also includes humans. Preferably, the term "patient" relates to a diseased individual.

The term "autologous" is used to describe anything that is derived from the same subject. For example, "autologous transplant" refers to a transplant of tissue or organs derived from the same subject. Such procedures are advantageous because they overcome the immunological barrier which otherwise results in rejection.

The term "allogeneic" is used to describe anything that is derived from different individuals of the same species. Two or more individuals are said to be allogeneic to one another when the genes at one or more loci are not identical.

The term "syngeneic" is used to describe anything that is derived from individuals or tissues having identical genotypes, i.e., identical twins or animals of the same inbred strain, or their tissues.

The term "heterologous" is used to describe something consisting of multiple different elements. As an example, the transfer of one individual's bone marrow into a different individual constitutes a heterologous transplant. A heterologous gene is a gene derived from a source other than the subject.

The agents described herein may be administered in the form of any suitable pharmaceutical composition. The term "pharmaceutical composition" relates to a formulation comprising a therapeutically effective agent or a salt thereof, preferably together with pharmaceutical excipients such as buffers, preservatives and tonicity modifiers. Said pharmaceutical composition is useful for treating or preventing a disease or disorder by administration of said pharmaceutical composition to an individual. A pharmaceutical composition is also known in the art as a pharmaceutical formulation. The pharmaceutical composition can be administered locally or systemically.

The term "systemic administration" refers to the administration of a therapeutically effective agent such that the agent becomes widely distributed in the body of an individual in significant amounts and develops a biological effect. According to the present invention, it is preferred that administration is by parenteral administration.

The term "parenteral administration" refers to administration of a therapeutically effective agent such that the agent does not pass the intestine. The term "parenteral administration" includes intravenous administration, subcutaneous administration, intradermal administration or intraarterial administration but is not limited thereto.

In particular embodiments, an antigen or a nucleic acid encoding an antigen is administered before, simultaneously with and/or after administration of immunostimulatory RNA molecules described herein. The antigen or nucleic acid encoding an antigen and immunostimulatory RNA molecules can be present in a common composition, i.e. mixed together. Moreover, embodiments are also envisaged according to the invention in which the antigen or nucleic acid encoding an antigen and immunostimulatory RNA molecules are present together, but not in the same composition. Said embodiments relate in particular to kits with at least two containers, where one container contains a composition comprising the antigen or nucleic acid encoding an antigen, and another container contains a composition comprising the immunostimulatory RNA molecules.

The pharmaceutical compositions of the present invention may comprise adjuvants other than the immunostimulatory RNA molecules described herein. Such adjuvants comprise a heterogeneous group of compounds such as oil emulsions (e.g., Freund's adjuvants), mineral compounds (such as alum), bacterial products (such as *Bordetella pertussis* toxin), or immune-stimulating complexes. Examples for adjuvants include saponins, incomplete Freund's adjuvants, complete Freund's adjuvants, tocopherol or alum, but are not limited thereto.

The pharmaceutical composition according to the present invention is generally applied in a "pharmaceutically effective amount" and in "a pharmaceutically acceptable preparation".

The term "pharmaceutically effective amount" refers to the amount which achieves a desired reaction or a desired effect alone or together with further doses. In the case of the treatment of a particular disease, the desired reaction preferably relates to inhibition of the course of the disease. This comprises slowing down the progress of the disease and, in particular, interrupting or reversing the progress of the disease. The desired reaction in a treatment of a disease may also be delay of the onset or a prevention of the onset of said disease or said condition. An effective amount of the compositions described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the compositions described herein may depend on various of such parameters. In the case that a reaction in a patient is insufficient with an initial dose, higher doses (or effectively higher doses achieved by a different, more localized route of administration) may be used.

The term "pharmaceutically acceptable" refers to the non-toxicity of a material which does not interact with the action of the active component of the pharmaceutical composition.

The pharmaceutical compositions of the present invention may contain salts, buffers, preserving agents, carriers and optionally other therapeutic agents. Preferably, the pharmaceutical compositions of the present invention comprise one or more pharmaceutically acceptable carriers, diluents and/or excipients.

The term "excipient" is intended to indicate all substances in a pharmaceutical composition which are not active ingredients such as binders, lubricants, thickeners, surface active agents, preservatives, emulsifiers, buffers, flavoring agents, or colorants.

The term "diluent" relates a diluting and/or thinning agent. Moreover, the term "diluent" includes any one or more of fluid, liquid or solid suspension and/or mixing media.

The term "carrier" relates to one or more compatible solid or liquid fillers or diluents, which are suitable for an administration to a human. The term "carrier" relates to a natural or synthetic organic or inorganic component which is combined with an active component in order to facilitate the application of the active component. Preferably, carrier components are sterile liquids such as water or oils, including those which are derived from mineral oil, animals, or plants, such as peanut oil, soy bean oil, sesame oil, sunflower oil, etc. Salt solutions and aqueous dextrose and glycerin solutions may also be used as aqueous carrier compounds.

Pharmaceutically acceptable carriers or diluents for therapeutic use are well known in the pharmaceutical art, and are described, for example, in Remington's Pharmaceutical Sciences, Mack Publishing Co. (A. R Gennaro edit. 1985). Examples of suitable carriers include, for example, magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Examples of suitable diluents include ethanol, glycerol and water.

Pharmaceutical carriers, excipients or diluents can be selected with regard to the intended route of administration and standard pharmaceutical practice. The pharmaceutical compositions of the present invention may comprise as, or in addition to, the carrier(s), excipient(s) or diluent(s) any suitable binder(s), lubricant(s), suspending agent(s), coating agent(s), and/or solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

In one embodiment, the composition is an aqueous composition. The aqueous composition may optionally comprise solutes, e.g. salts. In one embodiment, the composition is in the form of a freeze-dried composition. A freeze-dried composition is obtainable by freeze-drying a respective aqueous composition.

The agents and compositions provided herein may be used alone or in combination with other therapeutic regimens such as surgery, irradiation, chemotherapy and/or bone marrow transplantation (autologous, syngeneic, allogeneic or unrelated).

The present invention is further illustrated by the following examples which are not be construed as limiting the scope of the invention.

EXAMPLES

The techniques and methods used herein are described herein or carried out in a manner known per se and as described, for example, in Sambrook et al., Molecular Cloning: A Laboratory Manual, 2nd Edition (1989) Cold Spring Harbor Laboratory Press, Cold Spring Harbor, N.Y. All methods including the use of kits and reagents are carried out according to the manufacturers' information unless specifically indicated.

Materials and Methods

Control Adjuvants and Synthetic RNA Oligonucleotides

The TLR3 agonist Poly (I:C), the TLR7/8 ligand CL097, a derivative of the imidazoquinoline compound R848, the human TLR8 agonist ssRNA40 complexed with cationic lipid (LyoVec), the human/murine TLR9 agonist type C CpG ODN2395 and the human TLR9 agonist type D CpG ODN2216 were purchased from Invivogen and were used as control adjuvants in various experiments. Bafilomycin A1 (Invivogen) was used as an endosomal acidification inhibitor to block TLR activation. Complete and incomplete Freund's adjuvant (CFA/IFA) was used for s.c. control immunizations according to the manufacturer's instructions (Sigma-Aldrich). The chemically synthesized isRNA NP71-Seq4 (Chem. Synth.) and Poly (A) RNA as control were purchased from Biomers.

Chimeric Hepatitis B Virus Core Antigen (HBcAg) Derived Virus-Like Particles (VLPs)

HBcAg-VLPs displaying a selected epitope (#A79) of the tumor-associated antigen (TAA) Claudin-6 (CLDN6) on their surface were generated as described in Klamp, T. et al.; Cancer Res 71(2), 1-12 (2011).

In Vitro Transcription and Purification of isRNAs

Plasmid templates for in vitro transcription (IVT) of isRNAs were based on the pST1-A120 vector described in Kuhn, A. et al.; Gene Ther 17(8), 961-971 (2010). The selected Influenza NP fragments were cloned between Spa and XhoI restriction sites using standard molecular biology methods. The resulting plasmids were linearized with Viol (Fermentas, ThermoFisher) and purified by magnetic separation using Dynabeads MyOne Carboxylic Acid (Invitrogen). The following IVT reaction was performed according to protocols described previously in Kreiter, S. et al.; Cancer Immunol Immunother 56, 1577-1587 (2007). Small scale purification of IVT RNAs was performed with silica-based membranes using the RNeasy Mini Kit (QIAGEN) and following manufacturer's instructions. For large scale purification of IVT RNAs, a FPLC-based method using a weak anion exchange column (HiTrap DEAE Sepharose FF, GE Healthcare) was applied (Easton, L E. et al., RNA 16(3), 647-653 (2010)).

Formulation of isRNAs

Depending on the use for in vitro or in vivo experiments, purified Influenza NP derived isRNAs were formulated with cationic lipids differing in their lipid/helper-lipid composition and surface charge (Kranz, L M. et al.; Nature 534, 396-401 (2016)). For securing an optimal cellular uptake in in vitro experiments, isRNAs were formulated with the liposomal composition F5, whereas the composition F12 was used for in vivo experiments. F12 formulations permitted a high serum stability of isRNAs and spleen targeting of isRNA-lipoplexes after i.v. administration.

Mice

Female Balb/cJRj and C57BL/6 mice were obtained from Janvier Laboratories (France). BDCA2-DTR transgenic mice bred on a C57BL/6 background express the simian diphtheria toxin receptor (DTR) specifically in plasmacytoid dendritic cells (pDCs) and were purchased from the Jackson Laboratory (USA). Mice were 6 to 10 weeks of age at the onset of experiments. All animals were maintained under pathogen-free conditions.

Isolation of Human PBMCs and pDCs

Human PBMCs were freshly isolated from blood of healthy male or female donors by Ficoll density gradient centrifugation as described in Lin, Z. et al.; Nature protocols 9, 1563-1577 (2014). Plasmacytoid dendritic cells (pDCs) were isolated from human PBMCs using MACS-separation technology and the CD304 MicroBead Kit (Miltenyi Biotec).

Isolation of Mouse Bone Marrow Cells, Splenocytes, pDCs and cDCs

Mouse bone marrow cells (BMCs) were harvested from murine femur and tibia using standard protocols. Erythrocytes were lysed by incubation for 5 min with 5 ml cold Red Blood Cell (RBC) lysis buffer (Sigma-Aldrich), followed by the addition of 20 ml 1×PBS (Gibco) to stop the lysis reaction. BMCs were pelleted by centrifugation and resuspended in cell culture medium. Mouse splenocytes were prepared as described in Kreiter, S. et al.; Cancer Immunol Immunother 56, 1577-1587 (2007). pDCs were isolated from splenocytes by MACS-separation using the mouse pDC isolation kit II (Miltenyi Biotec). Conventional DCs (cDCs; CD11c high, B220 low) were generated from mouse BMCs by cultivation for 6 days in the presence of 20 ng/ml GM-CSF and 20 ng/ml IL4 (both from Peprotech).

Cell Culture

Primary human and mouse cells were cultured in RPMI1640 supplemented with 10% (v/v) heat-inactivated FBS, 1% (v/v) non-essential amino acids (NEAA), 1% (v/v) sodium pyruvate and 0,5% (v/v) Penicillin/Streptomycin solution. Chinese Hamster Ovary (CHO) K1 cells stably transfected with human CLDN6 or human CLDN9 were obtained from TRON gGmbH (Mainz, Germany) and cultured in DMEM supplemented with 10% (v/v) heat-inactivated FBS, 1 mg/ml G418 and 0,5% (v/v) Penicillin/Streptomycin solution. Wildtype human embryonic kidney (HEK) 293 cells or HEK293 cells stably co-expressing human TLR3, TLR7 or TLR8 and an NF-κB-inducible luciferase reporter gene were obtained from (Invivogen) and cultured in DMEM supplemented with 10% (v/v) heat-inactivated FBS, 1% (v/v) NEAA, 1% (v/v) sodium pyruvate and 0,5% (v/v) Penicillin/Streptomycin solution. Depending on the HEK293 transfectant used, the medium was additionally supplemented with Blasticidin (10 μg/ml), Zeocin (100 μg/ml) or Geneticin (250 μg/ml), all from Invivogen. FBS was purchased from Biochrom and all other cell culture reagents from Gibco.

In Vitro Stimulation of Cells with isRNAs

Cell stimulation with isRNAs or controls was performed in triplicates in 96-well plates (Corning) with a total volume of 200 μl. Unless otherwise noted $5 \times 10^5$ cells per well were used and stimulated for 12-16 h at 37° C. and 5% $CO_2$ with F5-formulated isRNAs in a concentration of 0,167 μg/well or control reagents using concentrations as indicated in the examples.

Cytokine Detection

IFN-α and other selected cytokines were detected in the supernatants from human or mouse cells or in mouse blood serum using commercially available ELISA kits (PBL Assay Science) or the Bio-Plex system using Bio-Plex Pro Kit III and cytokine specific Bio-Plex coupled magnetic beads (BioRad) following the manufacturer's instructions.

In Vivo Stimulation and Immunization Experiments

For in vivo stimulation experiments, Balb/c mice were injected i.v. into the retrobulbar venous plexus with different amounts of F12-formulated isRNAs. Depending on the experimental setup, blood samples for serum preparation were collected at different time points after injection as indicated in the examples. Blood serum was prepared after clotting by centrifugation using standard protocols and was stored until further use at −20° C. Immunization experiments were performed by i.v. injection of 20 μg F12-formulated isRNAs mixed with 50 μg purified HBcAg-#A79 VLPs (total volume 100 μl) into the retrobulbar venous plexus. Unless otherwise indicated, three injections were applied with two weeks intervals and final blood samples were taken 10 days after the last immunization. Preparation of blood serum was performed as described before.

Flow Cytometry

Induction of specific antibodies against the native CLDN6 protein after immunization with adjuvanted or non-adjuvanted HBcAg-#A79 VLPs was analyzed by flow cytometry. $2 \times 10^5$ CHO-K1 CLDN6 or CLDN9 cells per well were incubated for 1 h at 4° C. with polyclonal mouse antiserum diluted 1:100 in FACS-buffer (lx PBS, 5% (v/v) FBS, 5 mM EDTA). After three wash steps, the cells were stained for 30 mM at 4° C. with an AlexaFluor 647-conjugated goat anti-mouse IgG (H+L) secondary antibody (ThermoFisher) diluted 1:600 in FACS-buffer. Unbound antibodies were removed by additional wash steps and viability was determined using 7-AAD (Sigma). Fluorescence signals of living cells were detected by a FACS Canto II system (BD Biosciences).

IFN-γ ELISpot Analysis $5 \times 10^5$ freshly isolated mouse splenocytes were incubated in a 96-well plate (Merck Millipore) coated with anti-IFN-γ monoclonal antibody (10 μg/ml AN18, Mabtech) in the presence of 5 μg/ml #A79 or an irrelevant peptide (JPT Peptide Technologies) for 18 h at 37° C. Plates were sequentially incubated with biotin-conjugated secondary anti-IFN-γ monoclonal antibody (R4-6A2, Mabtech) and ExtrAvidin-Alkaline Phosphatase (Sigma-Aldrich) before cytokine secretion was detected by adding BCIP/NBT substrate (Sigma-Aldrich). For each group technical triplicates were performed. Plates were scanned and analyzed using an ImmunoSpot S5 Versa ELISpot analyzer, ImmunoCapture software 6.3 and ImmunoSpot software 5.0.3 (all Cellular Technology Ltd.).

Complement-Dependent Cytotoxicity (CDC) Assay

To analyze antibody-mediated cytocidal effector functions, complement-dependent cytotoxicity (CDC) assays were performed. CHO-K1 cells stably expressing human CLDN6 were incubated at a concentration of $1 \times 10^4$ cells/well in a 96-well plate (Corning Costar, Sigma-Aldrich) for 17.5 h at 37° C. and 7,5% $CO_2$. Subsequently the cells were incubated for 80 min in a total volume of 50 μl/well with 5 μl polyclonal mouse antiserum diluted in 32 μl culture medium and 13 μl human serum complement (Quidel Corporation) as a complement source. Mouse sera were derived from immunizations experiments with differently adjuvanted HBcAg-#A79 VLPs. A CLDN6 specific monoclonal antibody (Ganymed Pharmaceuticals AG, Mainz) in a concentration of 600 or 150 ng/ml was used as positive control. Heat-inactivated human serum complement served as negative control and for confirmation of a complement dependent antibody-mediated cytolytic effect. Untreated cells and cells lysed by Triton X-100 (Applichem) were used as benchmarks for 0% and 100% cell lysis respectively. Cell viability was analyzed with the XTT-assay based Cell proliferation Kit II (Roche Diagnostics) according to the manufacturer's instructions. Absorption at 480 nm was measured with Infinite M200 Pro reader (Tecan). The antibody-mediated cytolytic activity was calculated by the following equation:

$$\% \text{ cell lysis} = 100\% - ((\text{Signal antiserum} - \text{Signal } 100\% \text{ lysis}/\text{Signal untreated cells}) \times 100)$$

Mouse Immunoglobulin Isotyping ELISA

Streptavidin coupled 96-well plates (Nunc, ThermoFisher) were coated for 1 h with 100 ng/well of biotinylated #A79-peptide (JPT Peptide Technologies) followed by blocking of uncoated surfaces for 1 h with 300 μl/well 1×PBS, 2% (v/v) FBS and washing with 1×PBS, 0,05% Tween20 (Sigma-Aldrich) using a HydroSpeed plate washer (Tecan). Polyclonal mouse antisera were 10-fold serially diluted with 1× Casein blocking buffer (Sigma-Aldrich) and 100 μl of diluted sera were added per well and incubated for 1 h with slight agitation on a shaking platform (Infors). Bound antibodies were detected after additional wash steps by incubation for 1 h with 1:5000 diluted, HRP-conjugated, goat anti-mouse IgG isotype specific secondary antibodies (ThermoFisher) followed by final wash steps and the addition of TMB-substrate (Sigma-Aldrich) according to the manufacturer's instructions. Absorption at 450 nm was measured with an Infinite M200 Pro reader (Tecan). All steps were performed at room temperature and antiserum dilutions were measured in triplicates.

Statistical Analysis

All results are expressed as mean+/−standard error of the mean (SEM). Statistical calculations were performed using GraphPad Prism software version 6. T-test was used to compare two groups. For more than two groups one-way ANOVA was used. The difference between the groups were considered to be statistically significant at $P < 0.05$

Example 1: Sequential Fragmentation of Influenza Nucleoprotein (NP) Encoding RNA Enables the Identification and Selection of Small Immunostimulatory RNA Molecules (isRNAs) with Defined TLR Specificity and Cytokine Induction Profile Based on the observation that whole Influenza A genomic RNA induced high levels of interferon-alpha (IFN-α) in plasmacytoid dendritic cells (pDCs) by means of Toll-like receptor 7 (TLR7) stimulation (Diebold S S. et al.; Science 303(5663), 1529-1531 (2004), we selected the Influenza A nucleoprotein (NP) encoding RNA (1565 nt) as parental sequence to establish a sequential fragmentation strategy for the identification of defined, short immunostimulatory, single-stranded RNA molecules (isRNAs) responsible for the TLR7-dependent, IFN-α inducing activity. In contrast to whole Influenza A genomic RNA or other virus-derived whole RNA, short isRNA molecules inducing a defined cytokine induction profile and a specific adaptive immune response modulation can be produced in large scale under GMP-conditions by chemical synthesis or in vitro transcription, enabling their clinical application as adjuvants for recombinant protein based vaccines.

FIG. 1 shows a schematic overview of the applied sequential fragmentation strategy using Influenza NP encoding RNA (2-2-8, NP 1-1565) as starting sequence. Fragmentation was performed in iterative cycles and selected fragments were in vitro transcribed into RNA, purified and subsequently screened in vitro for their immunostimulatory activities and TLR specificity. Fragments with the highest TLR7 specificity, IFN-α induction capacity and a favorable cytokine induction profile were selected for further fragmentation cycles. The sequentially performed fragmentation strategy finally resulted in the identification and selection of small isRNAs with a length of 38-60 nucleotides designated as NP71-Seq4, Inno71-5A, NP71-Seq44 and NP71-Seq45.

Example 2: Synthesis of isRNAs by In Vitro Transcription, Composition and Sequence of isRNAs and Quality Control after Purification DNA sequences encoding selected Influenza NP fragments were cloned downstream of a bacteriophage T7 RNA polymerase promoter into plasmid pST1 using SpeI and XhoI restriction sites. XhoI linearized plasmids served as DNA template for the following in vitro transcription (IVT). IVT RNA synthesized by T7 RNA polymerase consisted of the selected Influenza NP RNA fragment flanked on both sides by short stretches derived from the pST1 plasmid template (FIG. 2A).

The sequences of the finally selected isRNAs NP71-Seq4, Inno71-5A, NP71-Seq44 and NP71-Seq45 and their overall size (in nucleotides, nt) including pST1 derived sequence parts are shown in FIG. 2B. Sequences derived from the pST1 template are underlined. The 5' end of the isRNAs is characterized by a triple guanosine representing the transcription start site of T7 RNA polymerase (Imburgio, D. et al.; Biochemistry 39(34), 10419-10430 (2000).

Figure 2D:
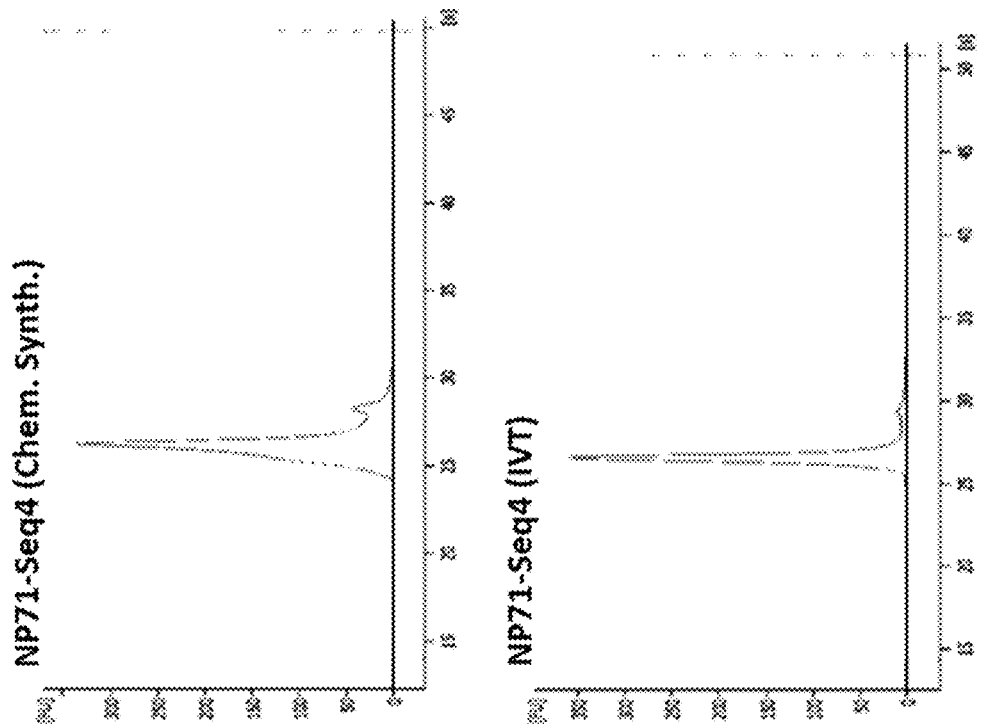
FIG. 2: Synthesis of isRNAs by in vitro transcription, composition and sequence of isRNAs and quality control after purification
Figure 2C:
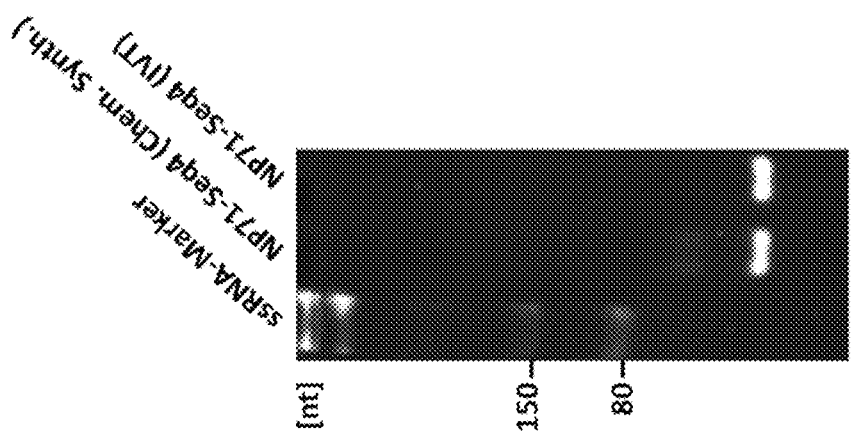

After purification with silica-based membranes or weak anion exchange columns, isRNAs were quality controlled by default using a variety of analytical methods. Size, homogeneity and integrity of purified isRNAs was analyzed by denaturing 10% polyacrylamide (PAA) gel electrophoresis (FIG. 2C) and by on chip capillary electrophoresis using the Bioanalyzer 2100 system (Agilent) (FIG. 2D). Results are exemplified for isRNA NP71-Seq4 that was either produced by IVT or fully chemically synthesized (Chem. Synth.). NP71-Seq4 (IVT) was characterized by a distinct single band of the expected size in PAA gels and a sharp peak in capillary electrophoresis indicating a homogeneous population without any signs of RNA integrity loss. In contrast, chemically synthesized NP71-Seq4 isRNA revealed a peak shoulder and a second minor peak after capillary electrophoresis pointing towards a more heterogeneous RNA population. Therefore, IVT RNA was used in all subsequent experiments.

Example 3: Formulated isRNAs Induce High Levels of IFN-α in Human PBMCs

Potential isRNA candidates derived by sequential fragmentation were screened after purification and quality control for their immunostimulatory capacity in cellular in vitro assays. A differential behavior in their capability to induce the lead cytokines IFN-α (strong induction) versus TNF-α (weak or absent induction) was defined as an initial key criterion for candidate selection and further fragmentation steps. The isRNA-mediated induction of the strong proinflammatory cytokine TNF-α should be minimized as it might lead to harmful systemic side effects and thereby negatively affecting the safety profile of the identified isRNAs when used as vaccine adjuvants.

Figure 3A:
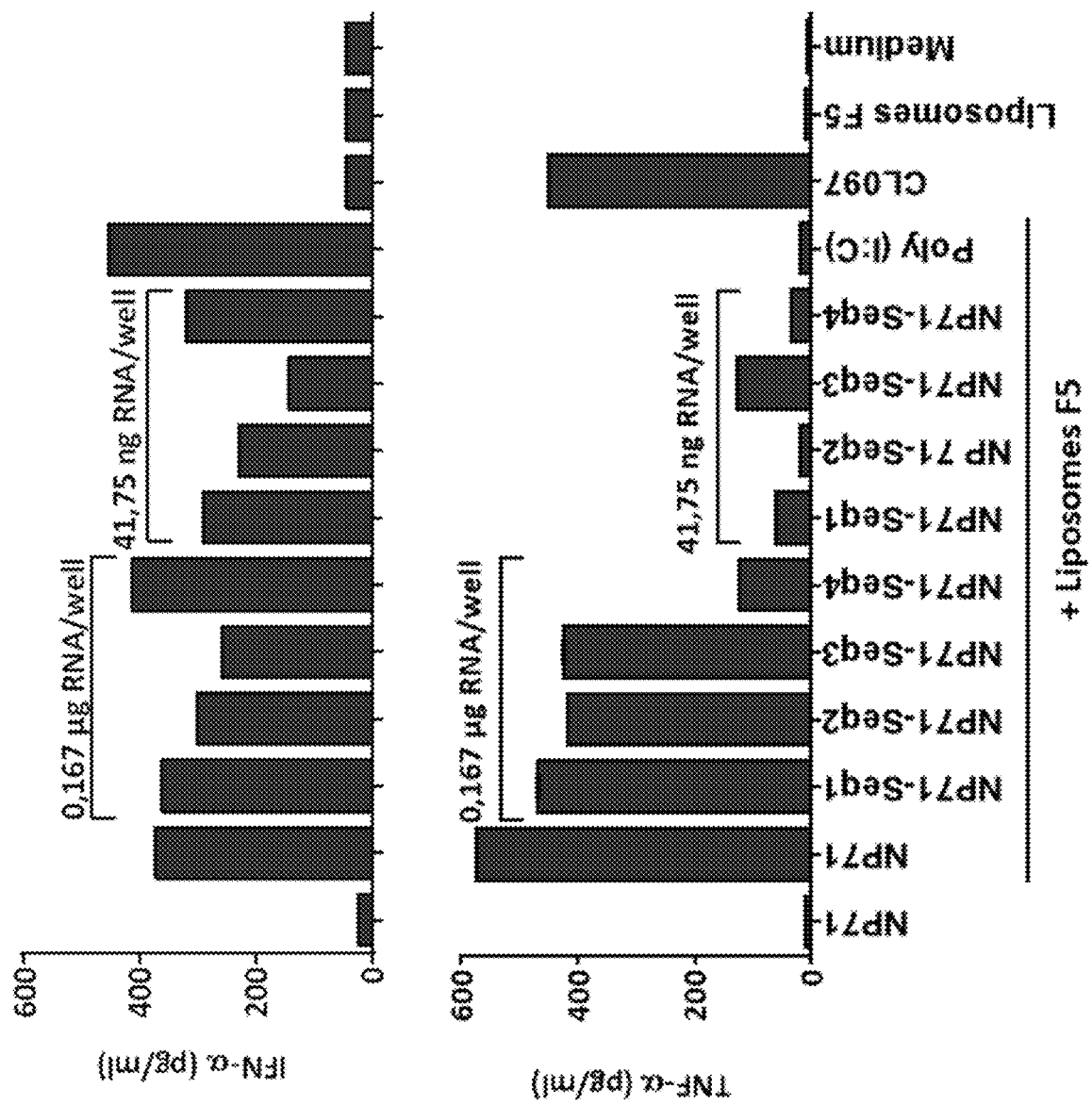
FIG. 3: Cytokine induction in human PBMCs by formulated isRNAs

$1 \times 10^6$ freshly isolated human PBMCs per well were stimulated with F5-formulated NP71 IVT RNA or fragments derived from it (NP71-Seq1-NP71-Seq4; see also FIG. 1) and the levels of IFN-α and TNF-α secreted in the cell culture supernatants upon stimulation were analyzed by ELISA. isRNA test candidates were used in two different concentrations (0,167 and 0,041 mg/well) reflecting either the equivalent amount or the equivalent molarity to the larger parental NP71 RNA fragment. F5-formulated Poly (I:C) (0,167 mg/well) and unformulated CL097 (0.2 mg/well) were used as positive controls for IFN-α and TNF-α induction respectively. Incubation of cells with medium or empty F5-liposomes served as negative controls. The immunostimulatory activity of the tested IVT RNAs relied on an appropriate way of delivery, as illustrated in FIG. 3A by liposomal formulation of NP71 RNA fragments (0,167 mg/well). The parental NP71 RNA fragment induced high levels of both IFN-α and TNF-α. In contrast to NP71, the ELISA assay revealed that stimulation of human PBMCs with isRNA NP71-Seq4 resulted in the favored cytokine induction profile with high IFN-α and low TNF-α amounts secreted into the cell supernatant. All other test candidates caused a more balanced induction of both cytokines that became prominent especially when using higher RNA concentrations (0,167 mg/well) and were disregarded for further fragmentation steps. This result indicated that the applied sequential fragmentation strategy was indeed capable to identify and select defined RNA fragments with the desired immunostimulatory activity.

Figure 3B:
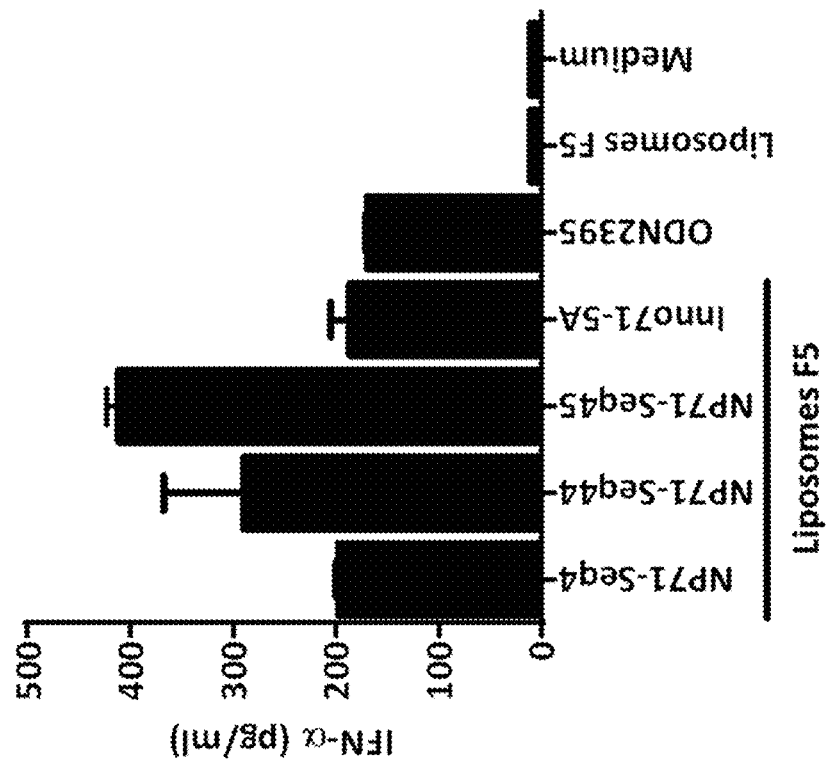

NP71-Seq4 was selected for further fragmentation to identify even shorter core sequence motifs responsible for the observed IFN-α inducing effect. The resulting small isRNA fragments Inno71-5A, NP71-Seq44 and NP71-Seq45 (see also FIG. 1 and FIG. 2B) were formulated with F5-liposomes and used in a concentration of 0,167 mg/well for the stimulation of $1 \times 10^6$ human PBMCs per well (FIG. 3B). Incubation with empty F5-liposomes or medium alone served as negative controls. Unformulated CpG ODN2395 (5 mg/ml) was used as positive control for IFN-α induction analyzed by ELISA. Inno71-5A isRNA, representing the shortest sequence stretch of NP71-Seq4, induced comparable IFN-α levels to its parental NP71-Seq4. This result indicated that Inno71-5A contained the main recognition sequence motif required for the observed immunostimulatory effect of NP71-Seq4. Unexpectedly, F5-formulated NP71-Seq44 and especially NP71-Seq45 isRNA were able to induce even higher IFN-α levels than the parental NP71-Seq4. In contrast to Inno71-5A that represented a 5' sequence portion of NP71-Seq4, NP71-Seq44 and NP71-Seq45 contained the original 5' and 3' end sequences of NP71-Seq4 and were characterized by an internal depletion of NP71-Seq4 RNA sequence parts (see FIG. 1).

Figure 4:
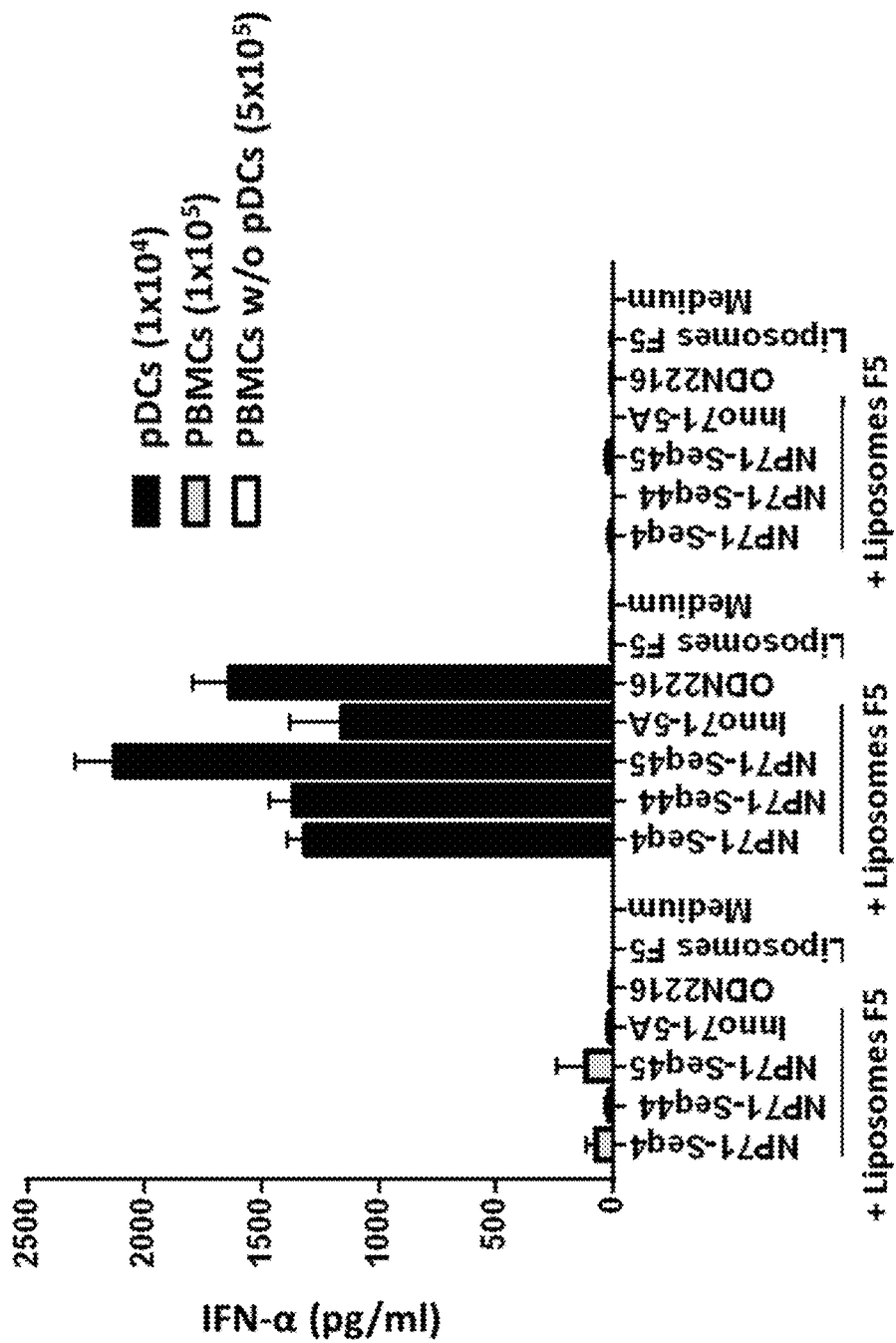
FIG. 4: pDCs are the main effector cells for IFN-α secretion upon stimulation with isRNAs

Example 4: pDCs can be Targeted In Vitro by F5-Formulated isRNAs and are the Main Effector Cells for IFN-α Secretion Upon Stimulation with isRNAs Human and mouse pDCs are well known to be the main cellular producers of IFN-α upon stimulation with single-stranded (ss) viral RNA or ssRNA containing specific sequence motifs. To investigate whether F5-formulated short isRNAs derived from Influenza NP are able to target pDCs and activate IFN-α production, human pDCs were separated from PBMCs using the MACS technology and used for an in vitro stimulation assay. Empty F5-liposomes and cells treated with medium only served as negative controls. Unformulated CpG ODN2216 (5 μg/ml) served as positive control for IFN-α induction (FIG. 4). The ELISA results indicated that pDCs can be targeted by liposomal formulated isRNAs and produce large amounts of IFN-α upon stimulation. PBMCs depleted by pDCs showed a strongly diminished IFN-α induction when compared to whole PBMCs, indicating that pDCs are likely to be the main IFN-α producers targeted by liposomal formulated isRNAs. In concordance with previous results using whole PBMCs, pDC stimulation with isRNA Inno71-5A representing the shortest isRNA sequence resulted in IFN-α levels very similar to those induced by the parental isRNA NP71-Seq4. Stimulation of pDCs with F5-formulated isRNA NP71-Seq45 induced higher amounts of IFN-α than NP71-Seq4 confirming previous experiments using whole PBMCs (see FIG. 3B). Based on these results, isRNA NP71-Seq45 was selected as the lead candidate and mainly used in further experiments.

Figure 5:
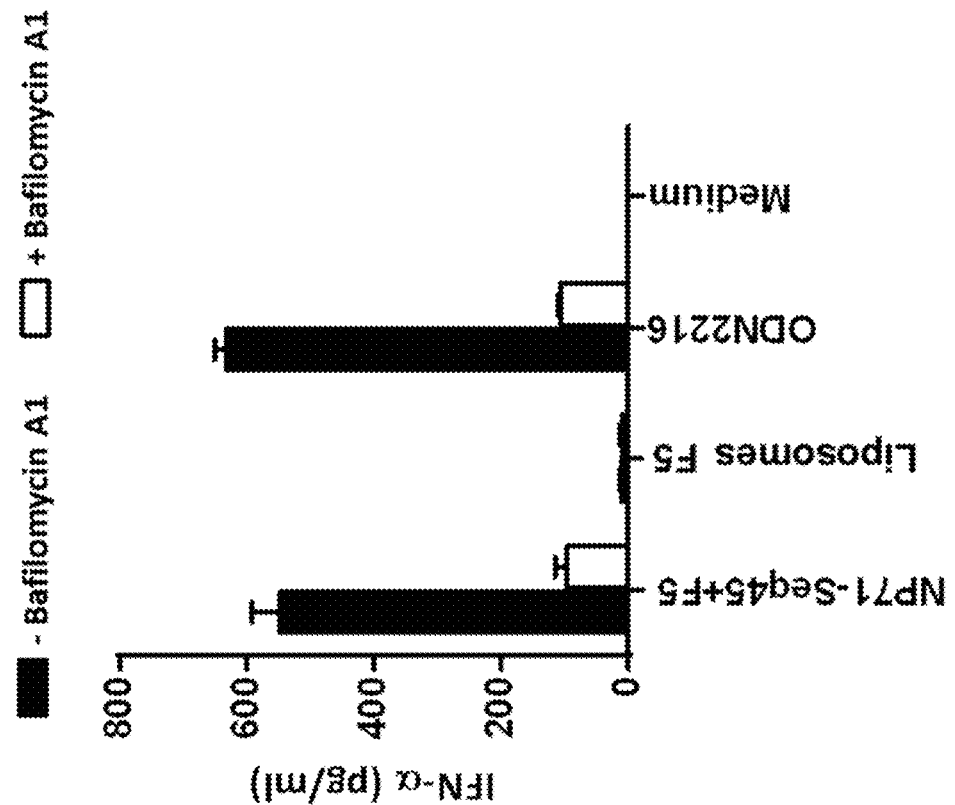
FIG. 5: Dependency of isRNA NP71-Seq45 mediated induction of IFN-α in human PBMCs on endosomally located TLRs

Example 5: isRNA NP71-Seq45 Mediated Induction of IFN-α in Human PBMCs is Depending on Endosomally Located TLRs Induction of IFN-α in pDCs by whole Influenza A genomic RNA is depending on the activation of the endosomally located TLR7 (Diebold S S. et al.; Science 303 (5663), 1529-1531 (2004)). In order to evaluate that IFN-α induction upon stimulation with F5-formulated isRNAs is dependent on nucleic acid sensing, endosomal TLRs, freshly isolated whole human PBMCs were pretreated for 1 h with 250 nM Bafilomycin A1 and subsequently incubated for 14 h with NP71-Seq45 (FIG. 5). Bafilomycin A1 prevents endosomal acidification by inhibiting vacuolar H+ ATPase resulting in the blockade of endosomally located TLRs sensing nucleic acids like TLR3, TLR7/8 or TLR9. Empty F5 liposomes and cells incubated with medium only served as negative controls, whereas unformulated CpG ODN2216 (TLR9 ligand) functioned as positive control for Bafilomycin A1 treatment. As expected, Bafilomycin A1 pretreatment strongly diminished the induction of IFN-α by CpG ODN216 whereas cell viability was not affected by the used Bafilomycin A1 concentration (data not shown). A similar strong reduction of IFN-α secretion could be observed for PBMCs incubated with Bafilomycin A1 followed by NP71-Seq45 stimulation indicating that isRNAs are recognized by an endosomal TLR.

Example 6: isRNA NP71-Seq45 is a Specific Agonist for TLR7

Figure 6:
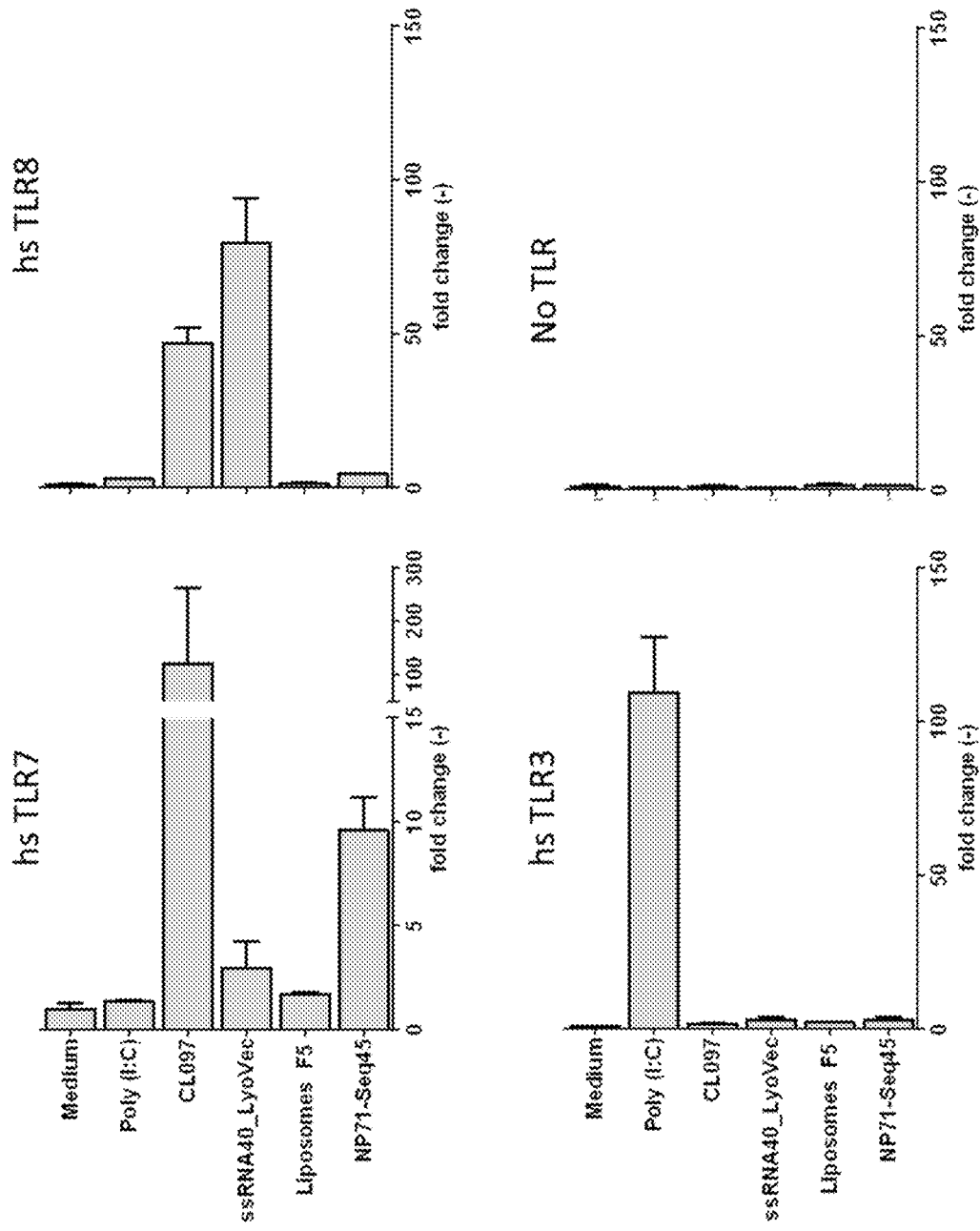
FIG. 6: Determination of the nucleotide-sensing endosomal TLR which is activated by NP71-Seq45

In order to analyze which nucleotide-sensing endosomal TLR is activated by NP71-Seq45, HEK293 cells stably co-expressing human TLR3, TLR7 or TLR8 in addition to a NF-κB-inducible luciferase reporter gene were incubated with F5-formulated isRNA NP71-Seq45 and luciferase signals were compared to untreated (medium only) cells (FIG. 6). TLR9 expressing HEK293 cells were excluded, as TLR9 is exclusively recognizing specific DNA molecules. Positive controls were F5-formulated Poly (I:C) for TLR3, unformulated CL097 for TLR7 and TLR8 as well as ssRNA40 complexed with cationic lipids for TLR8. Empty F5-liposomes treated cells served as negative control. Addition of F5-formulated NP71-Seq45 isRNA activated the reporter gene only in human TLR7 co-expressing HEK293 cells, whereas no luciferase signals were obtained in other TLR expressing cells. This result indicated that NP71-Seq45 acts as a specific ligand for human TLR7.

Taken together these results revealed that liposomal formulated isRNAs are capable to induce IFN-α production in vitro in pDCs and that the immunostimulatory activity is mediated mainly by TLR7 located in endosomes.

Example 7: F5-Formulated isRNAs Induce High Levels of IFN-α but Only Marginal Levels of IFN-γ, TNF-α and IL10 in Human PBMCs A key parameter for the selection of isRNAs as vaccine adjuvants was their ability to induce high levels of IFN-α and no or only minimal levels of strongly proinflammatory cytokines like TNF-α and IFN-γ that might cause harmful systemic side effects upon vaccination. Furthermore, isRNA-based adjuvants should not lead to strong induction of anti-inflammatory cytokines like IL10 that inhibits the activity of Th1 cells, natural killer (NK) cells and macrophages thereby promoting a Th2 phenotype of the immune response.

Figure 7:
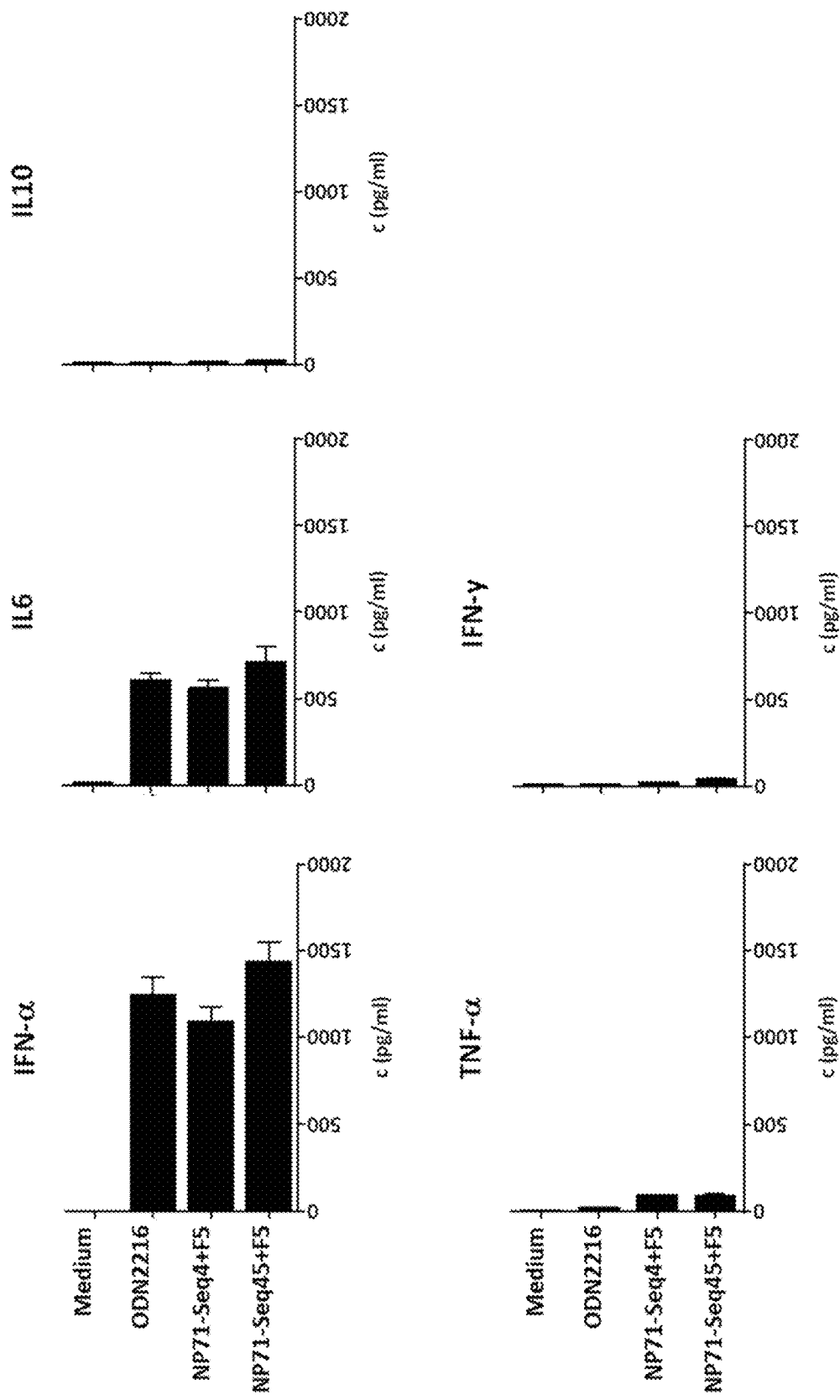
FIG. 7: Analysis of the cytokine profile which is induced in human PBMCs by formulated isRNAs

To analyze the cytokine profile induced by isRNA NP71-Seq45 and its parental fragment NP71-Seq4 a multiplexed bead immunoassay was performed. 1×10^6 freshly isolated human PBMCs per well were incubated with F5-formulated isRNAs (0,167 μg/well) or unformulated CpG ODN2216 (1 μg/well) as positive and empty F5-liposomes as negative control. Analyzed cytokine concentrations in the cell supernatant included IFN-α, IL6, IFN-γ, TNF-α and IL10 (FIG. 7). Both isRNAs induced high IFN-α levels with NP71-Seq45 having a superior effect, confirming previous results. The detected IFN-α amounts were in a similar range as observed for D-type CpG ODN2216 that is known to induce strong pDC IFN-α secretion. For TNF-α, IFN-γ and IL10 only marginal levels were detectable whereas IL6, a cytokine with context-dependent pro- and anti-inflammatory properties and involved in B-cell activation and maturation, was moderately induced by isRNA or CpG ODN2216.

The cytokine profile induced by isRNAs in human PBMCs in vitro indicates that the identified isRNAs mount an innate immune response characterized by the production of Th1 cytokines with the potential to enhance the generation of humoral and cellular antigen-specific immune responses while minimizing the induction of potentially harmful main proinflammatory cytokines.

Example 8: In Vitro Stimulation of Mouse Cells with F5-Formulated isRNAs Results in a Strong, pDC Dependent Induction of IFN-α and Only Marginal TNF-α Secretion Previous in vitro results using freshly prepared human PBMCs could clearly demonstrate the strong immunostimulatory capacity of the identified isRNAs with high IFN-α and only marginal TNF-α induction. In order to perform meaningful in vivo preclinical studies using mouse models in subsequent experiments, the immunostimulatory effect, including the responsible main target cells, had to be confirmed in vitro.

Figure 8:
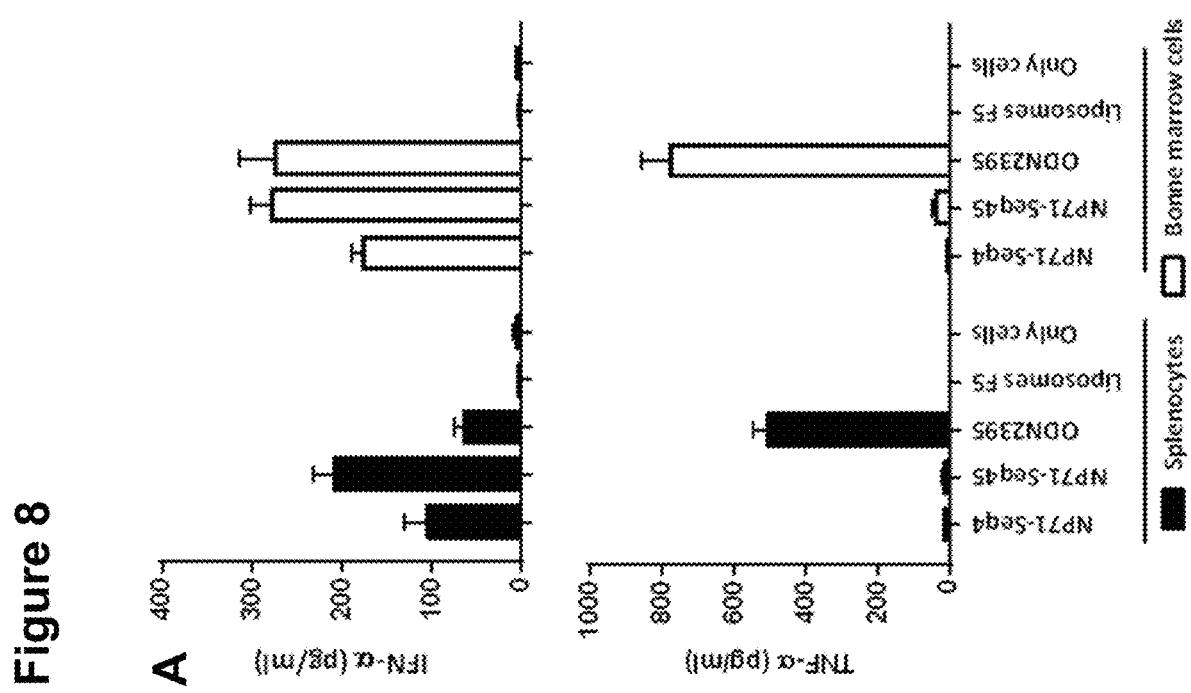
FIG. 8: Cytokine induction in mouse cells by formulated isRNAs

Therefore, Balb/c bone marrow-derived cells and splenocytes were isolated and incubated with F5-formulated isRNA NP71-Seq4 or NP71-Seq45, unformulated CpG ODN2359 (0.5 µg/well) or empty F5-liposomes (FIG. 8A). Untreated cells (only cells) served as negative control. In addition, splenocytes depleted by pDCs, enriched pDCs and enriched conventional dendritic cells (cDCs) were stimulated as noted before (FIG. 8B). Cytokine concentrations in the cell supernatants were analyzed by ELISA.

Confirming the results obtained in human PBMCs, stimulation of mouse splenocytes or bone marrow-derived cells with isRNAs leads to a strong IFN-α and only a marginal TNF-α induction. In contrast, incubation with the TLR9 agonist class C CpG ODN2359 elicited a strong induction of both cytokines tested. Furthermore and in accordance to human PBMC in vitro results (see also FIG. 3B) NP71-Seq45 revealed a stronger immunostimulatory capacity than its parental RNA-fragment NP71-Seq4. The induction of IFN-α upon isRNA stimulation was strictly dependent on pDCs as already observed using human cells.

The in vitro results using freshly prepared murine cells indicated the broad applicability of the identified isRNAs and enabled further in vivo experiments using mice as model system.

Example 9: F12-Formulated isRNA Stimulation In Vivo Leads to a Time and Dose Dependent Induction of IFN-α

Figure 9:
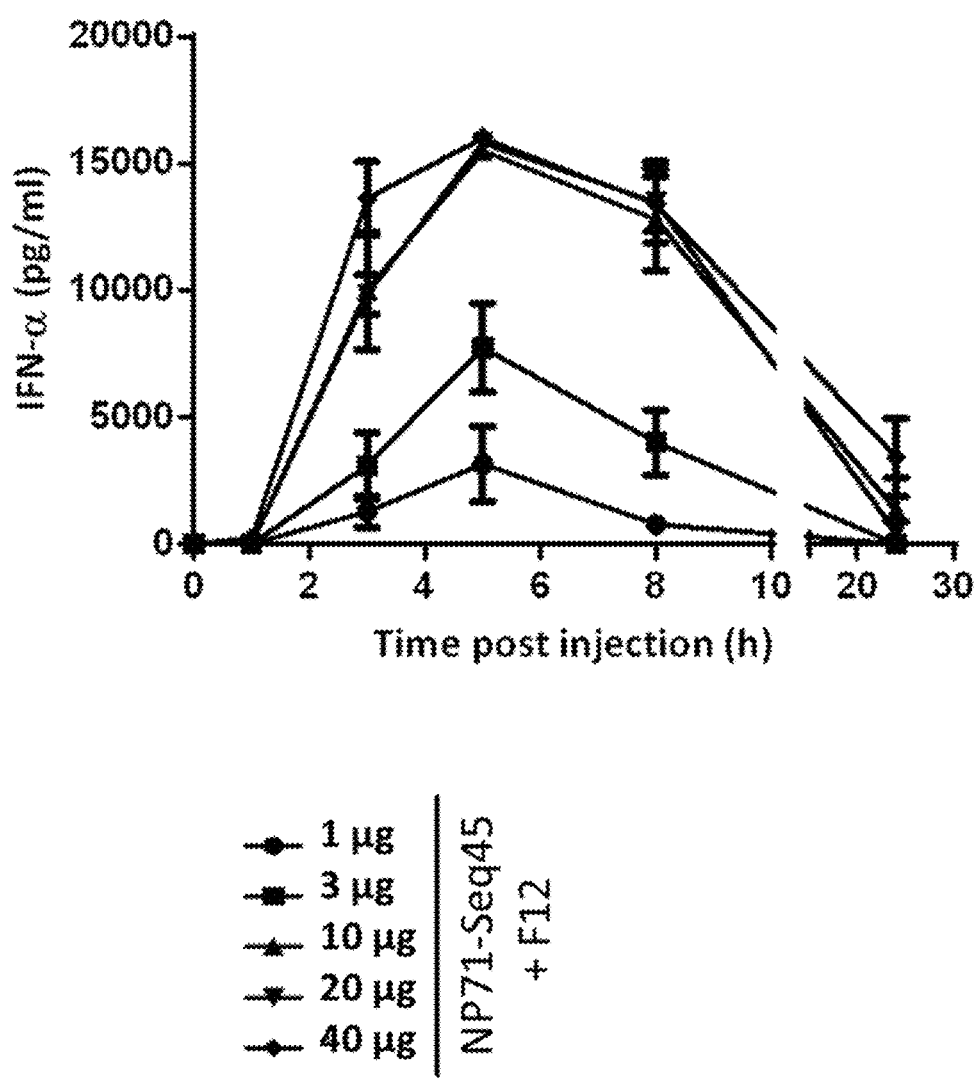
FIG. 9: Time and dose dependent induction of IFN-α in vivo by formulated isRNA

Time- and dose-response relationships upon applying isRNA adjuvants are important parameters for safety evaluation and the development of an optimal immunization regime. Therefore, Balb/c mice were injected i.v. once with increasing doses of formulated NP71-Seq4 isRNA. In contrast to the liposomal formulation F5 used in in vitro experiments, the liposomal formulation F12 used for in vivo studies was adapted for an optimal delivery of isRNAs into the spleen, the main side of immune activation upon i.v. administration. Mouse serum samples were taken after 1, 3, 5, 8 and 24 h post injection to analyze the in vivo stimulatory effect of isRNAs in regard to the dose and time dependent induction of IFN-α as measured by ELISA (FIG. 9).

Irrespective of the administered dosage, the maximal IFN-α induction in vivo was already achieved 5 h after immunization and declined back to normal levels thereafter. The i.v. administration of 10 µg NP71-Seq4 isRNA was already sufficient for the maximal stimulatory effect and could not be increased by higher doses. Even after injection of 40 µg isRNA, adverse effects were not visible, indicating the good tolerability of isRNAs after systemic application.

Example 10: Repetitive i.v. Administration of F12-Formulated isRNAs at Frequent Intervals Led to a Systemic TLR Response Tolerance that can be Overcome by an Adapted Immunization Regime TLR response tolerance is a well-known effect, in which repeated exposure to TLR agonists results in a diminished cytokine release response (Broad, A. et al.; Curr Med Chem 13(21), 2487-2502 (2006)). As a consequence, vaccination with co-administration of isRNA adjuvants at frequencies too high would have a detrimental impact on the overall immune response and should be avoided. Therefore, it was important to analyze in which time intervals isRNAs can be administered without leading to a TLR response tolerance.

Figure 10:
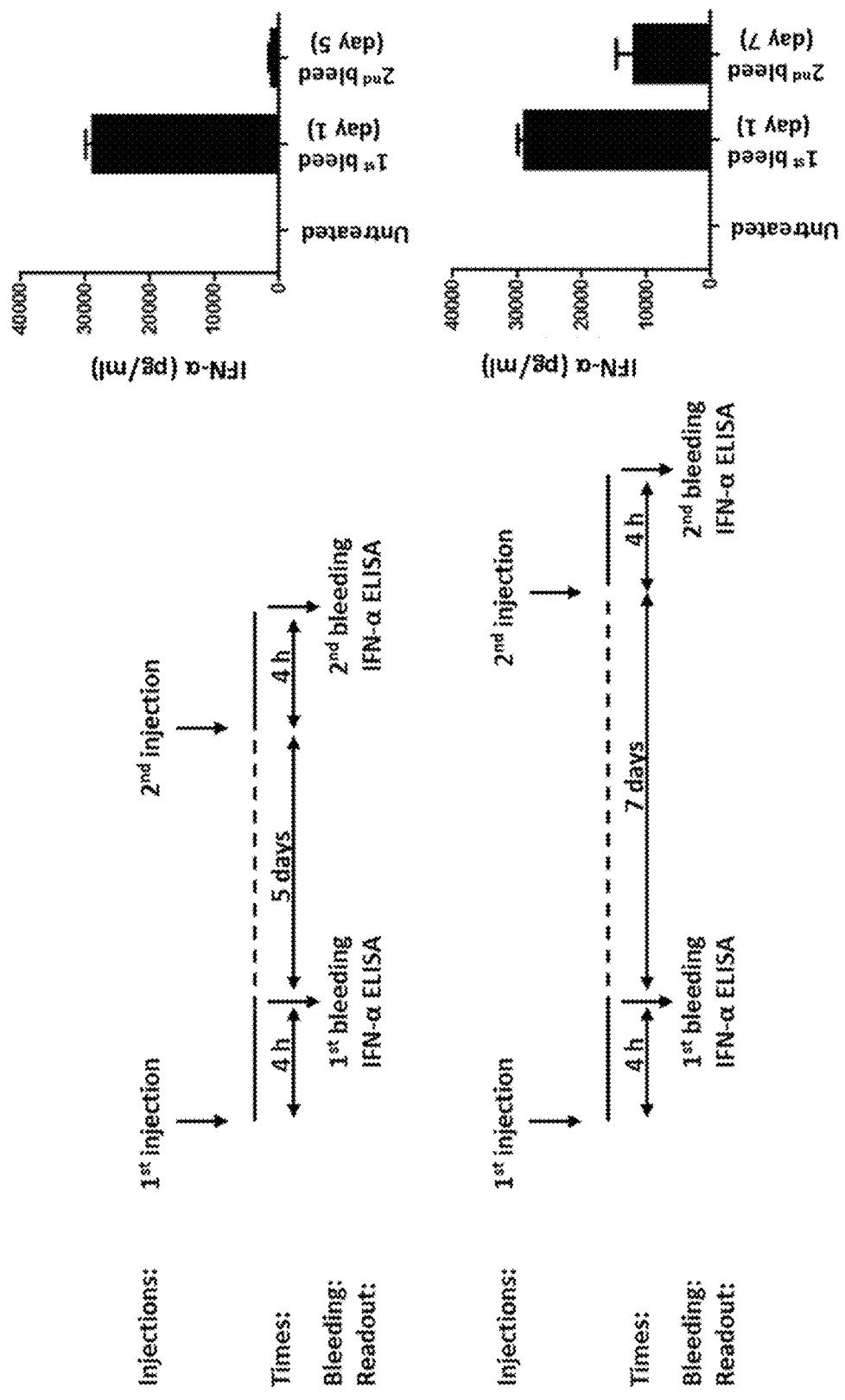
FIG. 10: Repetitive i.v. administration of formulated isRNAs at frequent intervals leads to a systemic TLR response tolerance that can be overcome by an adapted immunization regime

F12-formulated NP71-Seq4 isRNA was injected i.v. twice into Balb/c mice at an interval of 5 ($1^{st}$ group) or 7 days ($2^{nd}$ group) (FIG. 10). Both groups were injected with 20 µg isRNA/mouse and blood samples were taken 4 h after each injection. The used isRNA concentration and time of blood sampling after injection were shown to be optimal in previous experiments (see FIG. 9). Serum levels of IFN-α were detected by ELISA. Administration of F12-formulated NP71-Seq4 isRNA at a time interval of 5 days resulted in a pronounced TLR response tolerance effect with a strongly diminished IFN-α secretion after the second injection. However, the TLR responsiveness could be almost completely restored by an injection interval of 7 days. Therefore, subsequent vaccination experiments combining a model antigen and isRNA adjuvants were performed using multiple immunizations with a minimal time interval of 10-14 days after each injection to ensure a maximal isRNA adjuvant effect.

Example 11: F12-Formulated isRNAs in Combination with HBcAg-#A79 VLPs Induce an Antigen-Specific B- and T-Cell Response In Vivo In previous experiments we could demonstrate that the identified isRNAs can stimulate the innate immune system, especially pDCs, in highly efficient and largely TLR7 dependent manner, resulting in the release of high amounts of IFN-α. In subsequent in vivo immunization studies, we wanted to analyze if the triggering of the innate immune system by isRNAs can be translated in an efficient and antigen-specific adaptive immune response of both, B- and T-cells.

For this purpose we combined selected isRNAs with the virus-like particle (VLP) based model antigen HBcAg-#A79. VLPs consist of viral structural proteins with the inherent ability to self-assemble into macromolecular structures. VLPs resemble the virus from which they originated, but do not contain any viral genetic material. Thus, VLPs are non-infectious and are generally considered as a safe vaccine format. The high intrinsic immunogenicity of VLPs can be transferred to heterologous epitopes displayed in a repetitive manner on the surface of VLPs. The used model antigen HBcAg-#A79 is based on recombinantly produced, chimeric VLPs derived from Hepatitis B virus core antigen (HBcAg), presenting a genetically inserted epitope of the cell surface located tumor-associated antigen (TAA) CLDN6 on their surface. CLDN6 epitope #A79 was an ideal candidate for immunization studies because it functions as a combined B- and T-cell epitope, the latter restricted to MHC-class I H-2 Kd expressed by Balb/c inbred mice.

Figure 11A:
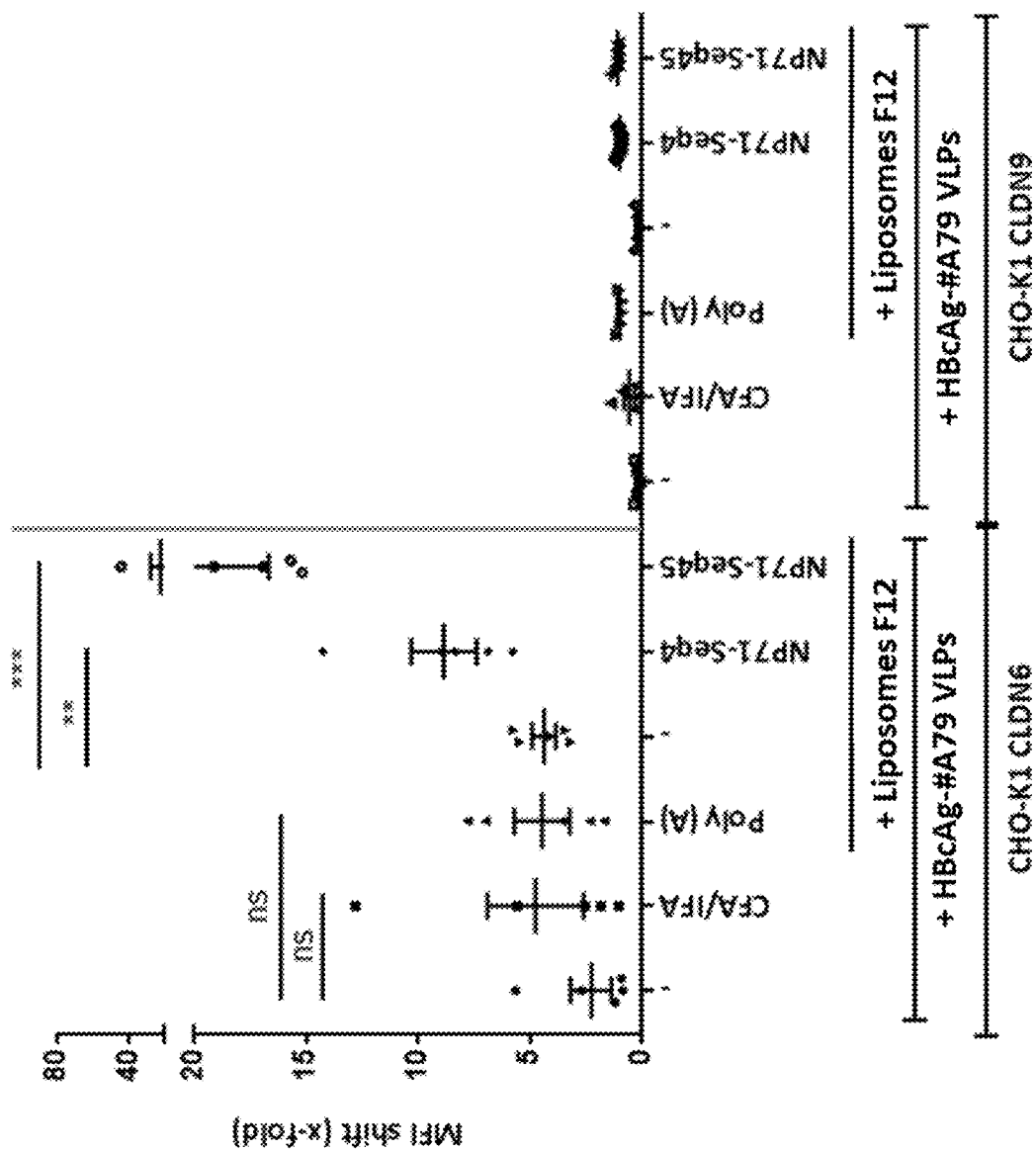
FIG. 11: Formulated isRNAs in combination with HBcAg-#A79 VLPs induce an antigen-specific B- and T-cell response in vivo
Figure 11B:
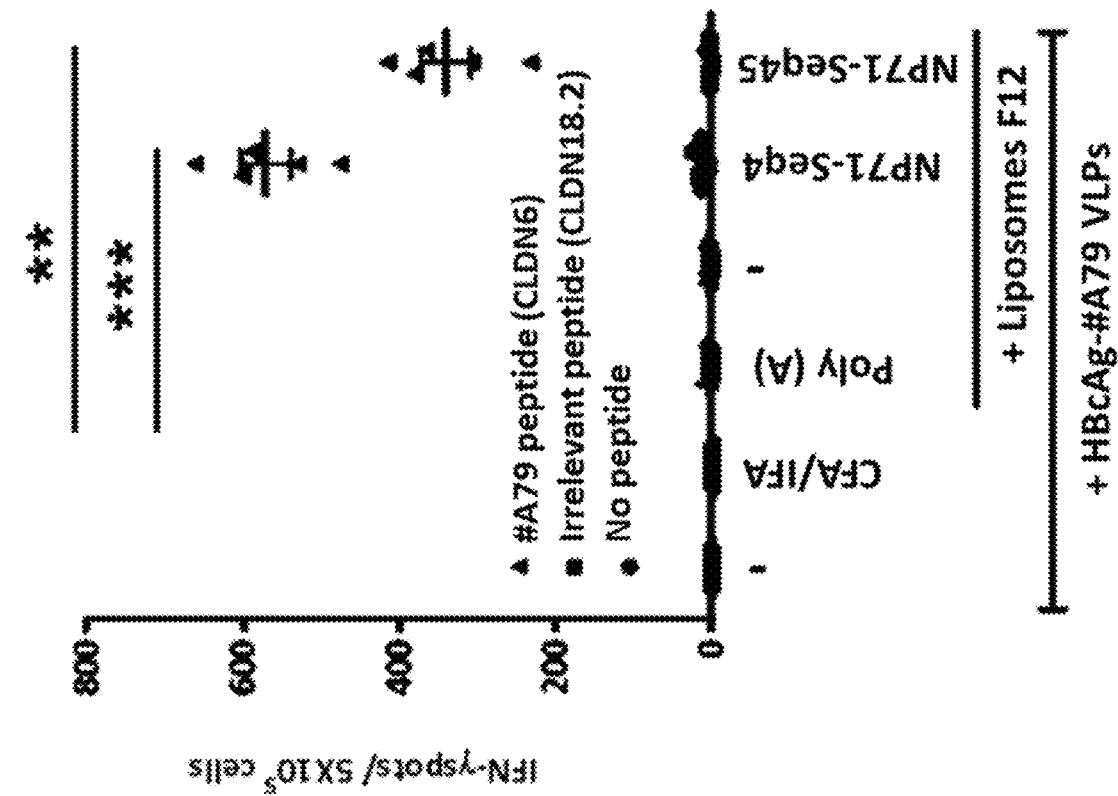

Balb/c mice were immunized i.v. four times at two week intervals with HBcAg-#A79 VLPs combined with F12-formulated isRNA NP71-Seq4 or NP71-Seq45. Untreated mice or mice immunized with empty F12 liposomes, F12-formulated Poly(A) RNA or HBcAg-#A79-VLPs adjuvanted with CFA/IFA (immunized s.c.) served as controls. Ten days after the third immunization, blood samples were taken for analysis of the antigen-specific humoral immune response by flow cytometry (FIG. 11A). Five days after the fourth immunization animals were sacrificed and splenocytes isolated to analyze the induction of specific T-cell response by an Enzyme-linked ImmunoSpot (ELISpot) assay (FIG. 11B).

Flow cytometry analysis was performed using living CHO-K1 cells stably transfected with the target TAA CLDN6 or its close homologue CLDN9 for specificity control. Detection of bound antibodies was expressed by the mean fluorescence intensity (MFI) shift calculated by dividing the MFI of immune serum by the MFI of the respective pre-bleed serum (before the first immunization). MFI-shifts greater than 2-fold were considered as positive antigen-specific antibody responses. HBcAg-#A79 VLPs immunized without the addition of adjuvants induce a weak antigen-specific immune response with only a few animals showing positive reactions. The antigen-specific immune response was slightly increased by the adjuvantation with Poly (A) RNA, CFA/IFA or empty F12-liposomes. However, this effect was not significant (ns) when compared to non-adjuvanted HBcAg-#A79 VLPs. Co-administration of isRNA NP71-Seq4 or NP71-Seq45 strongly and highly significantly increased the CLDN6 antigen-specific antibody response upon immunization with HBcAg-#A79 VLPs without increasing any unspecific binding of antibodies to CLDN9. Immunization of animals using NP71-Seq45 isRNA as adjuvant resulted generally in higher antibody MFI-shifts than NP71-Seq4.

ELISpot analysis revealed that immunizations using HBcAg-#A79 VLPs adjuvanted with Poly (A) RNA or CFA/IFA, as well as the addition of empty F12-liposomes resulted in a complete lack of detectable T-cell responses. In contrast, co-administration of isRNAs induced a highly significant, #A79 peptide specific T-cell response in which NP71-Seq4 led to an increased number of IFN-γ spots when compared to NP71-Seq45.

The results obtained by immunization of mice with HBcAg-#A79 VLPs in combination with liposomal formulated isRNA adjuvants clearly indicated that the efficient induction of a high-titer and antigen-specific antibody response capable to detect the target TAA in its native conformation on living cells was strongly depending on the used isRNA adjuvants. Furthermore, only the combination of the model antigen with formulated isRNAs was able to induce simultaneously a TAA-peptide specific T-cell response reflected by high numbers of IFN-γ spots. Thus, the identified isRNAs administered i.v. in a liposomal formulation can act as an adjuvant to boost the generation of humoral and cellular antigen-specific immune responses in vivo when combined with a recombinant protein-based vaccine.

Example 12: Antigen-Specific B- and T-Cell Responses Induced by Immunization of F12-Formulated isRNAs in Combination with HBcAg-#A79 VLPs are Dose Dependent In a previous experiment (see FIG. 9), we could show that the in vivo induction of IFN-α by formulated isRNAs is time and dose dependent with a maximal effect already achieved after a single injection of 10 µg isRNA. The correlation of this dose dependency on the in vivo induction of a combined and antigen-specific B- and T-cell response was analyzed by immunizing mice i.v. with HBcAg-#A79 VLPs adjuvanted with increasing doses (5, 10, 20 and 40 µg/injection) of F12-formulated NP71-Seq45 isRNA. The immunization schedule and experimental setup were identical to those described in example 11.

Figure 12A:
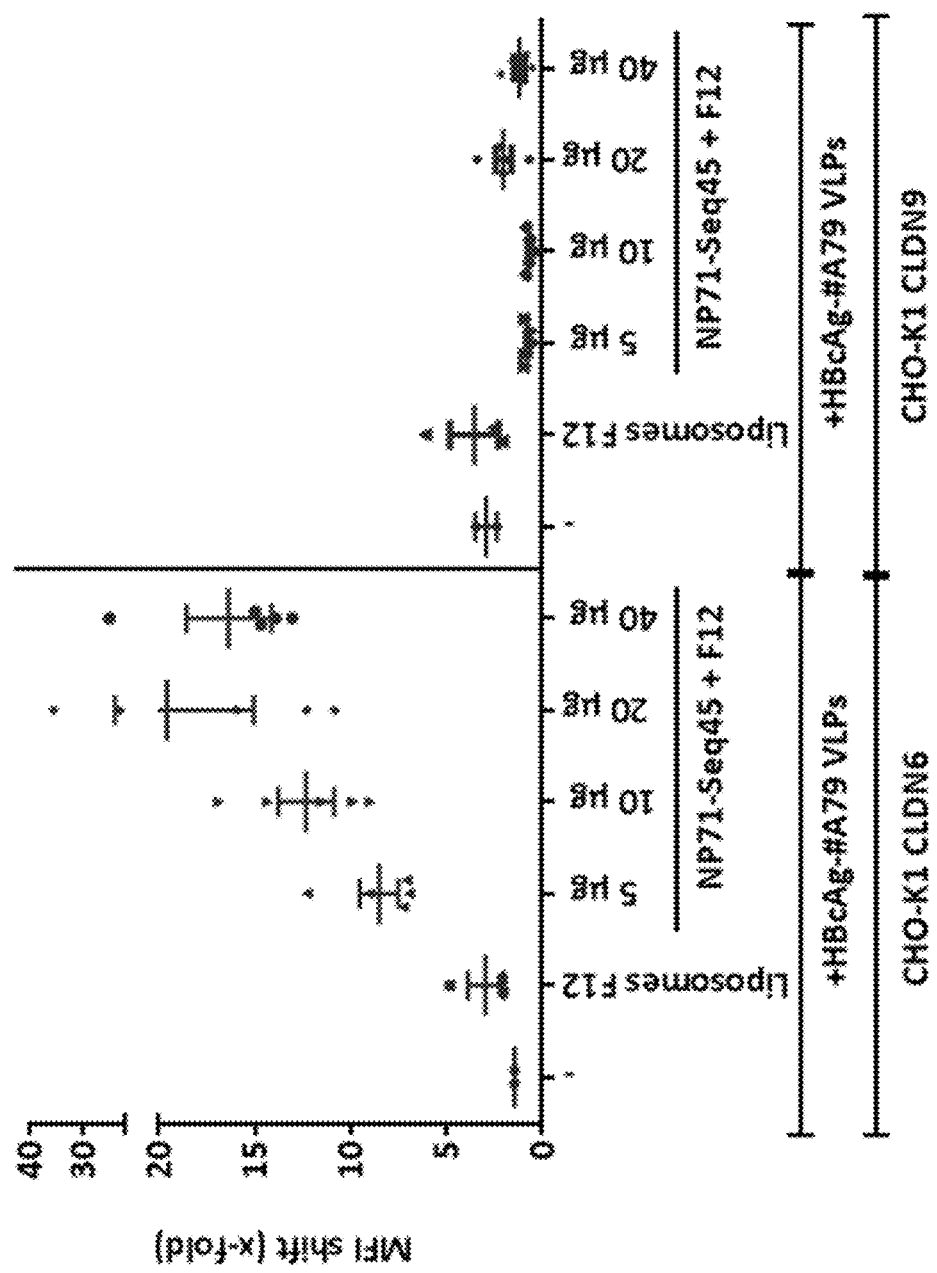
FIG. 12: Dose dependent induction of antigen-specific B- and T-cell responses by immunization using formulated isRNAs in combination with HBcAg-#A79 VLPs
Figure 12B:
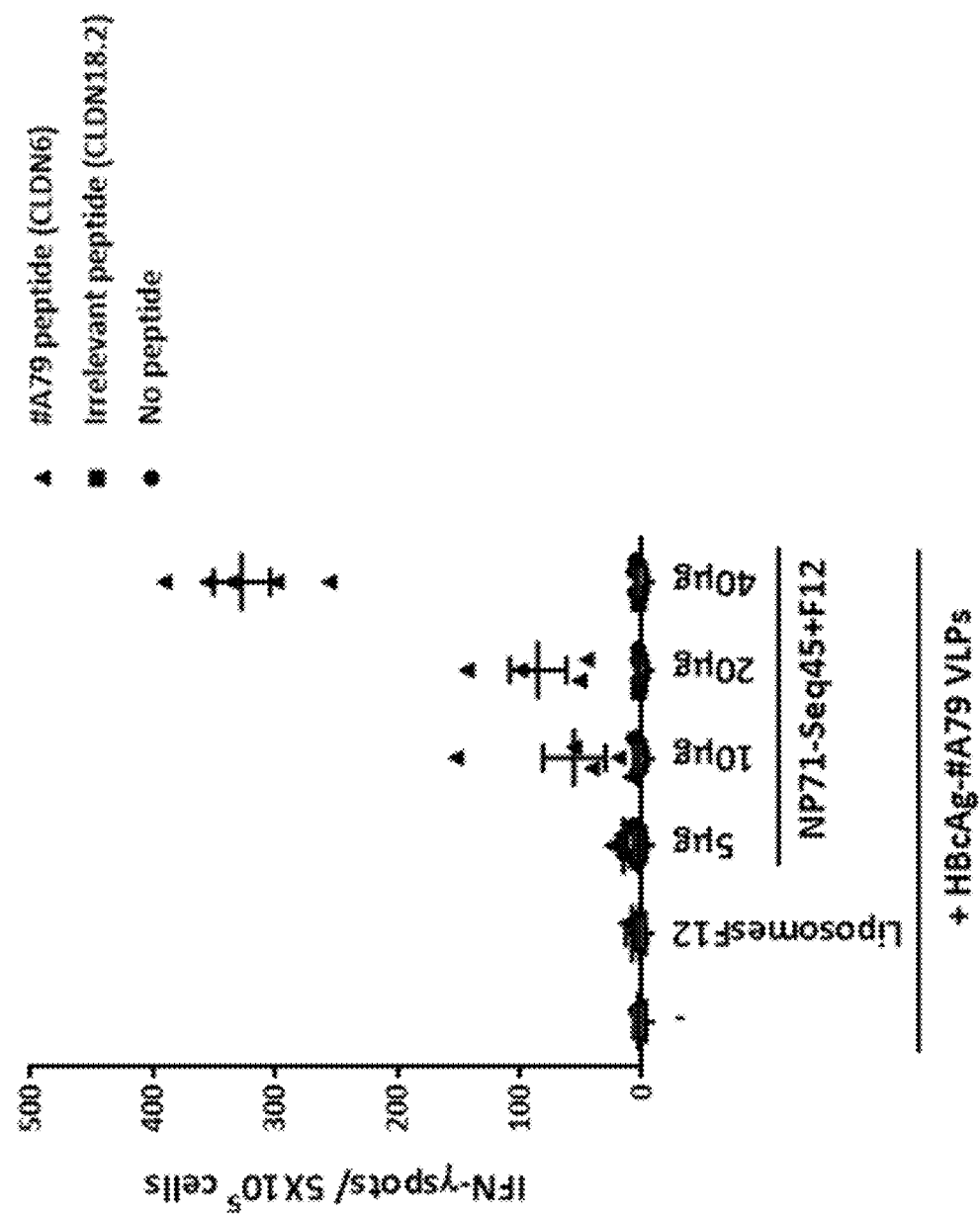

Already 5 µg/injection of F12-formulated NP71-Seq45 isRNA was sufficient to show a clearly enhanced antibody response as shown by flow cytometry (FIG. 12A). In addition, a dose dependent antigen-specific antibody response up to a concentration of 20 µg/injection isRNA with no further increase when applying 40 µg/injection was detectable. This dose dependency resembled the dose dependent course of IFN-α secretion which pointed towards a crucial role of IFN-α in the adjuvant activity of F12-formulated isRNAs. A significant enhancement of the #A79-peptide specific T-cell response was detectable by IFN-γ ELISpot when applying at least 10 µg/injection isRNA (FIG. 12B). Furthermore and in contrast to the results observed for isRNA triggered B-cell responses, the peptide-specific T-cell response was further enhanced by increasing the isRNA adjuvant dosage up to 40 µg/injection of NP71-Seq45. Unspecific T-cell reactivity against an irrelevant peptide derived from the TAA CLDN18.2 was absent even at the highest NP71-Seq45 dose.

These results indicated a differential dose depending behavior of isRNA induced B- and T-cell immune response enabling their modulation by adapting the applied isRNA dose.

Example 13: Antigen-Specific Antibodies Elicited by Immunization with F12-Formulated isRNAs and HBcAg-#A79 VLPs Kill Target Positive Cells by CDC Successful vaccination strategies might depend on the induction of antigen-specific antibodies that are able to bind their target protein in its native conformation and subsequently mediate target positive cell killing via immune effector mechanisms. One of the main cytolytic effector functions mediated by the Fc portion of antibodies is the complement-dependent cytotoxicity (CDC) that was analyzed by using 1:10 diluted, unpurified sera derived from the immunization experiment described in example 11.

Figure 13:
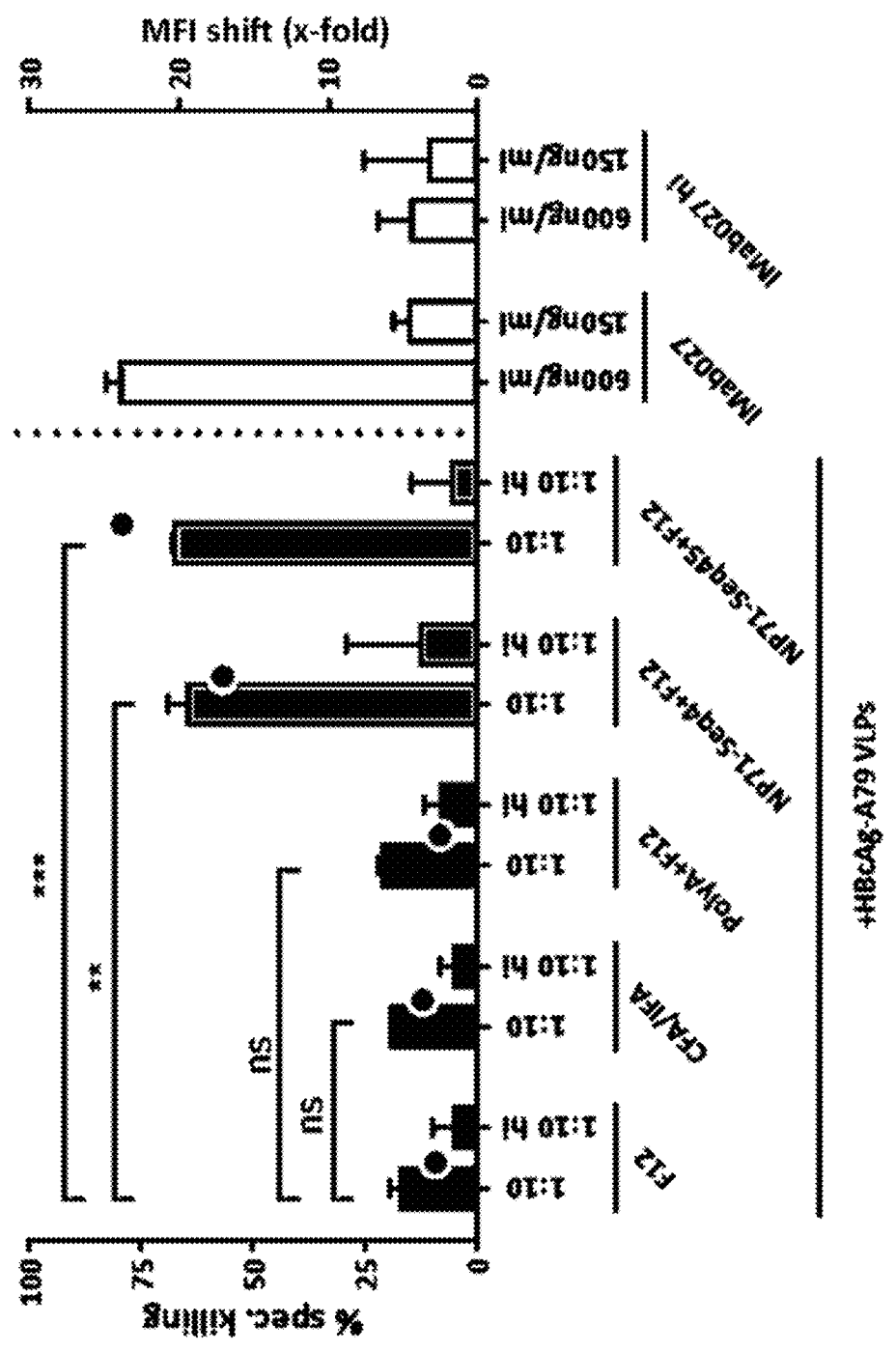

CDC assays revealed that sera from mice immunized with HBcAg-#A79 VLPs and F12-formulated isRNAs exert efficient cytocidal effector functions (FIG. 13). The cytolytic activity was strictly depending on active complement as heat inactivated complement (1:10 hi) strongly diminished cell killing. Sera derived from immunizations with HBcAg-#A79 VLPs in combination with empty F12-liposomes, CFA/IFA or adjuvanted with F12-formulated Poly (A) RNA were not able to exert a comparable effector function. The cytocidal effector function of the induced antibodies was largely correlating with their calculated MFI-shift.

In mice, isotype IgG3 is the best complement activator followed by IgG2a and IgG2b. Therefore, the results from the CDC assay indicated that isRNA adjuvants induce a cytokine milieu in vivo promoting immunoglobulin class switch and that elicited antigen-specific antibodies are capable to kill target positive cells by CDC.

Example 14: Immunization of F12-Formulated isRNA in Combination with HBcAg-#A79 VLPs Resulted in a Balanced Antigen-Specific IgG2a/IgG1 Response For a better understanding of the adjuvant properties of the identified isRNAs in combination with the model antigen HBcAg-#A79 VLP, the determination of immunoglobulin (Ig) isotype switch can provide insight whether the vaccine composition influences the balance between the Th1 or Th2 profile of an immune response. In the mouse system, the presence of elevated IgG2a isotype levels is indicative for a Th1 mediated immune response whereas high levels of IgG1 antibodies are a hallmark for a Th2 mediated immune response.

Figure 14:
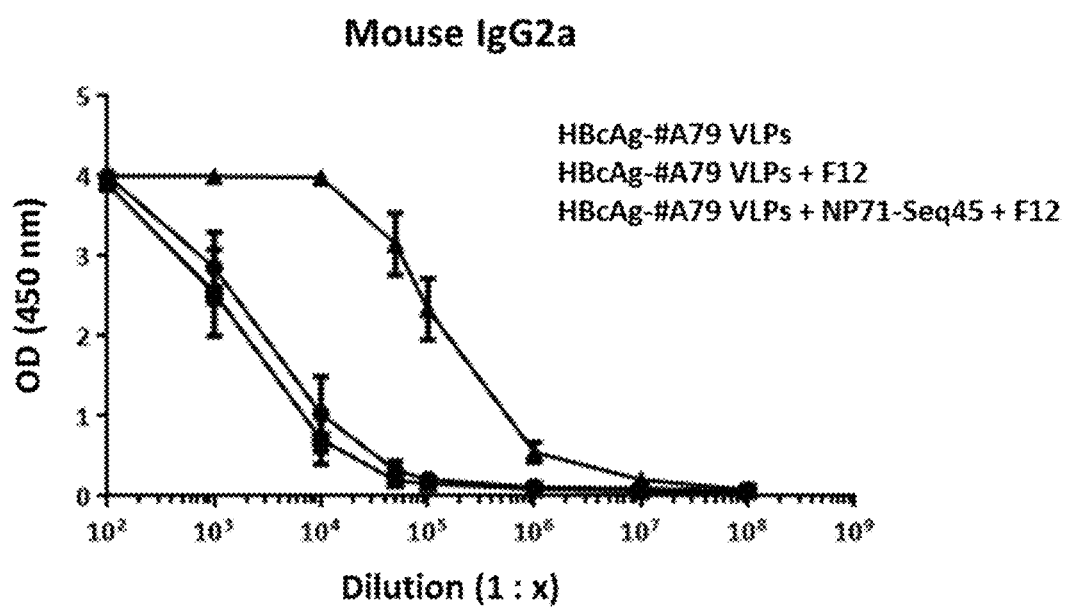
FIG. 14: Immunization of formulated isRNA in combination with HBcAg-#A79 VLPs results in a balanced antigen-specific IgG2a/IgG1 response
Figure 14:
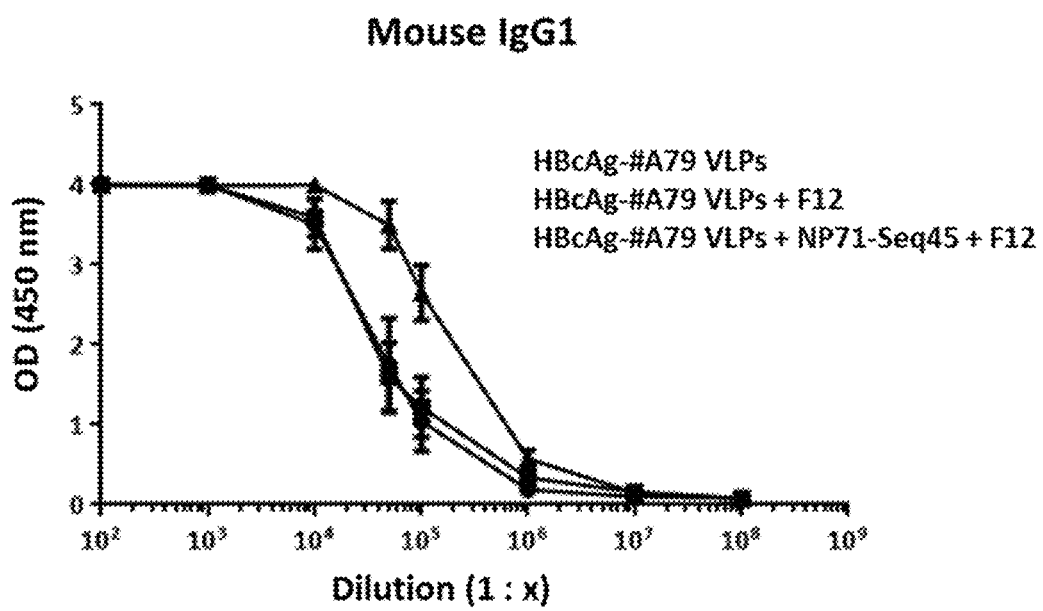
Figure 14C:
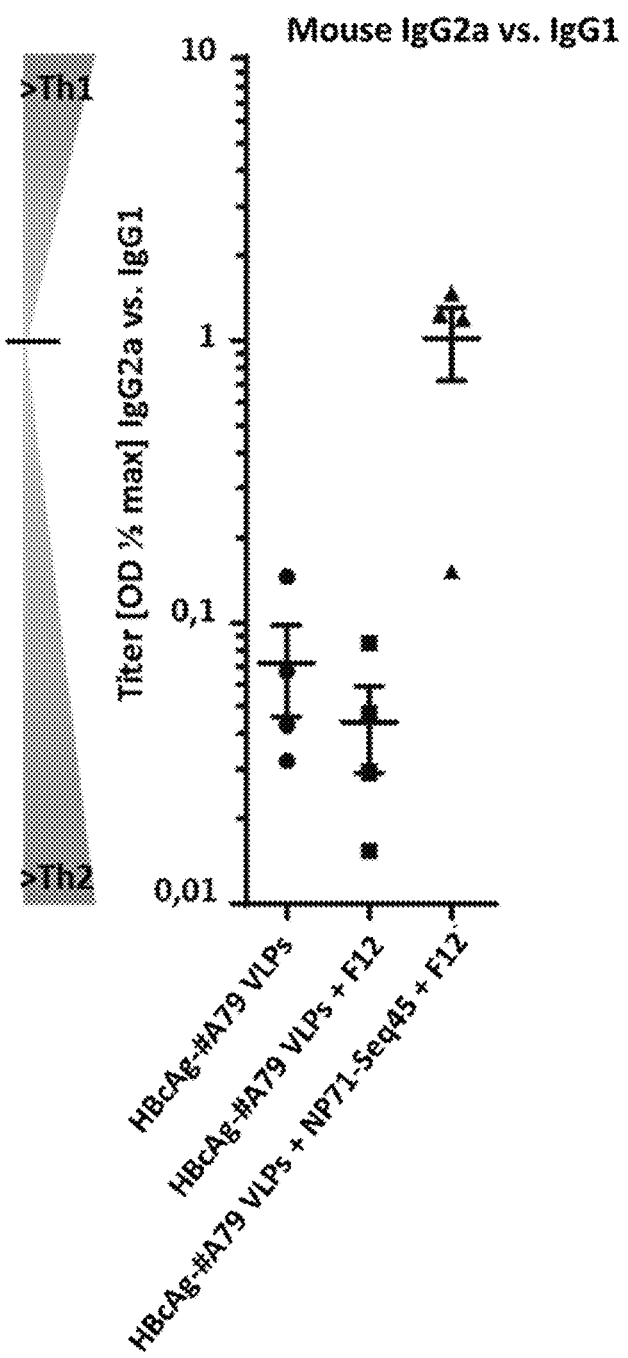

For the analysis of Ig isotype levels, sera from mice immunized as described in example 11 were used and titrations of IgG1 or IgG2a antibodies specifically reacting against the linear #A79-peptide were analyzed by ELISA (FIGS. 14A and 14B). Half maximal antibody titers were calculated and represented as ratio of IgG2a versus IgG1 (FIG. 14C). The immunization with non-adjuvanted HBcAg-#A79 VLPs or VLPs combined with empty F12-liposomes resulted in high IgG1 and very low IgG2a antibody titers, referring to a predominantly Th2 driven immune response. In contrast, antibodies raised by immunizations with HBcAg-#A79 VLPs adjuvanted with F12-formulated NP71-Seq45 elicited moderately higher IgG1 and strongly enhanced #A79-peptide specific IgG2a antibody titers, resulting in a balanced Th1/Th2 immune response.

Example 15: The Antigen-Specific Antibody Response Induced by F12-Formulated isRNA in Combination with HBcAg-#A79 VLPs is Mainly Depending on pDCs Previous in vitro experiments indicated that the identified isRNAs exerted their immunostimulatory effect mainly by endosomal TLR activation in pDCs resulting in the secretion of high IFN-α amounts (see FIG. 4 and FIG. 8).

Figure 15:
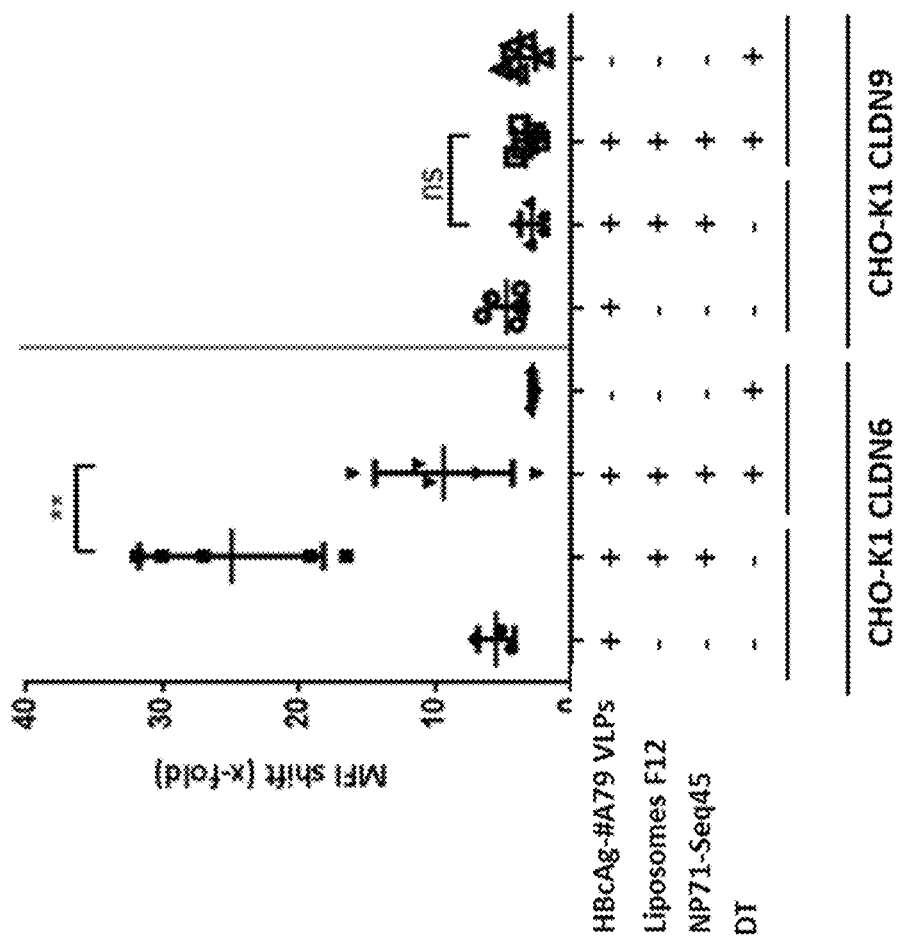
FIG. 15: Dependency of the antigen-specific antibody response induced by formulated isRNA in combination with HBcAg-#A79 VLPs on pDCs
Figure 15:
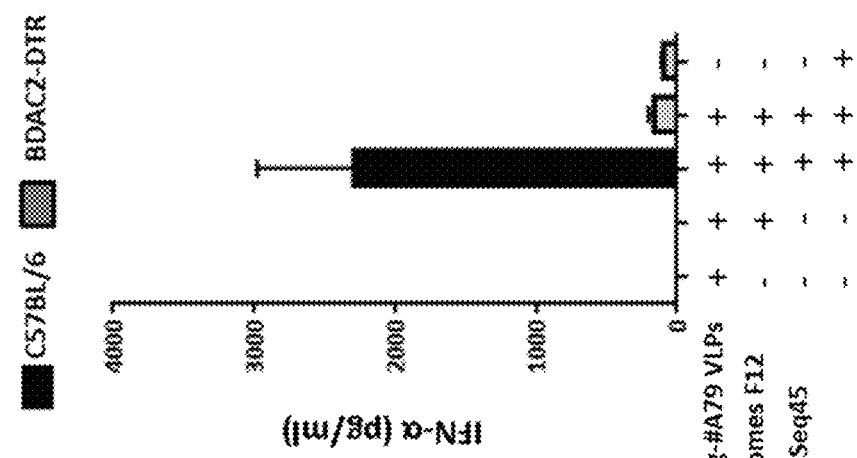

To confirm these results in vivo, BDAC2-DTR mice treated with diphtheria toxin (DT) resulting in the depletion of pDCs and non-treated C57BL/6 wildtype mice were immunized i.v. three times at an interval of 14 days with 50 µg/injection of HBcAg-#A79 VLPs combined with 20 µg/injection of F12-formulated NP71-Seq45 isRNA. Controls were C57BL/6 wildtype mice immunized with HBcAg-#A79 VLPs alone or in combination with empty F12-liposomes and BDAC2-DTR mice treated with DT alone but not receiving the antigen plus isRNA adjuvant. Serum samples were taken 4 h after the first immunization to analyze the induction of IFN-α by ELISA (FIG. 15A) and ten days after the last immunization to determine the induced antigen-specific antibody responses by flow cytometry using CHO-K1 cells stably transfected with the target TAA CLDN6 or its close homologue CLDN9 (FIG. 14B). pDC ablation by diphtheria toxin treatment strongly reduced IFN-α serum levels upon i.v. administration of F12-formulated NP71-Seq45 in combination with HBcAg-#A79 VLPs. The detectable levels were in a similar range as observed for BDAC2-DTR mice treated with DT alone. Injection of non-adjuvanted HBcAg-#A79 VLPs or adjuvanted with empty F12 liposomes did not result in detectable IFN-α serum levels. Analysis of CLDN6 specific antibodies by flow cytometry revealed that the DT mediated depletion of pDCs caused a highly significant reduction in the antigen-specific antibody response upon immunization with F12-formulated NP71-Seq45 isRNA in combination with HBcAg-#A79 VLPs in comparison to C67BL/6 wildtype mice. However, the observed antibody response in BDAC2-DTR mice was still slightly elevated when compared to C57BL/6 mice immunized with non-adjuvanted HBcAg-#A79 VLPs.

The results indicated that pDCs are the main targets and IFN-α producers upon i.v. administration of formulated isRNAs in vivo and confirmed previous in vitro studies. In addition, the lack of IFN-α induction led to a strongly diminished antigen-specific humoral immune response.

Figure 16:
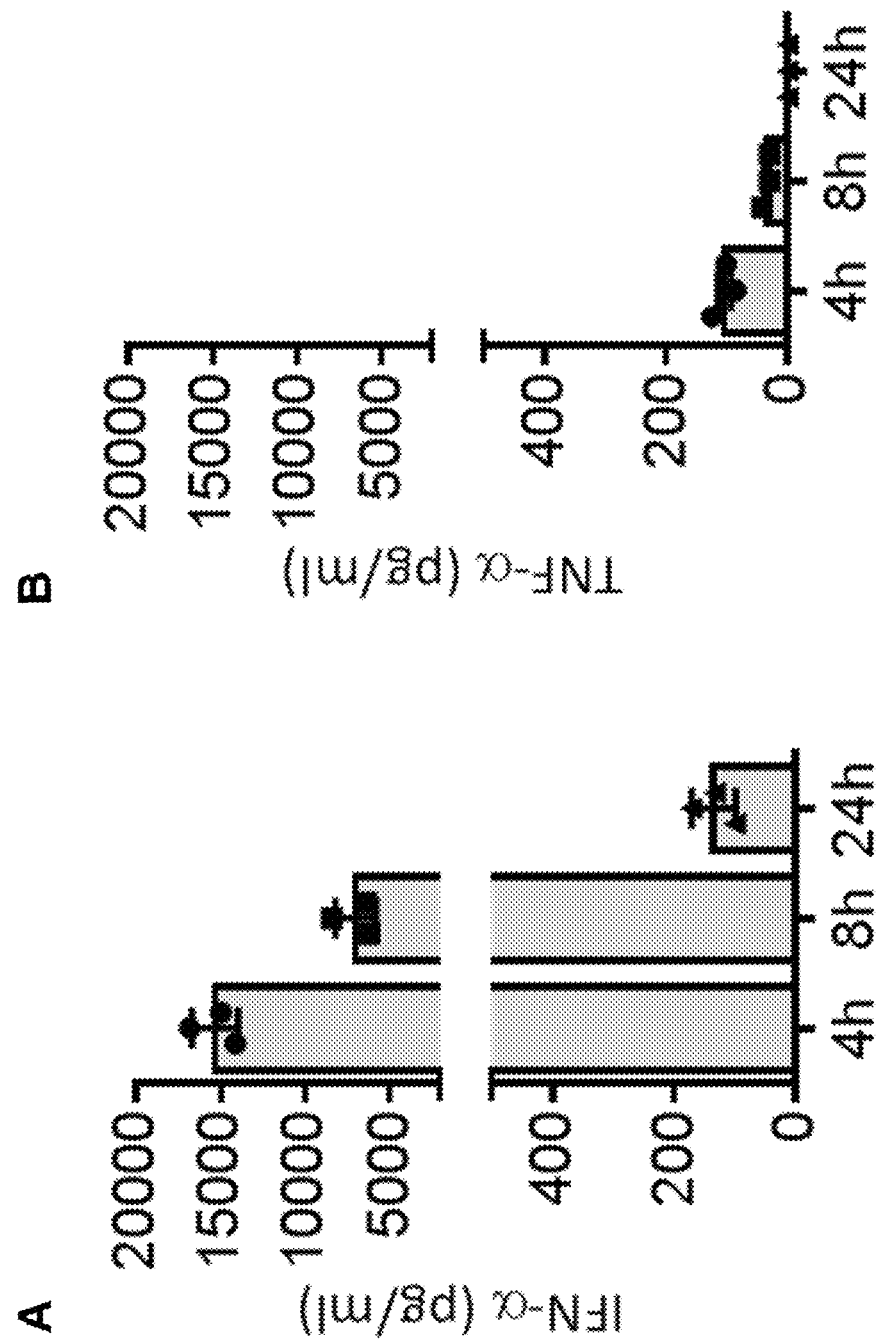
FIG. 16: Cytokine induction by F12-formulated isRNA in vivo.

Example 16: F12-Formulated isRNA Stimulation Results in Substantial IFN-α and Only Marginal TNF-α Induction In Vivo Previous in vitro data using mouse or human immune cells demonstrated the ability of the identified isRNAs, particularly sequence NP71-Seq45, to induce high levels of type I interferon (IFN-α) and only marginal levels of the strongly pro-inflammatory cytokine TNF-α. To investigate whether formulated isRNAs can induce a similar cytokine profile in vivo, Balb/c mice were administered i.v. once with F12-formulated NP71-Seq45 isRNA. Thereafter, sera were collected at various time points (4, 8 and 24 h after injection) and IFN-α or TNF-α levels in the sera were analyzed by commercially available ELISA Kits (Thermo Fischer). In accordance with previously obtained in vitro data, we were able to clearly demonstrate that i.v. administration of F12-formulated NP71-Seq45 isRNA resulted in a very high but transient secretion of IFN-α, while TNF-α levels remained very low (FIG. 16).

The sequences referred to herein are as follows:

```
                                      SEQ ID NO: 1
aacuucugga gggguga

SEQ ID NO: 2
aacuucugga gggugagaa u

SEQ ID NO: 3
uugcuu

SEQ ID NO: 4
aagaauugcu u

SEQ ID NO: 5
gggcgaacua guaacuucug gaggggugag aaucucga

SEQ ID NO: 6
aacuucugga ggggugauug cuu

SEQ ID NO: 7
gggcgaacua guaacuucug gaggggugau ugcuucucga

SEQ ID NO: 8
aacuucugga ggggugagaa uggacgaaaa acaagaauug cuu

SEQ ID NO: 9
gggcgaacua guaacuucug gaggggugag aauggacgaa
aaacaagaau ugcuucucga

SEQ ID NO: 10
aacuucugga ggggugagaa uaagaauugc uu

SEQ ID NO: 11
gggcgaacua guaacuucug gaggggugag aauaagaauu
gcuucucga

SEQ ID NO: 12
agcaaaagca ggguagauaa ucacucacug agugacauca
aaaucauggc gucucaaggc accaaacgau cuuacgaaca
gauggagacu gauggagaac gccagaaugc cacugaaauc
agagcauccg ucggaaaaau gauuggugga auuggacgau
```

```
-continued
ucuacaucca aaugugcacc gaacucaaac ucagugauua ugagggacgg uugauccaaa acagcuuaac aauagagaga auggugcucu cugcuuuuga cgaaaggaga aauaaauacc uugaagaaca ucccagugcg gggaaagauc cuaagaaaac uggaggaccu auauacagga gaguaaacgg aaaguggaug agagaacuca uccuuauga caaagaagaa auaaggcgaa ucuggcgcca agcuaauaau ggugacgaug caacggcugg ucugacucac augaugaucu ggcauuccaa uuugaaugau gcaacuuauc agaggacaag agcucuuguu cgcaccggaa uggaucccag gaugugcucu cugaugcaag guucaacucu cccuaggagg ucuggagccg caggugcugc agucaaagga guuggaacaa uggugaugga auuggucaga augaucaaac gugggaucaa ugaucggaac uucuggaggg gugagaaugg acgaaaaaca agaauugcuu augaaagaau gugcaacauu cucaaaggga aauuucaaac ugcugcacaa aaagcaauga uggaucaagu gagagagagc cggaacccag ggaaugcuga guucgaagau cucacuuuuc uagcacgguc ugcacucaua uugagagggu cgguugcuca caaguccugc cugccugccu
```

```
-continued
guguguaugg accugccgua gccagugggu acgacuuuga aagggaggga uacucucuag ucggaauaga cccuuucaga cugcuucaaa acagccaagu guacagccua aucagaccaa augagaaucc agcacacaag agucaacugg uguggauggc augccauucu gccgcauuug aagaucuaag aguauuaagc uucaucaaag ggacgaaggu gcucccaaga gggaagcuuu ccacuagagg aguucaaauu gcuuccaaug aaaauaugga gacuauggaa ucaaguacac uugaacugag aagcagguac ugggccauaa ggaccagaag uggaggaaac accaaucaac agagggcauc ugcgggccaa aucagcauac aaccuacguu cucaguacag agaaaucucc cuuuugacag aacaaccguu auggcagcau ucagugggaa uacagagggg agaacaucug acaugaggac cgaaaucaua aggaugaugg aaagugcaag accagaagau gugucuuucc aggggcgggg agucuucgag cucucggacg aaaaggcagc gagcccgauc gugccuuccu uugacaugag uaaugaagga ucuuauuucu ucggagacaa ugcagaggaa uacgauaauu aaagaaaaau acccuuguuu cuacu
```

---

The invention claimed is:

1. A method for stimulating an immune response in a subject comprising providing to the subject at least one antigen and providing an immunostimulatory RNA molecule, the immunostimulatory RNA molecule comprising (i) a sequence selected from the group consisting of the sequence of SEQ ID NO: 1, the sequence of SEQ ID NO: 2, and the sequence of SEQ ID NO: 5, and, wherein said immunostimulatory RNA molecule optionally further comprises the sequence of SEQ ID NO: 3 or the sequence of SEQ ID NO: 4; or (ii) a sequence selected from the group consisting of the sequence of SEQ ID NO: 6, the sequence of SEQ ID NO: 7, the sequence of SEQ ID NO: 8, the sequence of SEQ ID NO: 9, the sequence of SEQ ID NO: 10, and the sequence of SEQ ID NO: 11.

2. The method of claim 1, wherein the immunostimulatory RNA molecule is capable of inducing an antigen specific immune response in the subject.

3. The method of claim 1, wherein the immune response comprises a B cell response.

4. The method of claim 1, wherein the immune response comprises the production of IgG antibodies associated with a Th1-like response.

5. The method of claim 1, wherein the immunostimulatory RNA molecule is a toll-like receptor (TLR) agonist.

6. The method of claim 5, wherein the TLR is TLR7.

7. The method of claim 1, wherein the immunostimulatory RNA molecule is capable of inducing secretion of interferon alpha.

8. The method of claim 7, wherein secretion of interferon alpha involves plasmacytoid dendritic cells.

9. The method of claim 1, wherein the immunostimulatory RNA molecule does not substantially induce secretion of one or more of tumor necrosis factor alpha, interferon gamma and interleukin 10.

10. The method of claim 1, wherein the at least one antigen is selected from the group consisting of cancer, virus, bacterial, fungal, or parasite antigens.

11. The method of claim 1, wherein the subject is a mammal.

12. The method of claim 1, wherein the subject is a human.

13. A method for stimulating an immune response in a subject comprising providing to the subject at least one antigen and providing an immunostimulatory RNA molecule, wherein the immunostimulatory RNA molecule is selected from the group consisting of SEQ ID NOs: 1, 5, 6, 7, 8, 9, 10, and 11.

14. The method of claim 13, wherein the immunostimulatory RNA molecule is SEQ ID NO: 11.

15. The method of claim 13, wherein the immunostimulatory RNA molecule is formulated in a liposomal formulation.

16. The method of claim 15, wherein the liposomal formulation comprises 1,2-di-O-octadecenyl-3-trimethylammonium propane (DOTMA) and 1,2-di-(9Z-octadecenoyl)-sn-glycero-3-phosphoethanolamine (DOPE).

17. The method of claim 13, wherein the at least one antigen is a tumor antigen.

18. The method of claim 17, wherein the tumor antigen is Claudin-18.2 or Claudin-6.

19. A method for stimulating an immune response in a subject comprising providing to the subject at least one antigen and providing an immunostimulatory RNA molecule, the immunostimulatory RNA molecule comprising the sequence of SEQ ID NO: 1.

20. The method of claim 19, wherein the immunostimulatory RNA molecule is formulated in a liposomal formulation.

21. The method of claim 20, wherein the liposomal formulation comprises 1,2-di-O-octadecenyl-3-trimethylammonium propane (DOTMA) and 1,2-di-(9Z-octadecenoyl)-sn-glycero-3-phosphoethanolamine (DOPE).

22. The method of claim 19, wherein the immunostimulatory RNA molecule comprises the sequence of SEQ ID NO: 11.

23. The method of claim 22, wherein the immunostimulatory RNA molecule is formulated in a liposomal formulation.

24. The method of claim 23, wherein the liposomal formulation comprises 1,2-di-O-octadecenyl-3-trimethylammonium propane (DOTMA) and 1,2-di-(9Z-octadecenoyl)-sn-glycero-3-phosphoethanolamine (DOPE).

25. The method of claim 19, wherein the immunostimulatory RNA molecule comprises the sequence of SEQ ID NO: 11 and wherein the at least one antigen is a tumor antigen.

26. The method of claim 25, wherein the tumor antigen is Claudin-18.2 or Claudin-6.

27. The method of claim 25, wherein the immunostimulatory RNA molecule is formulated in a liposomal formulation.

28. The method of claim 27, wherein the liposomal formulation comprises 1,2-di-O-octadecenyl-3-trimethylammonium propane (DOTMA) and 1,2-di-(9Z-octadecenoyl)-sn-glycero-3-phosphoethanolamine (DOPE).

29. The method of claim 14, wherein the immunostimulatory RNA molecule is formulated in a liposomal formulation.

30. The method of claim 29, wherein the liposomal formulation comprises 1,2-di-O-octadecenyl-3-trimethylammonium propane (DOTMA) and 1,2-di-(9Z-octadecenoyl)-sn-glycero-3-phosphoethanolamine (DOPE).

* * * * *

SEQUENCE LISTING

<160> NUMBER OF SEQ ID NOS: 12

<210> SEQ ID NO 1
<211> LENGTH: 17
<212> TYPE: RNA
<213> ORGANISM: Artificial Sequence
<220> FEATURE:
<223> OTHER INFORMATION: Sequence of immunostimulatory RNA molecule

<400> SEQUENCE: 1
aacuucugga gggguga                                              17

<210> SEQ ID NO 2
<211> LENGTH: 21
<212> TYPE: RNA
<213> ORGANISM: Artificial Sequence
<220> FEATURE:
<223> OTHER INFORMATION: Sequence of immunostimulatory RNA molecule

<400> SEQUENCE: 2
aacuucugga ggggugagaa u                                         21

<210> SEQ ID NO 3
<211> LENGTH: 6
<212> TYPE: RNA
<213> ORGANISM: Artificial Sequence
<220> FEATURE:
<223> OTHER INFORMATION: Sequence of immunostimulatory RNA molecule

<400> SEQUENCE: 3 uugcuu                                                           6

```
<210> SEQ ID NO 4
<211> LENGTH: 11
<212> TYPE: RNA
<213> ORGANISM: Artificial Sequence
<220> FEATURE:
<223> OTHER INFORMATION: Sequence of immunostimulatory RNA molecule

<400> SEQUENCE: 4
aagaauugcu u                                                              11

<210> SEQ ID NO 5
<211> LENGTH: 38
<212> TYPE: RNA
<213> ORGANISM: Artificial Sequence
<220> FEATURE:
<223> OTHER INFORMATION: Sequence of immunostimulatory RNA molecule

<400> SEQUENCE: 5
gggcgaacua guaacuucug gaggggugag aaucucga                                 38

<210> SEQ ID NO 6
<211> LENGTH: 23
<212> TYPE: RNA
<213> ORGANISM: Artificial Sequence
<220> FEATURE:
<223> OTHER INFORMATION: Sequence of immunostimulatory RNA molecule

<400> SEQUENCE: 6
aacuucugga ggggugauug cuu                                                 23

<210> SEQ ID NO 7
<211> LENGTH: 40
<212> TYPE: RNA
<213> ORGANISM: Artificial Sequence
<220> FEATURE:
<223> OTHER INFORMATION: Sequence of immunostimulatory RNA molecule

<400> SEQUENCE: 7
gggcgaacua guaacuucug gaggggugau ugcuucucga                               40

<210> SEQ ID NO 8
<211> LENGTH: 43
<212> TYPE: RNA
<213> ORGANISM: Artificial Sequence
<220> FEATURE:
<223> OTHER INFORMATION: Sequence of immunostimulatory RNA molecule

<400> SEQUENCE: 8
aacuucugga ggggugagaa uggacgaaaa acaagaauug cuu                           43

<210> SEQ ID NO 9
<211> LENGTH: 60
<212> TYPE: RNA
<213> ORGANISM: Artificial Sequence
<220> FEATURE:
<223> OTHER INFORMATION: Sequence of immunostimulatory RNA molecule

<400> SEQUENCE: 9
gggcgaacua guaacuucug gaggggugag aauggacgaa aacaagaauu gcuucucga          60

<210> SEQ ID NO 10
<211> LENGTH: 32
<212> TYPE: RNA
<213> ORGANISM: Artificial Sequence
<220> FEATURE:
<223> OTHER INFORMATION: Sequence of immunostimulatory RNA molecule
```

```
<400> SEQUENCE: 10
aacuucugga ggggugagaa uaagaauugc uu                                    32

<210> SEQ ID NO 11
<211> LENGTH: 49
<212> TYPE: RNA
<213> ORGANISM: Artificial Sequence
<220> FEATURE:
<223> OTHER INFORMATION: Sequence of immunostimulatory RNA molecule

<400> SEQUENCE: 11
gggcgaacua guaacuucug gaggggugag aauaagaauu gcuucucga                  49

<210> SEQ ID NO 12
<211> LENGTH: 1565
<212> TYPE: RNA
<213> ORGANISM: Influenza A virus

<400> SEQUENCE: 12
agcaaaagca gguagauaa ucacucacug agugacauca aaaucauggc gucucaaggc       60
accaaacgau cuuacgaaca gauggagacu gauggagaac gccagaaugc cacugaaauc     120
agagcauccg ucggaaaaau gauuggugga auuggacgau ucuacaucca aaugugcacc     180
gaacucaaac ucagugauua ugagggacgg uugauccaaa acagcuuaac aauagagaga     240
auggugcucu cugcuuuuga cgaaaggaga auuaaauacc uugaagaaca ucccagugcg     300
gggaaagauc cuaagaaaac uggaggaccu auauacagga gaguaaacgg aaaguggaug     360
agagaacuca uccuuuauga caaagaagaa auaaggcgaa ucuggcgcca agcuaauaau     420
ggugacgaug caacggcugg ucugacucac augaugaucu ggcauccaa uuugaaugau     480 gcaacuuauc agaggacaag agcucuuguu cgcaccggaa uggaucccag gaugugcucu     540
cugaugcaag guucaacucu cccuaggagg ucuggagccg caggugcugc agucaaagga     600
guuggaacaa uggugaugga auuggucaga augaucaaac gugggaucaa ugaucggaac     660
uucuggaggg gugagaaugg acgaaaaaca agaauugcuu augaaagaau gugcaacauu     720
cucaaaggga aauuucaaac ugcugcacaa aaagcaauga uggaucaagu gagagagagc     780
cggaacccag ggaaugcuga guucgaagau cucacuuuuc uagcacgguc ugcacucaua     840
uugagagggu cgguugcuca caaguccugc cugccugccu ugugguaugg accugccgua     900 gccaguggu acgacuuuga aagggaggga uacucucuag ucggaauaga cccuuucaga     960
cugcuucaaa acagccaagu guacagccua aucagaccaa augagaaucc agcacacaag    1020
agucaacugg uguggauggc augccauucu gccgcauuug aagaucuaag aguauuaagc    1080
uucaucaaag ggacgaaggu gcucccaaga gggaagcuuu ccacuagagg aguucaaauu    1140
gcuuccaaug aaaauaugga gacuauggaa ucaaguacac uugaacugag aagcagguac    1200 uggccauaa ggaccagaag uggaggaaac accaaucaac agagggcauc ugcgggccaa    1260
aucagcauac aaccuacguu cucaguacag agaaaucucc cuuuugacag aacaaccguu    1320
auggcagcau ucagugggaa uacagagggg agaacaucug acaugaggac cgaaaucaua    1380
aggaugaugg aaagugcaag accagaagau gugucuuucc aggggcgggg agucuucgag    1440
cucucggacg aaaaggcagc gagcccgauc gugccuccu uugacaugag uaaugaagga    1500
ucuuauuucu ucggagacaa ugcagaggaa uacgauaauu aaagaaaaau acccuuguuu    1560
cuacu                                                               1565
```